(12) United States Patent
Leinsing et al.

(10) Patent No.: US 6,706,022 B1
(45) Date of Patent: Mar. 16, 2004

(54) NEEDLELESS MEDICAL CONNECTOR WITH EXPANDABLE VALVE MECHANISM

(75) Inventors: Karl R. Leinsing, Raleigh, NC (US); Theodore J. Mosler, Raleigh, NC (US)

(73) Assignee: ALARIS Medical Systems, Inc., San Diego, CA (US)

( * ) Notice: Subject to any disclaimer, the term of this patent is extended or adjusted under 35 U.S.C. 154(b) by 0 days.

(21) Appl. No.: 09/361,543

(22) Filed: Jul. 27, 1999

(51) Int. Cl.[7] .................................................. A61M 5/00
(52) U.S. Cl. ...................................... 604/247; 604/256
(58) Field of Search ........................... 604/34, 256, 36, 604/905, 284, 99.02, 99.03, 99.04, 167.03, 236, 247, 249, 288.03, 323, 335

(56) References Cited

U.S. PATENT DOCUMENTS

| | | | |
|---|---|---|---|
| 4,479,795 A | 10/1984 | Mustachich et al. | 604/53 |
| 4,810,241 A | 3/1989 | Rogers | 604/28 |
| 4,919,658 A | 4/1990 | Badia | 604/265 |
| 5,195,994 A | 3/1993 | Dieringer | 604/283 |
| 5,215,538 A | 6/1993 | Larkin | 604/249 |
| 5,242,432 A * | 9/1993 | DeFrank | 604/284 |
| 5,360,413 A | 11/1994 | Leason et al. | 604/249 |
| 5,509,433 A * | 4/1996 | Paradis | 604/249 |
| 5,676,346 A | 10/1997 | Leinsing | 251/149.1 |
| RE35,841 E | 7/1998 | Frank et al. | 604/256 |
| 5,820,601 A | 10/1998 | Mayer | 604/167 |
| 5,839,715 A * | 11/1998 | Leinsing | 604/905 |
| 6,029,946 A * | 2/2000 | Doyle | 604/256 |
| 6,039,302 A * | 3/2000 | Cote, Sr. et al. | 604/256 |
| 6,117,114 A * | 9/2000 | Paradis | 604/246 |
| 6,290,206 B1 | 9/2001 | Doyle | 251/149.1 |

FOREIGN PATENT DOCUMENTS

| | | | | |
|---|---|---|---|---|
| WO | WO 94/22522 | 10/1994 | | A61M/39/00 |
| WO | WO 98/26835 | 6/1998 | | A61M/39/26 |
| WO | WO 99/24090 | 5/1999 | | A61M/5/00 |

* cited by examiner

*Primary Examiner*—Manuel Mendez
(74) *Attorney, Agent, or Firm*—Fulwider Patton Lee & Utecht, LLP

(57) ABSTRACT

A needleless connector for medical use, adapted to facilitate the flow of fluid therethrough, includes a housing having an inlet port and an outlet port. The connector also includes a flex-tube assembly defining a fluid path between the inlet port and the outlet port. The flex-tube assembly is movable between uncompressed and compressed states. The flex-tube assembly has a first internal volume when in the uncompressed state and a second internal volume, greater than or substantially equal to the first internal volume, when in the compressed state.

20 Claims, 31 Drawing Sheets

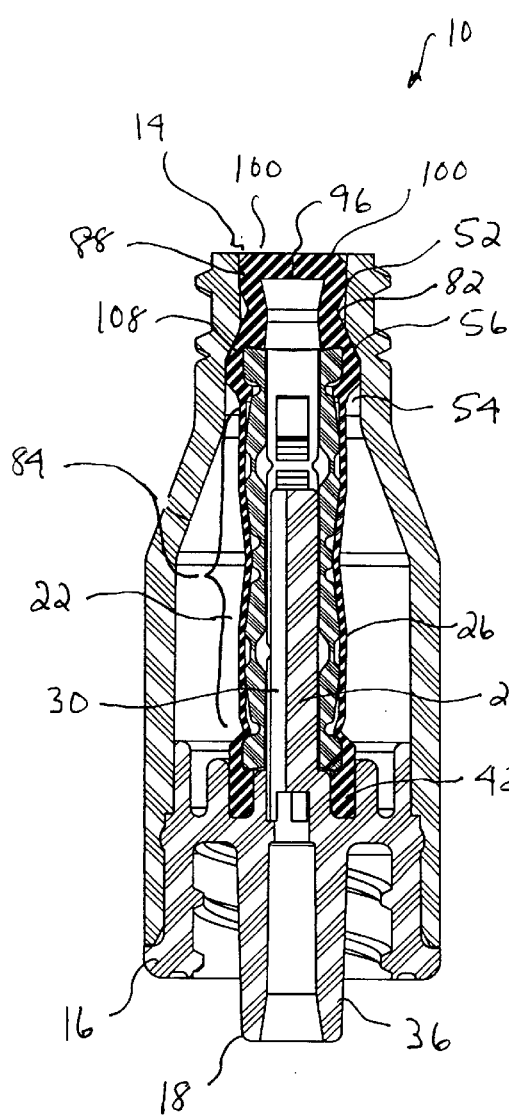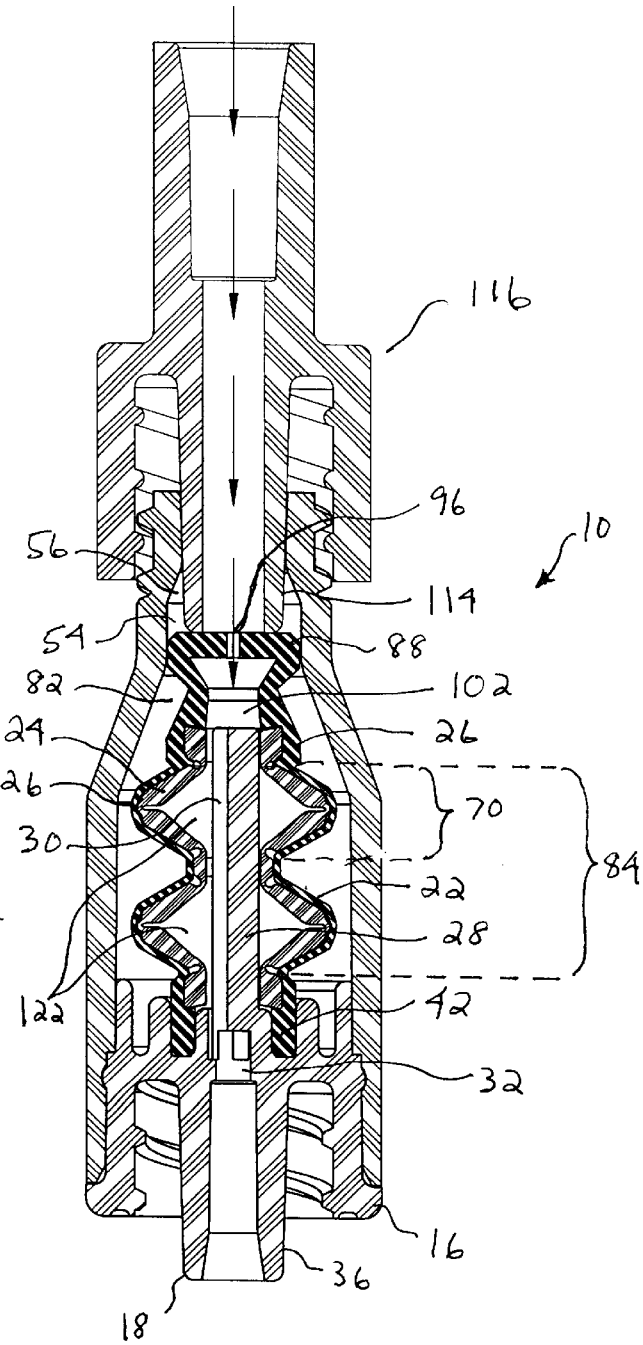
FIG. 14
FIG. 15

NEEDLELESS MEDICAL CONNECTOR WITH EXPANDABLE VALVE MECHANISM

BACKGROUND OF THE INVENTION

The invention relates generally to medical connectors of the type used in the handling and administration of parenteral fluids, and more particularly, to a needleless connector employing a valve mechanism that compensates for negative fluid displacement, i.e., drawing of fluid into the outlet end of a connector, during deactuation of the valve.

Within this specification the terms, "negative-bolus effect," "positive-bolus effect," and "no-bolus effect" are used to describe the operating characteristics of medical connectors during deactuation of the valve mechanisms contained within the connectors. Negative-bolus effect describes the condition during which fluid is drawn into the connector during deactuation. Positive-bolus effect describes the condition during which fluid is flushed out of the connector during deactuation. No-bolus effect describes the condition during which fluid displacement is neutralized and fluid is neither drawn into nor flushed out of the connector during deactuation.

Needleless medical connectors for injecting fluid into or removing fluid from an intravenous (IV) system are well known and widely used. Conventional needleless medical connectors generally include a housing having an inlet port and an outlet port. The inlet port is sized to receive a blunt male cannula, such as a male Luer taper. Disposed within the inlet port is a valve mechanism that provides access to a fluid path that communicates with the outlet port. In some connectors, the fluid path is defined by the internal boundaries of the connector housing, in other connectors it is defined by an internal cannula or hollow spike, still in others, the fluid path is defined by a compressible tubular body which carries the valve mechanism. The outlet port of the connector is typically connected to IV tubing which in turn is connected to an IV catheter that communicates with a patient's venous system.

Many needleless medical connectors create fluid displacement during actuation and deactuation of the valve mechanism. During actuation, the blunt male cannula is inserted into the inlet. In some connectors, the cannula passes through the valve mechanism to establish fluid communication with the fluid path. In other connectors, the cannula merely displaces the valve mechanism, without penetrating it, in order to establish fluid communication with the fluid path. In either case, the volumetric capacity of the fluid path is often reduced by the insertion of the blunt cannula. Subsequently, when the blunt cannula is removed from the connector, the volumetric capacity of the fluid path increases. This increase in the volumetric capacity may create a partial vacuum in the fluid path that may draw fluid into the connector from the outlet end. As previously mentioned, the effect of drawing fluid into the connector in this manner is referred to as a "negative-bolus" effect in that a quantity, or "bolus," of fluid is drawn into the partial vacuum or negative pressure location; i.e., the connector.

A negative-bolus effect is undesirable in that the partial vacuum created within the connector may draw fluid from the IV tubing. The IV tubing in turn draws fluid from the IV catheter which in turn draws fluid, e.g., blood, from the patient's venous system.

The negative-bolus effect may be reduced by undertaking operational safeguards. For instance, prior to the removal of the blunt cannula from the connector, the IV tubing may be clamped off between the connector output port and the IV catheter. This prevents the backup of blood through the IV catheter. If a syringe with a blunt cannula tip is used to inject fluid into the inlet port of the valve, the syringe may be continually depressed while the syringe is disengaged from the connector. The continued depression of the syringe injects fluid into the fluid path to fill the increasing volume thereby reducing the chance of a partial vacuum forming in the fluid path and a negative bolus. However, both of these approaches are undesirable in that the operator must remember to perform an additional step during removal of the syringe or other device from the connector rather than the steps being taken automatically by the connector.

The negative-bolus effect may also be reduced by the design of the medical connector. As previously mentioned, some medical connectors include an internal cannula or hollow spike housed inside the connector body. The internal cannula or spike is positioned to open a septum upon depression of the septum onto the internal cannula or spike by a blunt cannula. The internal cannula or spike has a small orifice at the top and upon depression of the septum is put in fluid communication with the blunt cannula. The internal cannula or spike provides a generally fixed-volume fluid-flow path through the connector. Thus, as the septum returns to its closed position the partial vacuum formed within the connector is not as strong as the vacuum formed in a connector having a more volumetrically dynamic fluid path. A disadvantage of typical connectors having an internal cannula or spike is a lower fluid-flow rate. This low flow rate is caused by the small orifice in the cannula or spike. Additionally, it has been noted that with the connector design having a fixedly-mounted internal spike and a movable septum that is pierced by that spike to permit fluid flow, such pierced septum may be damaged with multiple uses and a leaking connector may result.

Other connectors provide a valve mechanism that includes a flexible silicone body and a rigid spring leaf positioned about an internal cannula. Upon depression of the valve mechanism by a blunt cannula, the internal cannula forces the leaves of the spring leaf apart, the leaves in turn force the top of the body apart and open a slit contained therein. The opening of the slit establishes fluid communication between the blunt cannula and the internal cannula. The body includes a side reservoir that expands upon depression of the valve mechanism and receives fluid. Upon deactuation of the valve mechanism the reservoir collapses between the connector housing and the spring leaf and fluid is forced out of the reservoir into the internal cannula. This displacement of fluid may fill the partial vacuum being formed by the deactuation of the valve mechanism and thus reduce the possibility of fluid being drawn into the connector.

Although these connectors may reduce the negative-bolus effect, they have several disadvantages. First, during periods of nonuse, residual fluid left within the collapsed reservoir is likely to dry and adhere to the leaf spring. This may cause particulate to enter the fluid path during subsequent actuation or may even prevent the reservoir from expanding during subsequent actuation. Second, the connector employs a complex two-part valve mechanism that requires an internal cannula for actuation and deactuation. The complexity of this device lends itself to manufacturing difficulties and increased manufacturing costs. Third, during actuation of the valve mechanism, the leaves of the rigid spring leaf may cut through the body and cause a leak.

Hence, those concerned with the development of medical connectors have recognized the need for a medical connector having a valve mechanism that avoids the negative-bolus effect by producing either a positive-bolus effect or a no-bolus effect. The need for a medical connector that provides these effects without sacrificing fluid-flow rate or structural simplicity has also been recognized. The present invention fulfills such needs and others.

SUMMARY OF THE INVENTION

Briefly, and in general terms, the invention is directed to a medical connector having a valve mechanism that provides either a positive-bolus effect or a no-bolus effect, upon deactuation of the valve mechanism.

In a first aspect, the invention is directed to a needleless connector for medical use, adapted to facilitate the flow of fluid therethrough. The connector includes a housing having an inlet port and an outlet port. The connector also includes a flex-tube assembly defining a fluid path between the inlet port and the outlet port. The flex-tube assembly is movable between uncompressed and compressed states and has a first internal volume when in the uncompressed state and a second internal volume, at least as great as the first internal volume, when in the compressed state.

By providing a flex-tube assembly having an internal volume when compressed, e.g., activated by the insertion of a blunt cannula, that is at least as great as the internal volume when the flex-tube assembly is uncompressed, the possibility of a partial vacuum forming within the fluid path defined by the flex-tube assembly upon removal of the blunt cannula is essentially eliminated and instead, a positive-bolus effect or a no-bolus effect is provided. Thus, fluid is prevented from being drawn into the connector through the outlet port upon removal of the blunt cannula.

In more detailed aspects, the second internal volume is greater than the first internal volume. In another detailed facet, the second internal volume is substantially equal to the first internal volume. In yet another detailed aspect, the flex-tube assembly includes an inlet end that is positioned within the inlet port during the uncompressed state and outside the inlet port during the compressed state. The flex-tube assembly also includes a bore carried by the inlet end. The bore is closed when the inlet end is within the inlet port and opened when the inlet end is outside the inlet port. In a further more detailed aspect, the flex-tube assembly includes a flex-tube insert having at least one collapsible section movable between uncollapsed and collapsed states. The flex-tube assembly also includes a flex-tube piston that surrounds the flex-tube insert and defines the fluid path. The flex-tube piston includes a piston head that is positioned within the inlet port during the uncompressed state and outside the inlet port during the compressed state. The flex-tube piston also includes a bore that is carried by the piston head. The bore is closed when the piston head is within the inlet port and opened when the piston head is outside the inlet port. The flex-tube piston further includes a piston base that is proximal the outlet port and in communication therewith. The flex-tube piston is responsive to the movement of the flex-tube insert. In another aspect, the flex-tube insert includes one collapsible section and the first end is secured within the piston head and the second end is secured within the piston base.

In yet another aspect, the flex-tube insert includes two collapsible sections and a middle support for joining the two collapsible sections. For one collapsible section, the first end is secured within the piston head and the second end is pivotably attached to the middle support. For the other collapsible section, the first end is pivotably attached to the middle support and the second end is secured within the piston base. In another facet, the flex-tube assembly includes at least one collapsible section defining the fluid path, a piston head that is positioned within the inlet port during the uncompressed state and outside the inlet port during the compressed state, and a bore that is carried by the piston head. The bore is closed when the piston head is within the inlet port and opened when the piston head is outside the inlet port. The flex-tube assembly also includes a piston base proximal the outlet port and in communication therewith.

In yet another facet, the flex-tube assembly includes one collapsible section and the first end comprises the piston head and the second end comprises the piston base. In still another facet, the flex-tube assembly includes two collapsible sections and a middle support for joining the two collapsible sections. For one collapsible section, the first end includes the piston head and the second end is pivotably attached to the middle support. For the other collapsible section, the first end is pivotably attached to the middle support and the second end comprises the piston base.

In a second aspect, the invention is related to a valve for providing a fluid path between the inlet port and outlet port of a connector. The valve includes a flex-tube insert that is substantially axially aligned with the axis of the fluid path. The insert is movable between uncompressed and compressed states and has a first maximum inner width while uncompressed and a second maximum inner width, greater than the first maximum inner width, while compressed. The valve also includes a flex-tube piston surrounding the flex-tube insert and defining the radial boundaries of the fluid path. The flex-tube piston includes a piston head for positioning within the inlet port during the uncompressed state and outside the inlet port during the compressed state. The flex-tube piston also includes a bore that is carried by the piston head. The bore is closed when the piston head is within the inlet port and opened when the piston head is outside the inlet port. The flex-tube piston also includes a piston base for positioning proximal the outlet port and providing fluid communication with the outlet port. The flex-tube piston is responsive to movement of the flex-tube insert.

In more detailed aspects, the flex-tube insert includes at least one collapsible section having a maximum cross section when viewed along the axis of the fluid path. The maximum cross section defines the first and second maximum inner widths. In another aspect, each collapsible includes a first end, a second end, and a plurality of hinge assemblies. Each hinge assembly has a hinge and two plates including two substantially parallel edges, one of the edges is attached to the hinge for pivotal movement and the other of the edges is attached to one of either the first or second ends for pivotal movement. In another detailed facet, there are four hinge assemblies arranged so that the flex-tube insert has a substantially square cross section when viewed along the axis of the fluid path and the distance between opposing hinges of the hinge assemblies define the first and second maximum cross sections.

In a third aspect, the invention is directed to a valve for providing a fluid path between the inlet port and outlet port of a connector. The valve includes a collapsible section having a hollow interior defining the radial boundaries of the fluid path. The collapsible section is movable between uncompressed and compressed states and has a first maximum cross-sectional area while uncompressed and a second maximum cross-sectional area, greater than the first maximum cross-sectional area, while compressed. The valve also includes a piston head at one end of the collapsible section for positioning within the inlet port during the uncompressed state and outside the inlet port during the compressed state and a bore carried by the piston head. The bore is closed when the piston head is within the inlet port and opened and communicating with the interior of the collapsible section when the piston head is outside the inlet port. The valve also includes a piston base at the other end of the collapsible section for positioning proximal the outlet port and providing communication with the outlet port.

In a more detailed facet, the collapsible section includes at least one collapsible portion having a maximum cross-sectional area when viewed along the axis of the fluid path. The maximum cross-sectional area defines the first and second maximum cross-sectional areas. In another facet, each collapsible portion includes a first end, a second end, and a plurality of hinge assemblies. Each hinge has a hinge and two plates including two substantially parallel edges. One of the edges is attached to the hinge for pivotal movement and the other of the edges is attached to one of either the first or second ends for pivotal movement. The collapsible portion further includes a plurality of resiliently deformable webs joining the edges of adjacent hinge assemblies to seal the interior of the collapsible section. In a more detailed facet, there are three hinge assemblies arranged so that the collapsible portion has a substantially triangular cross section when viewed along the axis of the fluid path.

In a fourth aspect, the invention is related to a method of controlling the flow of fluid between an inlet port and an outlet port of a medical connector having a valve assembly defining a fluid path having an internal volume. The valve assembly has an inlet end disposed within the inlet port and an outlet end communicating with the outlet port. The inlet end carries a bore that is closed when within the inlet end and opened when outside the inlet port. The method includes the steps of increasing the internal volume of the fluid path while simultaneously opening the bore and subsequently decreasing the internal volume of the fluid path while simultaneously closing the bore.

In a more detailed aspect, the valve assembly is formed of a resiliently deformable material and the step of increasing the internal volume of the fluid path while opening the bore includes the steps of displacing the inlet end from the inlet port and expanding the valve assembly in a generally radial outward direction relative to the axis of the fluid flow path. In another aspect, the step of displacing the inlet end from the inlet port includes the step of inserting a male-Luer taper into the inlet port and applying pressure to the inlet end. In yet another facet, the step of decreasing the internal volume of the fluid path while closing the bore includes the steps of placing the inlet end in the inlet port and collapsing the valve assembly in a generally radial inward direction relative to the axis of the fluid flow path. In still another facet, the step of placing the inlet end in the inlet port comprises the step of removing the male-Luer taper from the inlet port.

In a fifth aspect, the invention is directed to a method of controlling the flow of fluid between an inlet port and an outlet port of a medical connector having an axially compressible valve assembly defining a fluid path having an internal volume. The valve assembly has an inlet end disposed within the inlet port and an outlet end communicating with the outlet port. The inlet end carryies a bore that is closed when within the inlet end and opened when outside the inlet port. The method includes the steps of maintaining the internal volume of the fluid path substantially constant while axially compressing the valve assembly and opening the bore; and subsequently maintaining the internal volume of the fluid path substantially constant while axially decompressing the valve assembly and closing the bore.

In a sixth aspect, the invention is related to a connector for medical use, adapted to facilitate the flow of fluid therethrough. The connector includes an inlet port, an outlet port and a valve assembly defining a fluid path between the inlet port and the outlet port. At least one of the inlet port, the outlet port and the valve assembly is formed to include an antimicrobial agent.

These and other aspects and advantages of the invention will become apparent from the following detailed description and the accompanying drawings, which illustrate by way of example the features of the invention.

BRIEF DESCRIPTION OF THE DRAWINGS

FIG. 14 is a full sectional view of a positive-bolus configuration of the medical connector shown in FIG. 1 depicting the flex-tube assembly in the uncompressed state;

FIG. 15 is a full sectional view of a positive-bolus configuration of the medical connector shown in FIG. 1 depicting the flex-tube assembly in the compressed state under pressure of an inserted blunt or needle-free cannula having a male Luer taper;

FIG. 25a depicts the flex-tube assembly in an uncompressed state while FIG. 25b depicts it in a compressed state;

DETAILED DESCRIPTION OF PREFERRED EMBODIMENTS

Figure 1:
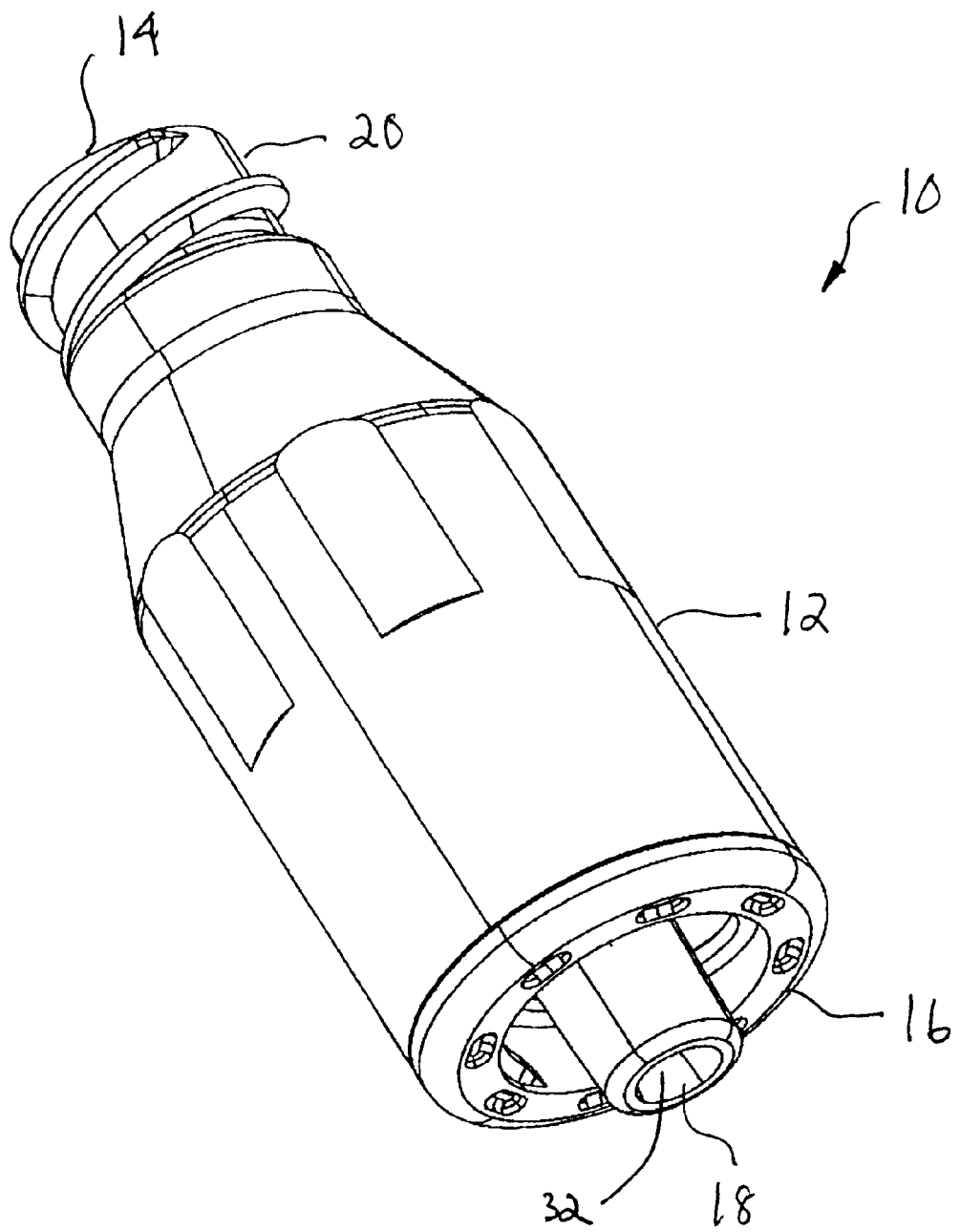
FIG. 1 is a perspective view of a medical connector that incorporates aspects of the present invention.
Figure 16:
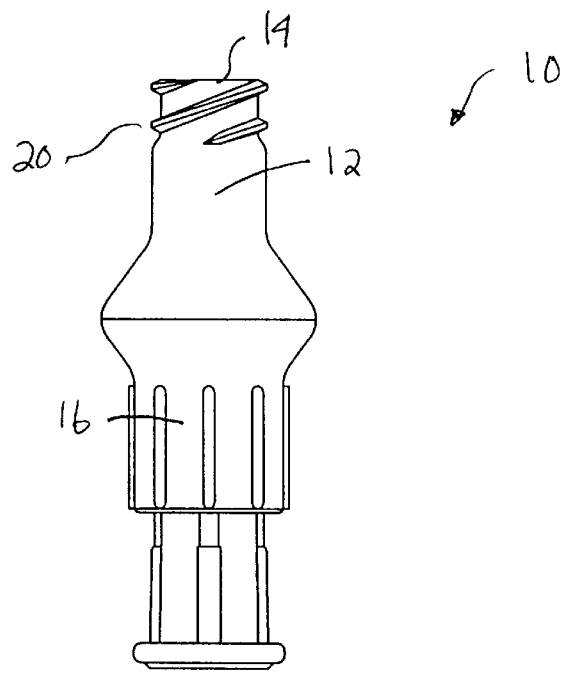
FIG. 16 is an elevation view of another medical connector that incorporates aspects of the present invention.
Figure 19:
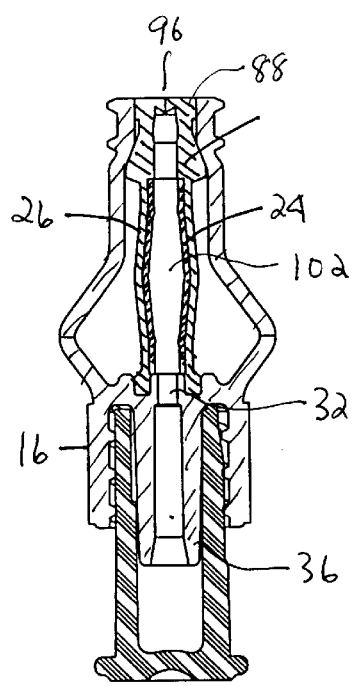
FIG. 19 is a full sectional view of the medical connector shown in FIG. 16 depicting the flex-tube assembly in the uncompressed state.
Figure 20:
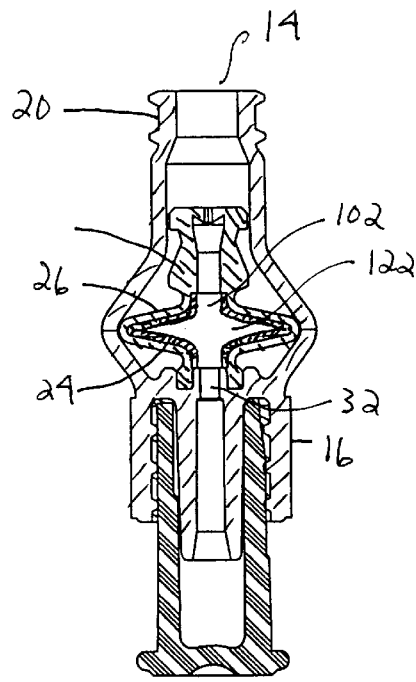
FIG. 20 is a full sectional view of the medical connector shown in FIG. 16 depicting the flex-tube assembly in the compressed state.
Figure 17B:
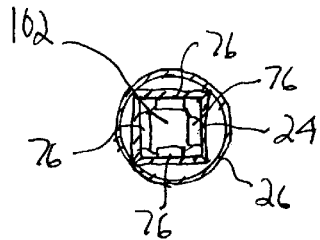
FIG. 17b is a top view of the flex-tube assembly shown in FIG. 17a taken along the line 17b—17b.
Figure 21:
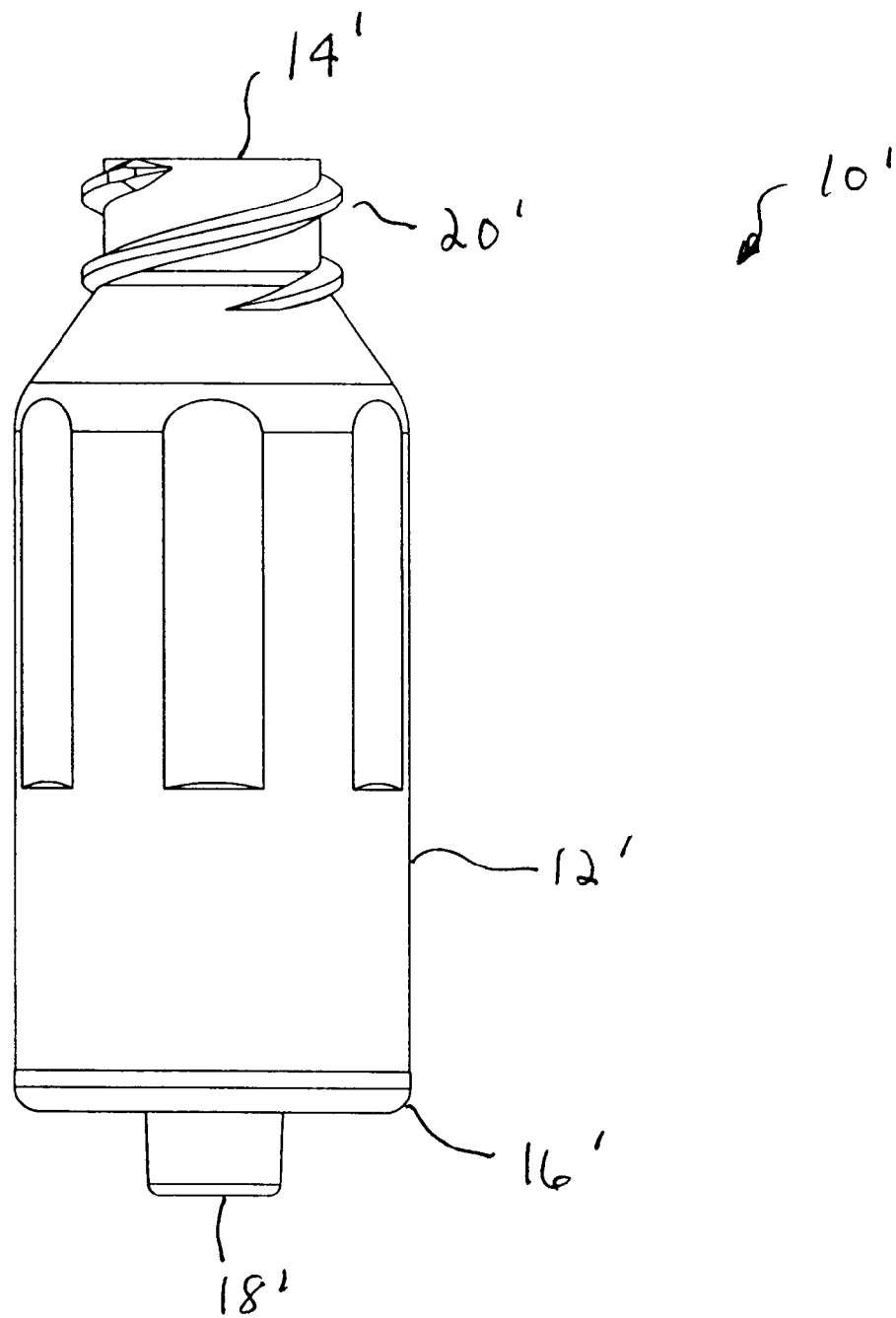
FIG. 21 is an elevation view of another medical connector that incorporates aspects of the present invention.

Referring now to the drawings in which like numerals refer to like or corresponding elements among the several figures, there is illustrated in FIGS. 1, 16 and 21 several medical connectors that include a needleless valve embodying aspects of the invention, These particular connector configurations are for illustration purposes only. The subject needleless valve can be embodied in any of a variety of connectors including, but not limited to, Y-connectors, J-loops, T-Connectors, Tri-connectors, PRN adapters, slip Luers, tubing engagement devices, access pins, vail adapters, blood tube adapters, bag access pins, and vented adapters.

Figure 2:
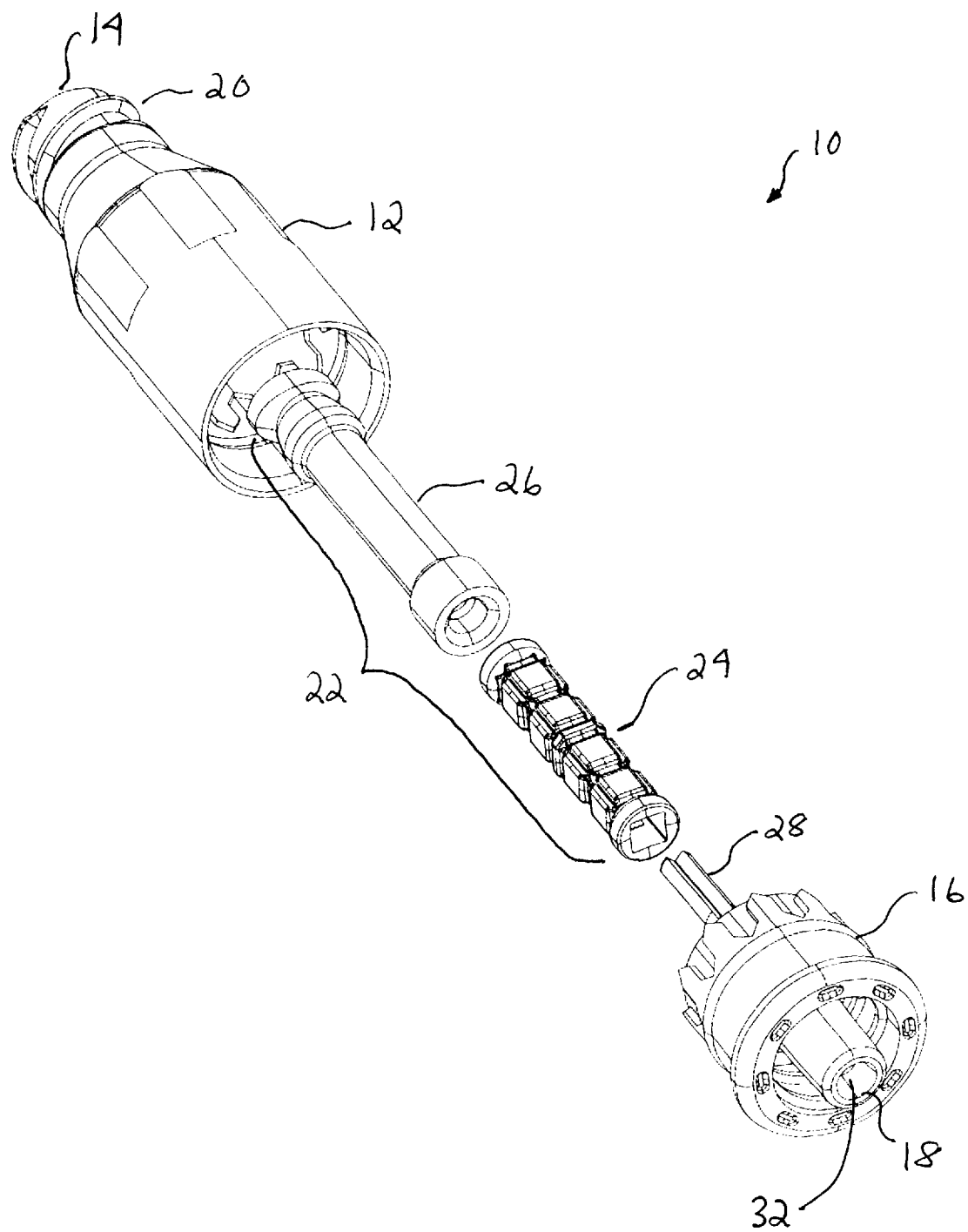
FIG. 2 is an exploded perspective view of the medical connector shown in FIG. 1 depicting a valve body, a male Luer lock insert, and a flex-tube assembly, i.e., valve assembly, including a flex-tube piston and a flex-tube insert.
Figure 3:
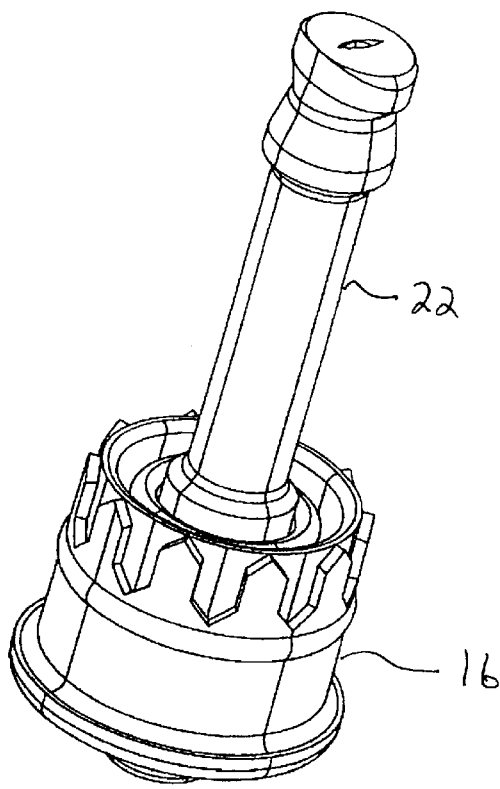
FIG. 3 is a perspective view of the medical connector shown in FIG. 1 with the valve body removed and depicting the flex-tube assembly positioned on the male Luer lock insert.
Figure 4:
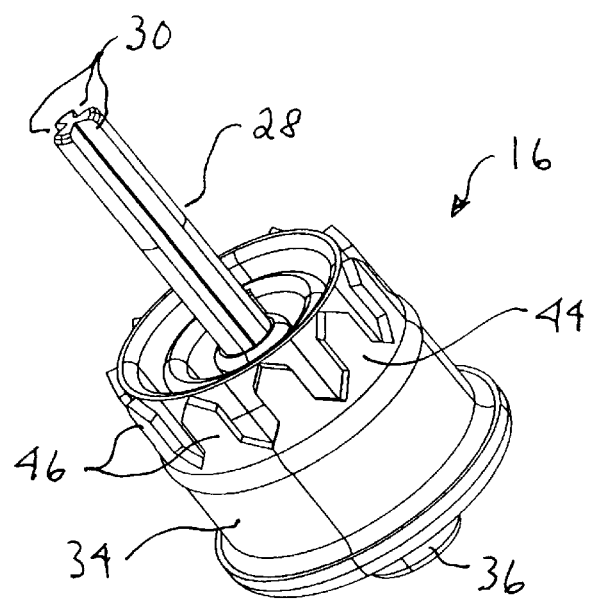
FIG. 4 is perspective view of the male Luer lock insert shown in FIGS. 1–3.
Figure 5B:
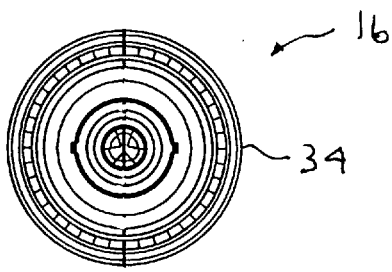
FIGS. 5a–5d depict various views of the male Luer-lock insert shown in FIG. 4 including a side elevation view, a top plan view, a bottom plan view and a full sectional view.
Figure 5A:
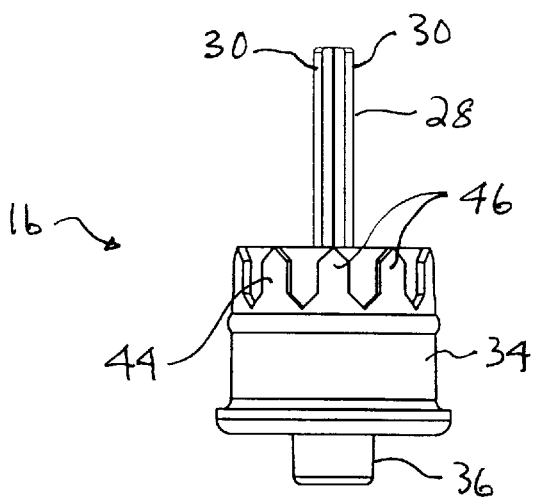
Figure 5D:
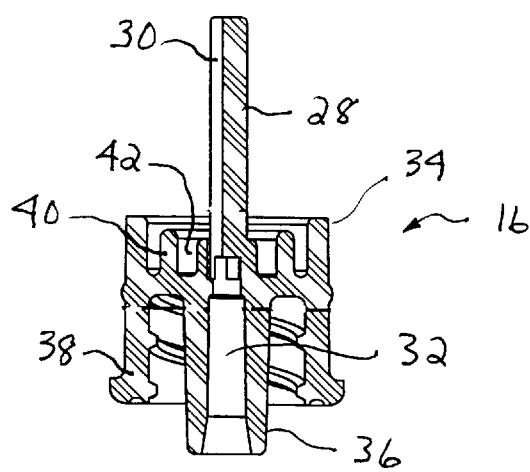
Figure 5C:
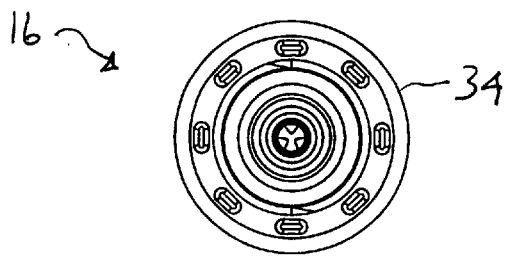

As is shown in FIGS. 1 and 2, the connector 10 comprises a valve body 12 having an inlet port 14. The connector 10 further includes a male Luer-lock insert 16 terminating in an outlet port 18. The valve body 12 and the male Luer-lock insert form a connector housing. The portion of the valve body 12 near the inlet port 14 includes a Luer adapter 20. The adapter 20 is configured to receive all ANSI standard male Luer fittings, as well as other blunt cannulas or fluid conduit devices. The connector 10 also includes a resiliently deformable flex-tube assembly 22, i.e., valve assembly, which includes a flex-tube insert 24 disposed within a flex-tube piston 26. As shown in FIGS. 3 and 4, the male Luer-lock insert 16 includes a support post 28 for receiving the flex-tube assembly 22. The support post 28 has three vertical channels 30 running the length of the post and terminating at the proximal end of the tubular-housing fluid path 32.

As shown in FIGS. 5a–5d, these channels 30 guide fluid through the connector along the length of the support post 28 and into the tubular-housing fluid path 32 of the Luer-lock insert 16. The male Luer-lock insert 16 includes a tubular housing 34 having a circular cross-section. Extending upward from the center of the tubular housing 34 is the support post 28. Extending downward from the center of the tubular housing 34 is a male-Luer taper 36. The tubular housing 34 includes an outer shroud 38 and an inner shroud 40. The outer shroud 38 surrounds the base of the support post 28 and most of the male-Luer taper 36. The portion of the outer shroud 38 surrounding the male-Luer taper 36 is internally threaded. The inner shroud 40 also surrounds the base of the support post 28. The space between the base of the support post 28 and the inner shroud 40 forms an annular groove 42. As described further below, the annular groove 42 is used to secure the base of the flex-tube assembly 22.

Figure 6:
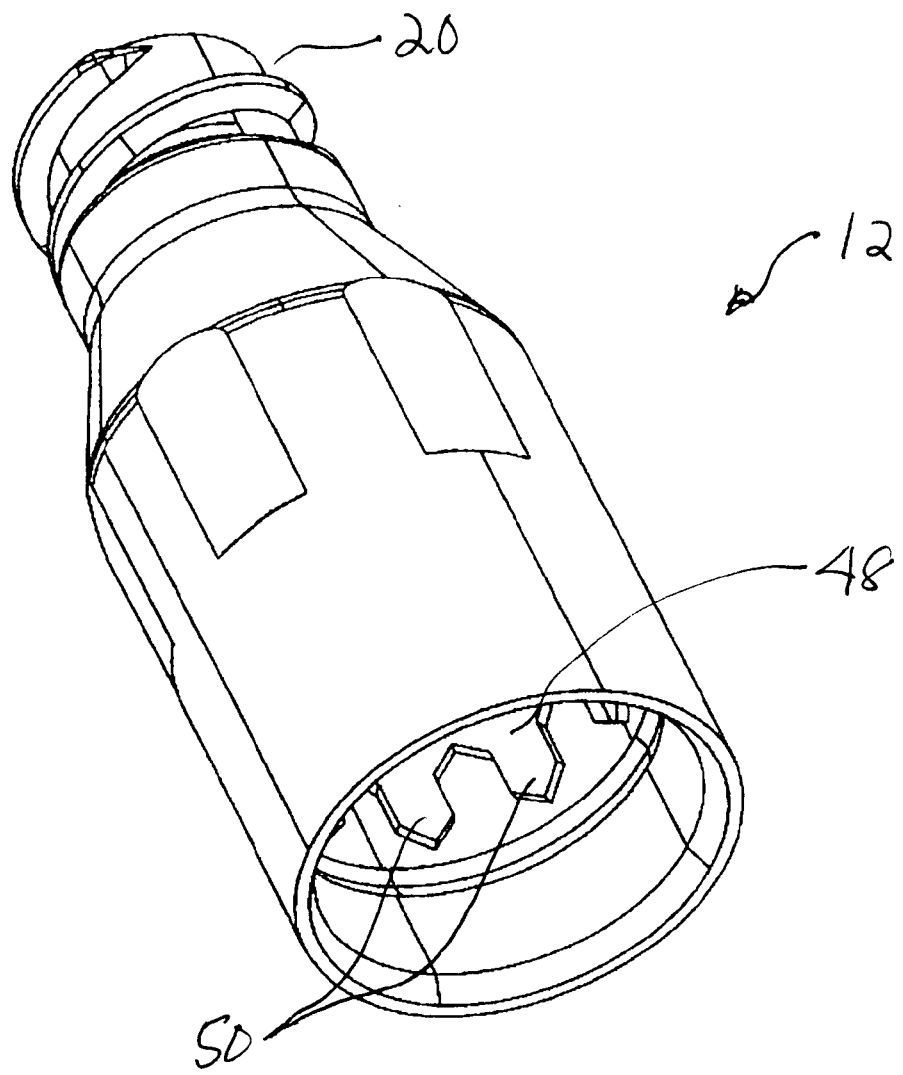
FIG. 6 is a perspective view of the valve body shown in FIG. 1.
Figure 7B:
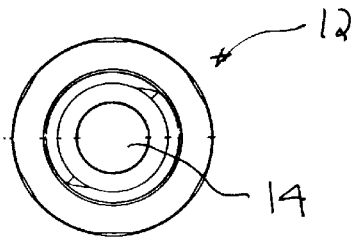
FIGS. 7a–7d depict various views of the valve body shown in FIGS. 2 and 6 including a side elevation view, a top plan view, a bottom plan view and a full sectional view.
Figure 7A:
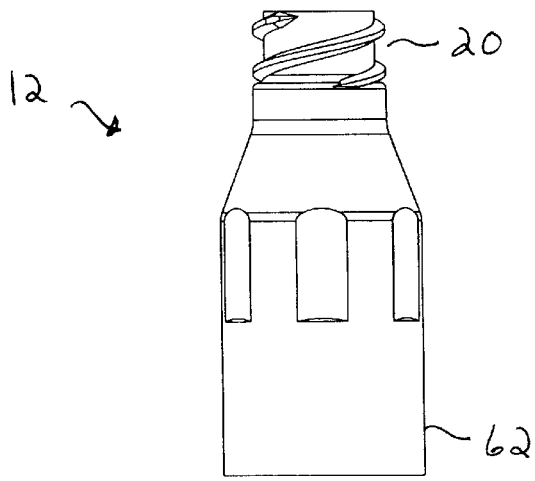
Figure 7D:
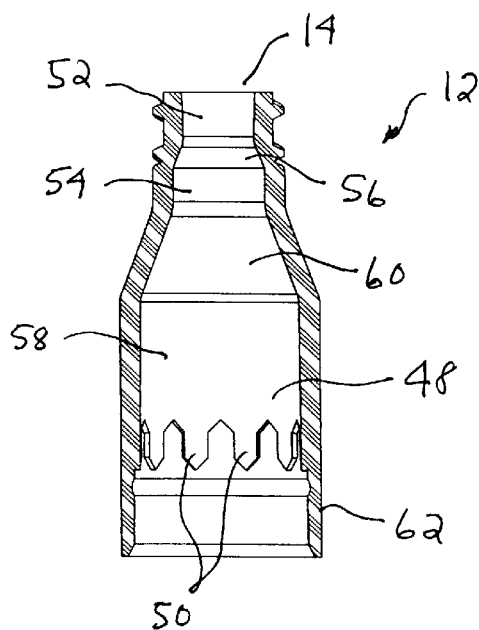
Figure 7C:
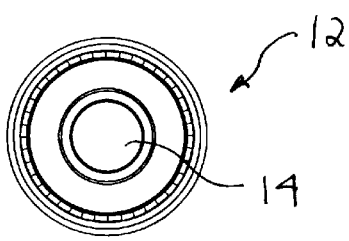

The exterior surface of the tubular housing 34 of the Luer-lock insert 16 is molded to include a crown shaped outer shell 44 which includes several crown points 46. As shown in FIG. 6, the interior of the valve body 12 is molded to include a crown shaped inner shell 48 which includes several crown points 50. The crowned tubular-housing outer shell 44 of the Luer-lock insert 16 mates with the crowned valve-body inner shell 48 of the valve body 12, thereby facilitating snap-fit assembly of the medical connector. Alternatively, the male Luer-lock insert 16 and valve body 12 may be joined by ultrasonic weld geometry, a spin weld, bonding, or by other means.

As is illustrated in FIGS. 7a–7d, the interior of the valve body 12 has sections of varying diameters. The section directly adjacent the inlet port 14 includes a standard ANSI Luer taper section 52 that incorporates a very slight inward taper. The center section 54 has a larger diameter than the taper section 52 and is separated from the taper section by the tapered ramp/lock section 56. The bottom section 58 has a larger diameter than the center section 54 and is separated from the center section by a taper section 60. Finally, the valve body 12 includes a skirt 62. The skirt 62 has an inside diameter that is dimensioned to fit over the male Luer-lock insert 16. The valve body 12 may be molded of a material containing a phosphorescent colorant to render the connector visible in a darkened room or may be formed of a transparent material.

Figure 8B:
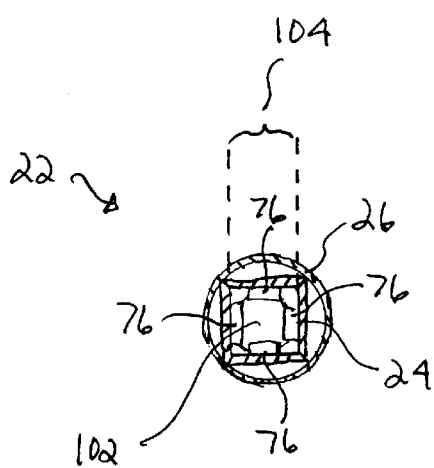
FIG. 8b is a top view of the flex-tube assembly shown in FIG. 8a taken along the line 8b—8b.
Figure 9B:
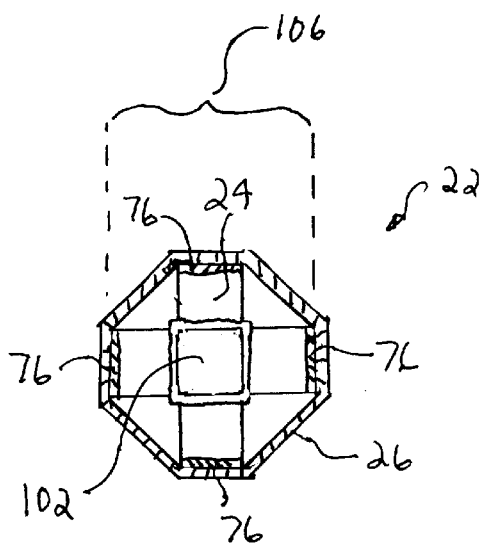
FIG. 9b is a top view of the flex-tube assembly shown in FIG. 9a taken along the line 9b—9b.
Figure 8A:
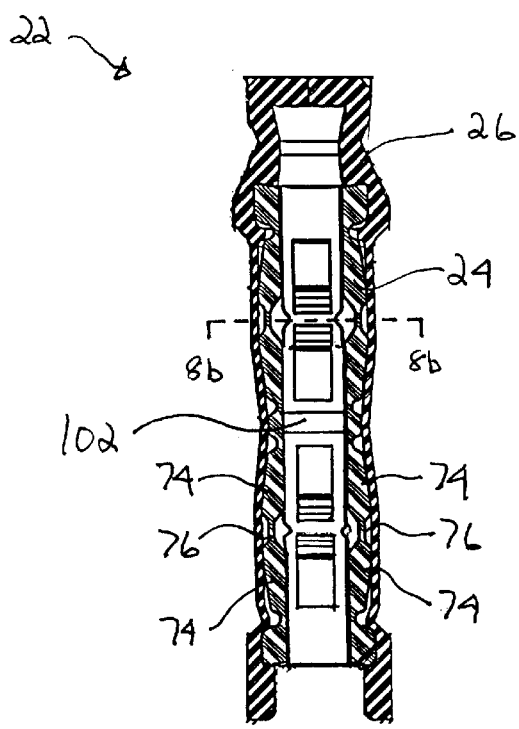
FIG. 8a is a full sectional view of the flex-tube assembly shown in FIGS. 2 and 3 depicted in an uncompressed state and showing the flex-tube insert positioned within the flex-tube piston.
Figure 9A:
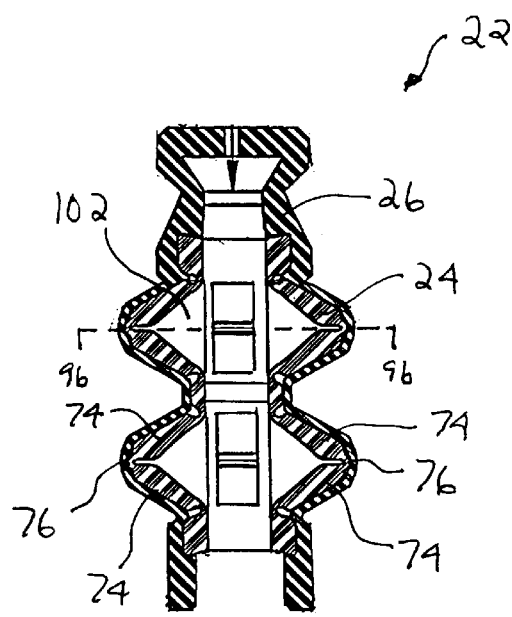
FIG. 9a is a full sectional view of the flex-tube assembly shown in FIGS. 2 and 3 depicted in a compressed state and showing the flex-tube insert positioned within the flex-tube piston.

As shown in FIGS. 8a and 9a, the resiliently deformable flex-tube assembly 22 includes the flex-tube insert 24 and the flex-tube piston 26. The flex-tube insert 24 is surrounded by the flex-tube piston 26. As is shown in FIG. 14, the flex-tube assembly 22 is captured in the groove 42 of the male Luer-lock insert 16 to form a tight seal about the support post 28 and the top of the male Luer taper 36. The flex-tube piston 26 includes an antimicrobial agent, such as silver, silver oxide or silver sulfadiazine. The agent may be included in the material forming the flex-tube piston or may be added to the outer surface of the piston as a coating. These agents reduce the incidence of infection if the valve is not properly disinfected with an alcohol wipe prior to use. The flex-tube insert 24, valve body 12 and/or male Luer-lock 16 insert may also include an antimicrobial agent. The peripheral surface of the flex-tube piston 26 is also lubricated with FDA approved silicone oil to facilitate movement of the flex-tube assembly within the connector.

Figure 10:
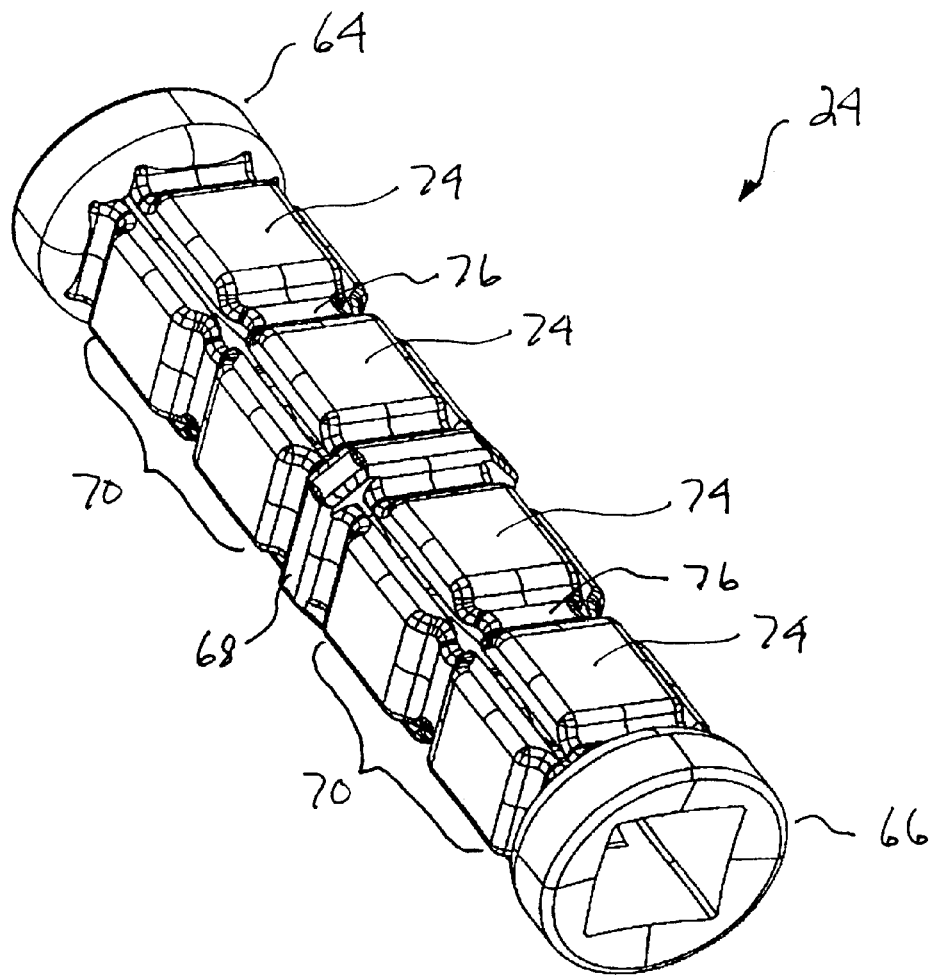
FIG. 10 is a perspective view of the flex-tube insert shown in FIGS. 2, 8a, 8b, 9a, and 9b.
Figures 11A, 11B:
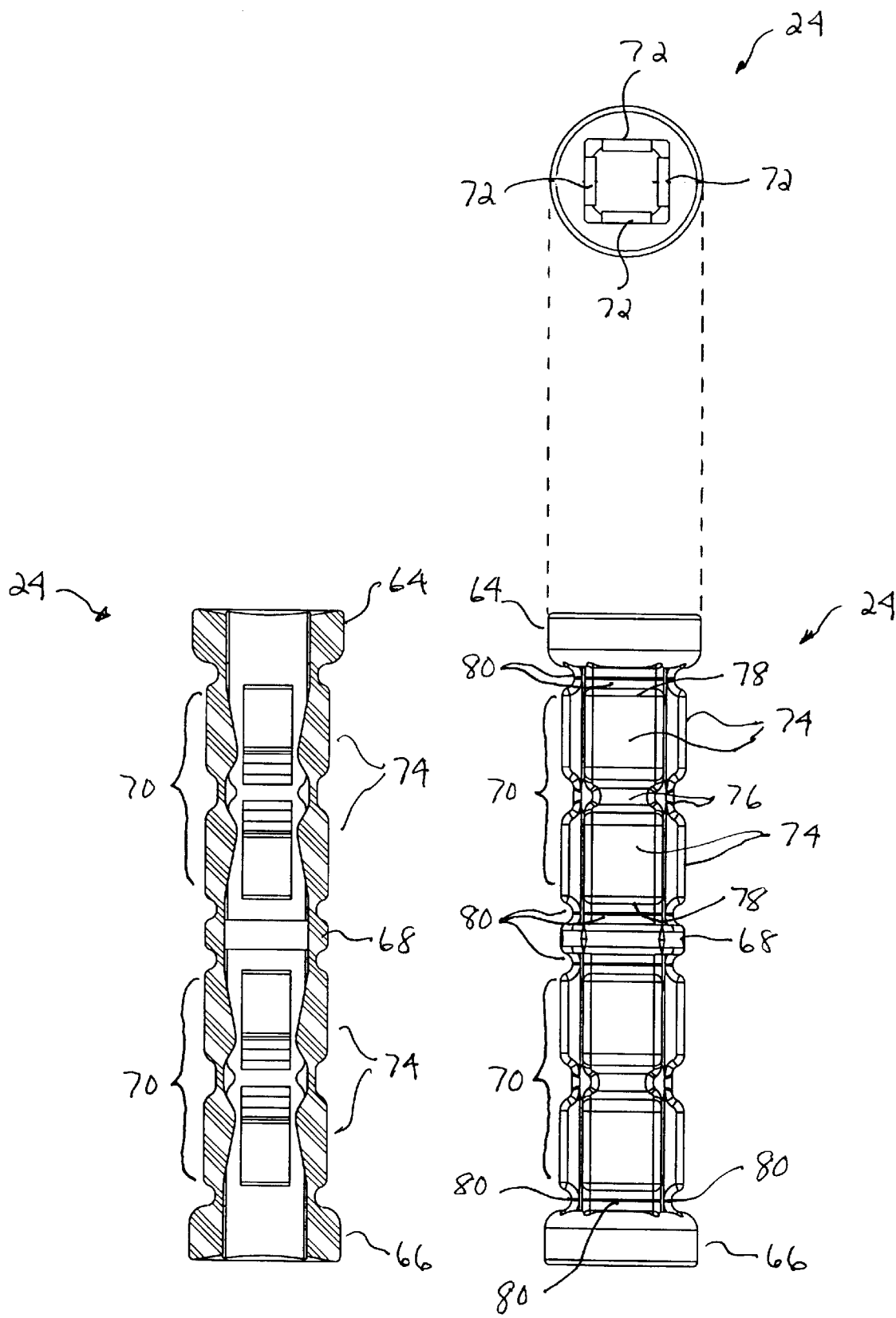
FIG. 11a is a side elevation view and a top view of the flex-tube insert shown in FIG. 10.
FIG. 11b is a full sectional view of the flex-tube insert shown in FIG. 10.

As shown in FIGS. 10–11b, the flex-tube insert 24 includes an annular inlet support 64, an annular outlet support 66 and a middle support 68. Positioned between adjacent supports is a collapsible section 70. Each collapsible section 70 includes four hinge assemblies 72 arranged in a square, as shown in FIG. 11a. Each hinge assembly 72 includes two plates 74 and a hinge 76 about which the plates pivot. As best shown in FIG. 11b, the inner surfaces of the plates 74 are sloped. As explained below, the sloped surfaces prevent the plates 74 from completely collapsing on each other. The edges 78 of the plates parallel with the hinge 76 are attached to one of the supports 64, 66, or 68. The connection between the edges 78 and the supports 64, 66, or 68 is facilitated by a support hinge 80. Operation of the flex-tube insert 24 is described below in conjunction with the flex-tube piston 26.

Figure 12:
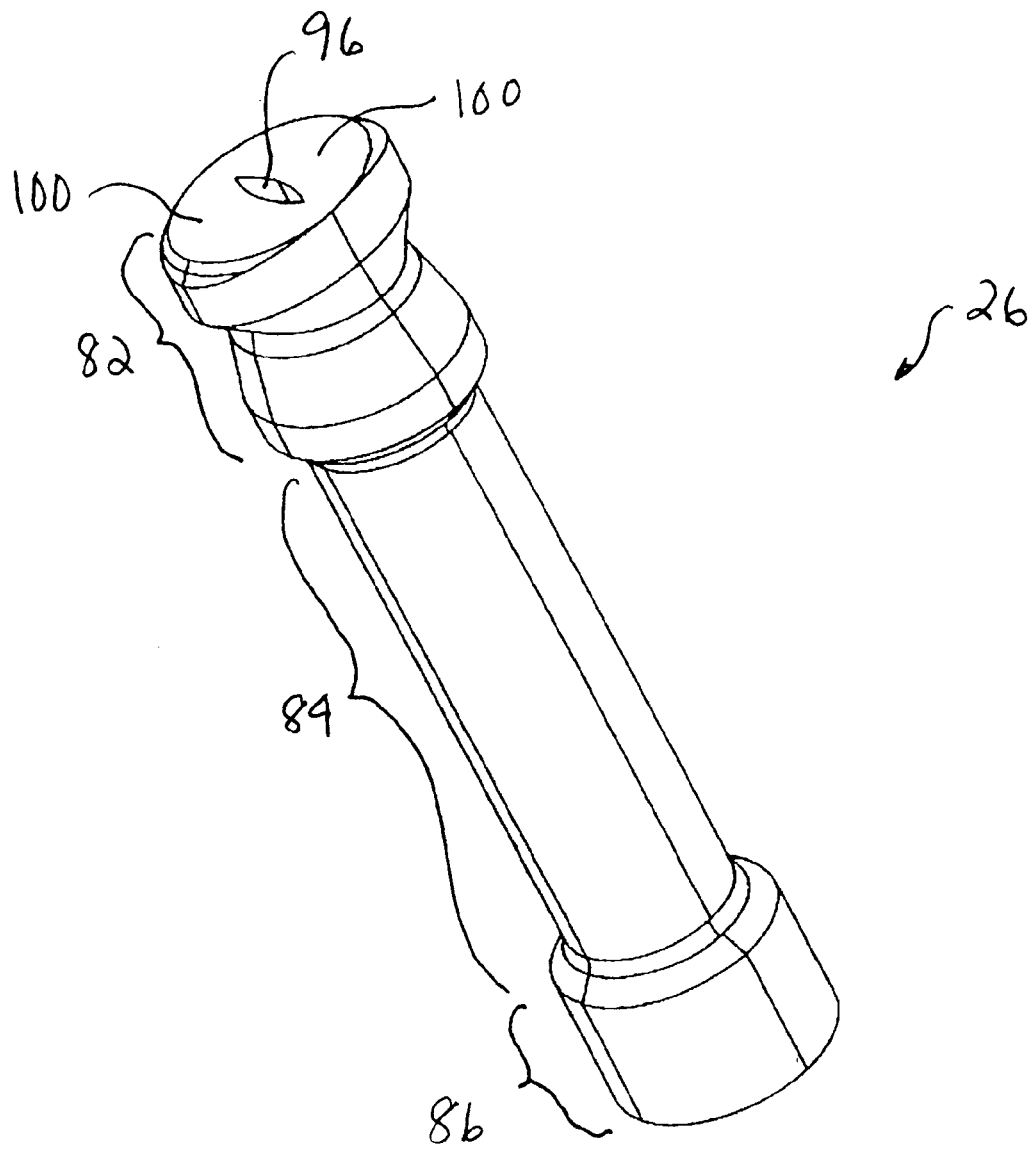
FIG. 12 is a perspective view of the flex-tube piston shown in FIGS. 2, 3, 8a and 8b.
Figures 13A, 13B:
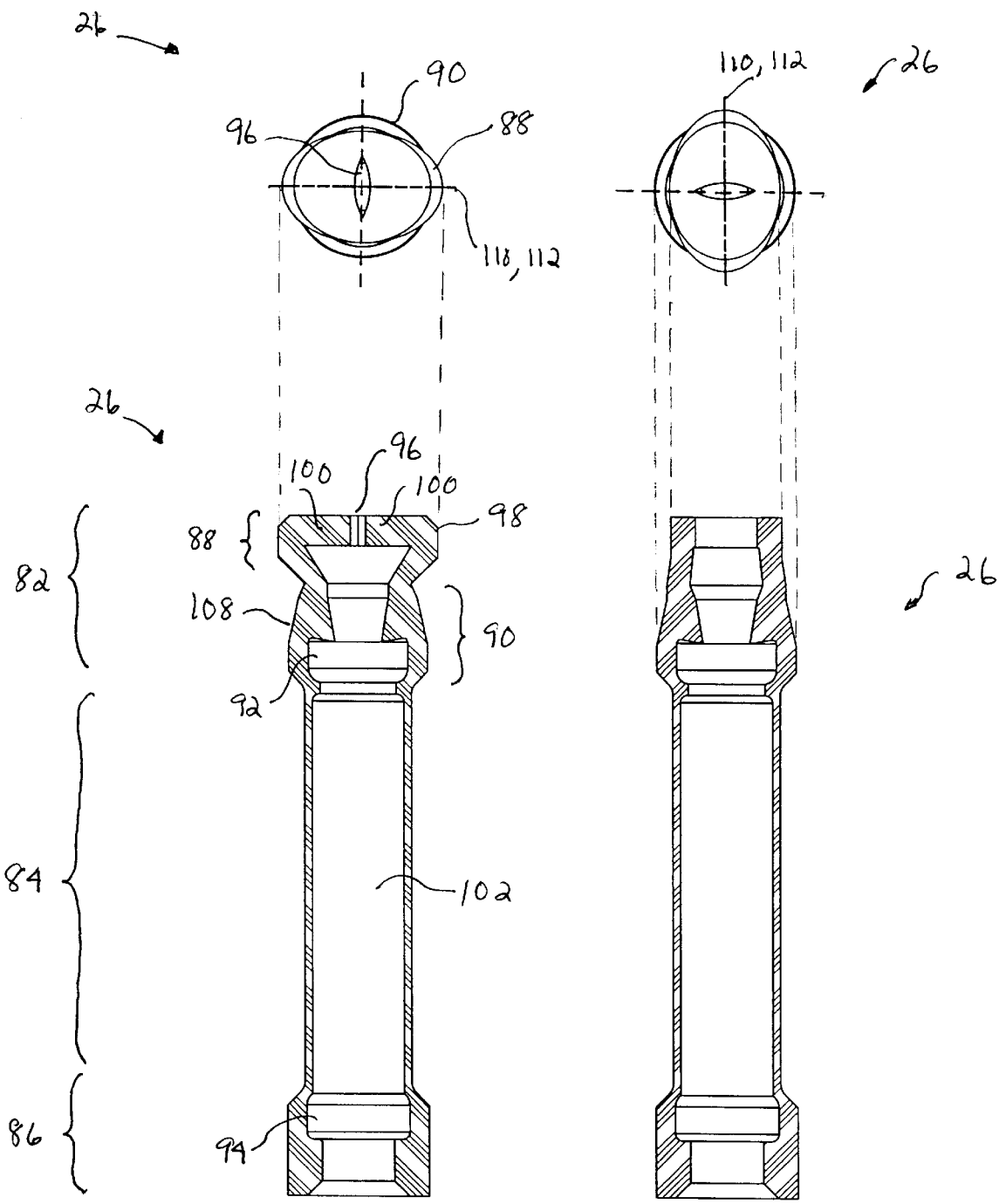
FIGS. 13a and 13b are first and second full sectional views and top views of the flex-tube piston shown in FIG. 12 with the views rotated 90 degrees from each other.
Figure 13A:
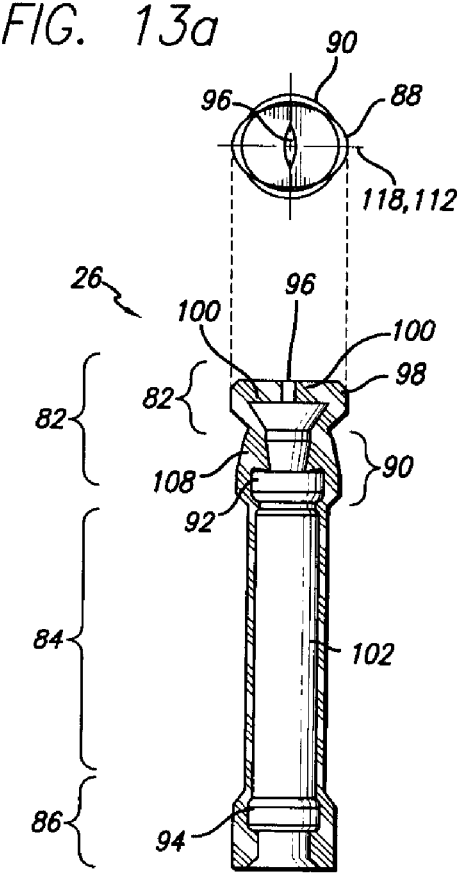
Figure 13B:
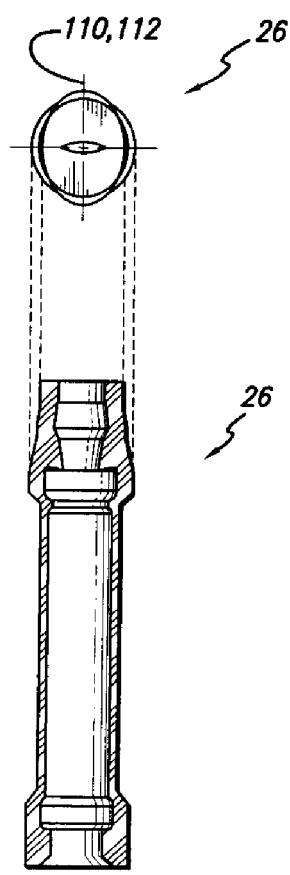
Figure 16:
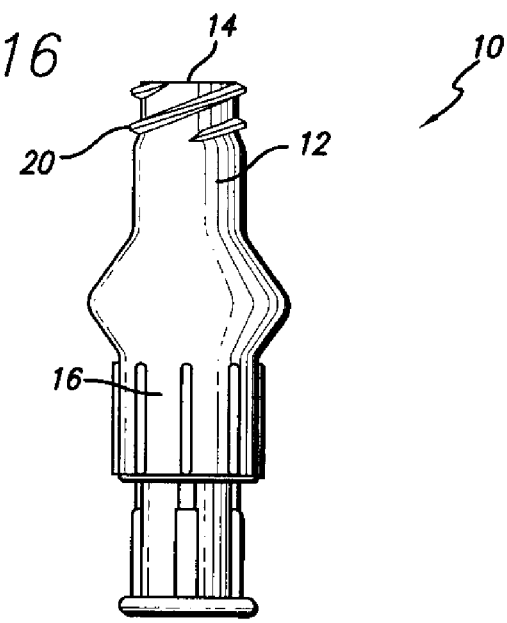
Figure 19:
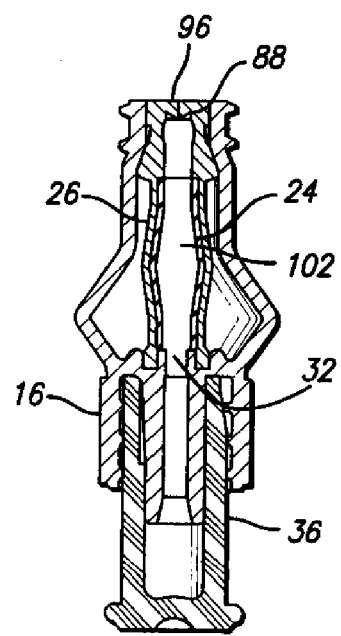
Figure 20:
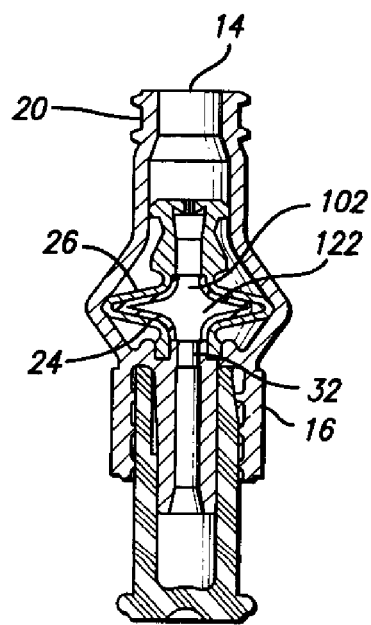
Figure 22B:
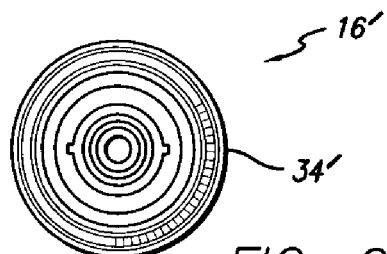
Figure 22A:
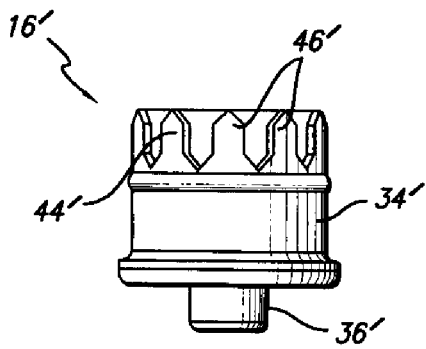
Figure 22D:
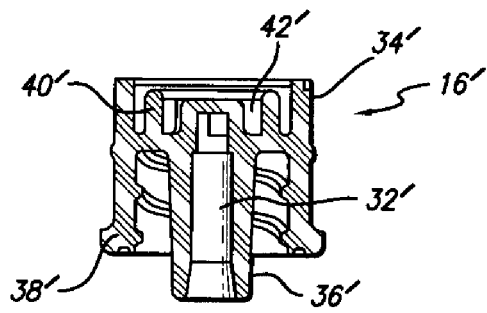
Figure 22C:
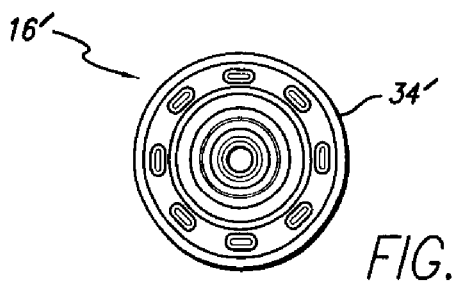
Figure 22B:
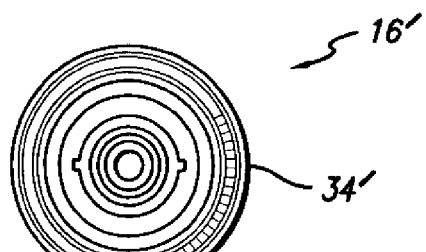
Figure 22A:
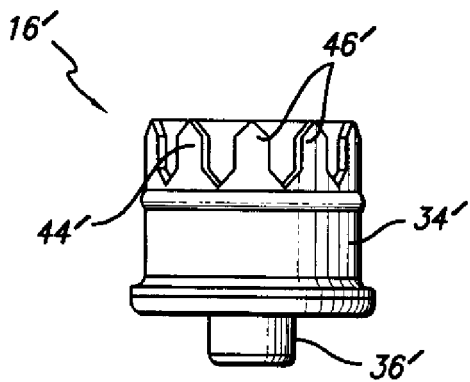
Figure 22D:
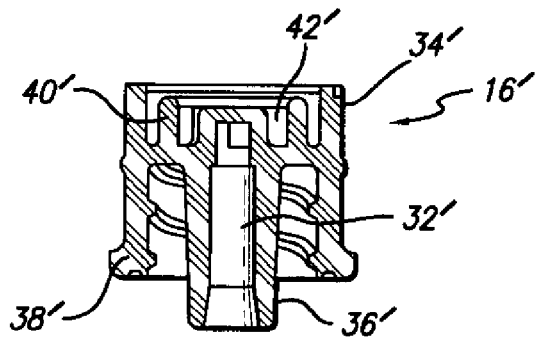
Figure 22C:
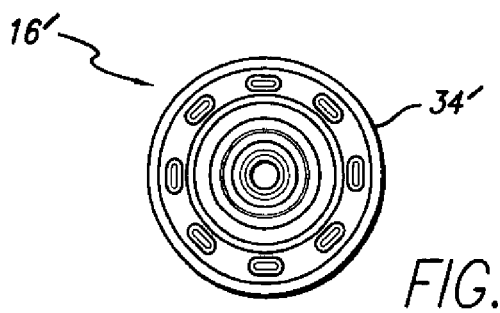
Figure 23:
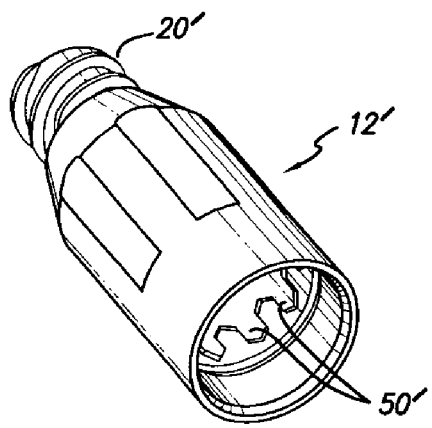
Figure 24B:
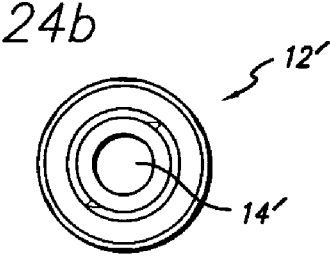
Figure 24A:
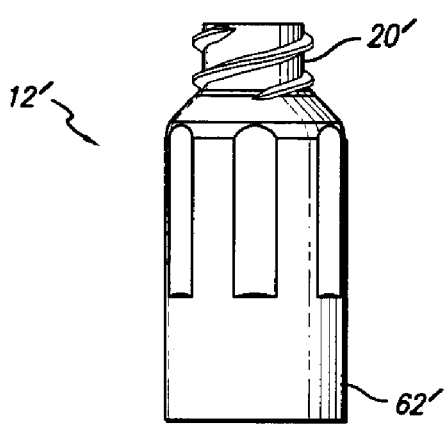
Figure 24D:
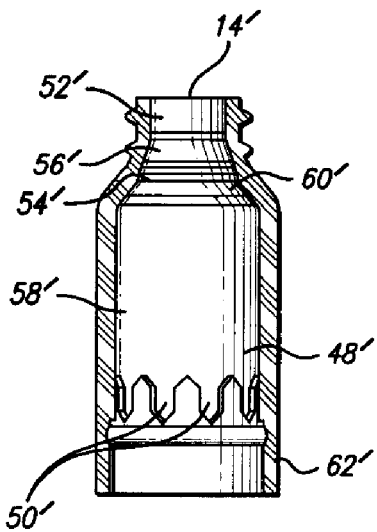
Figure 24C:
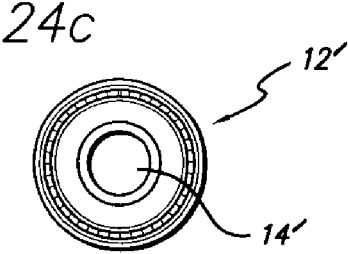
Figure 25A:
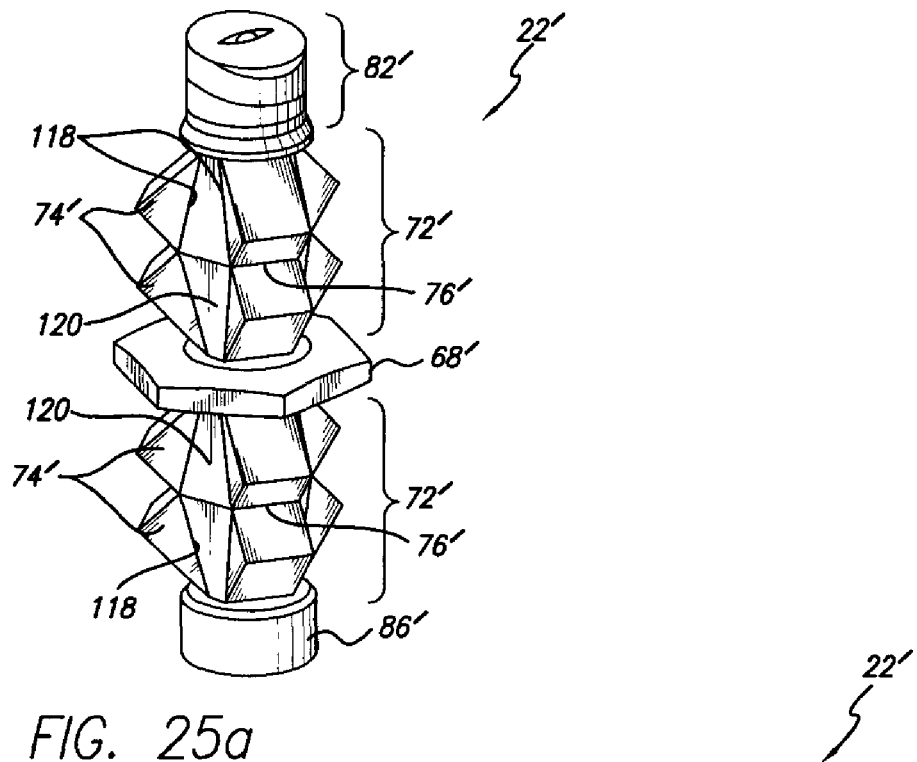
Figure 25B:
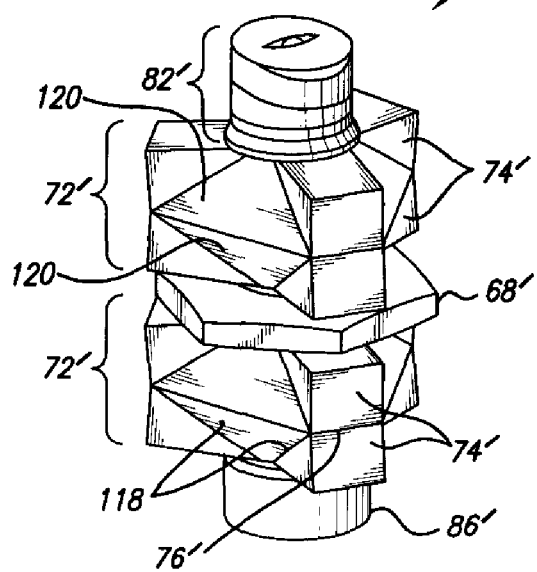
Figures 26A, 26B:
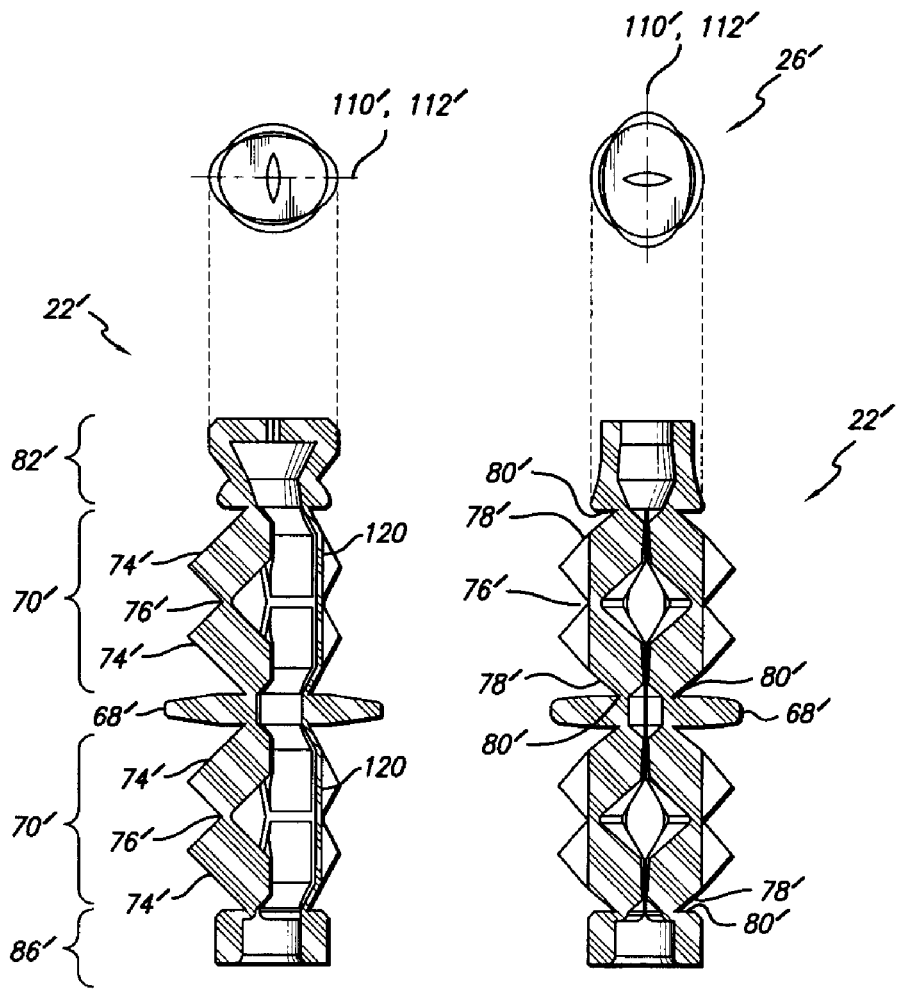
Figure 27B:
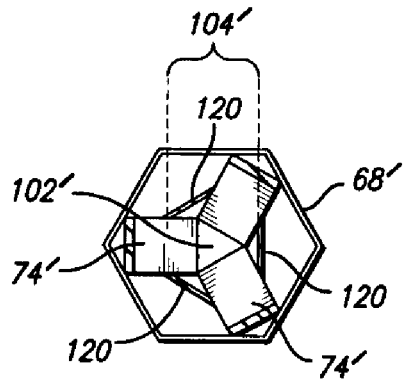
Figure 28B:
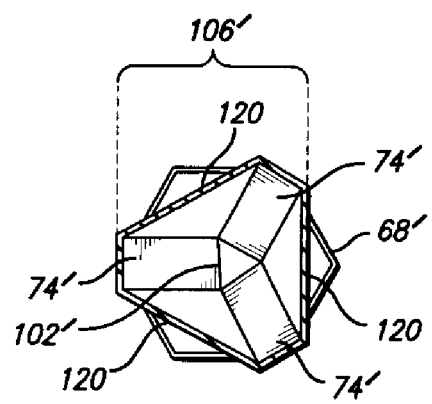
Figure 27A:
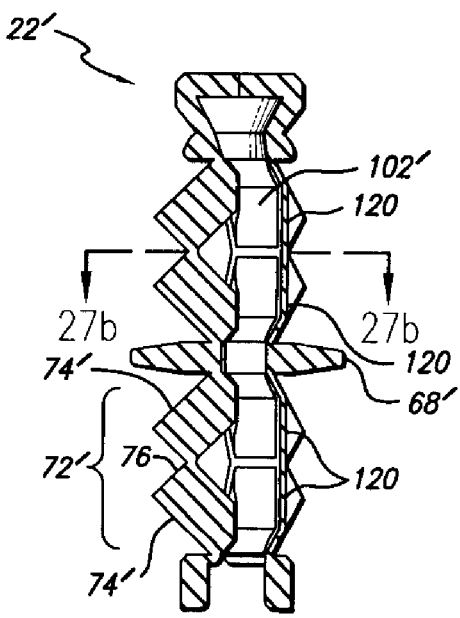
Figure 28A:
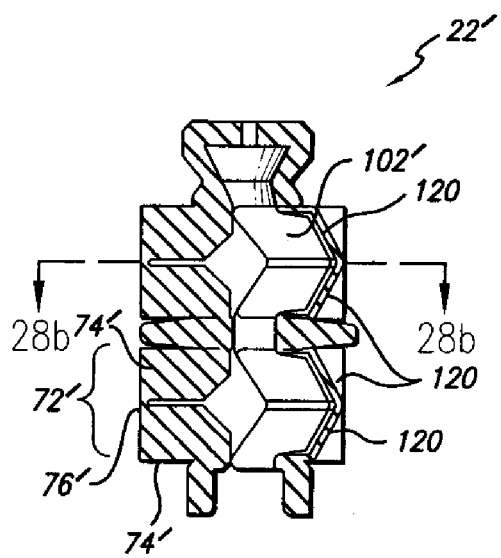
Figure 29:
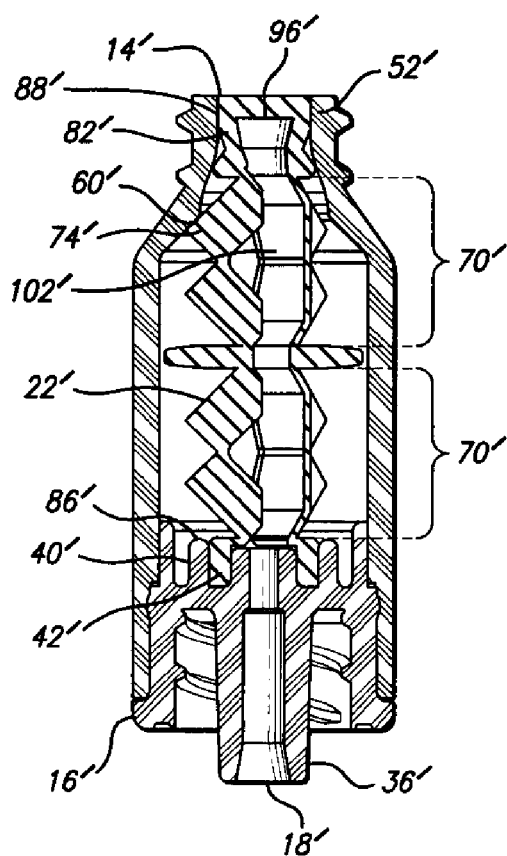
Figure 30:
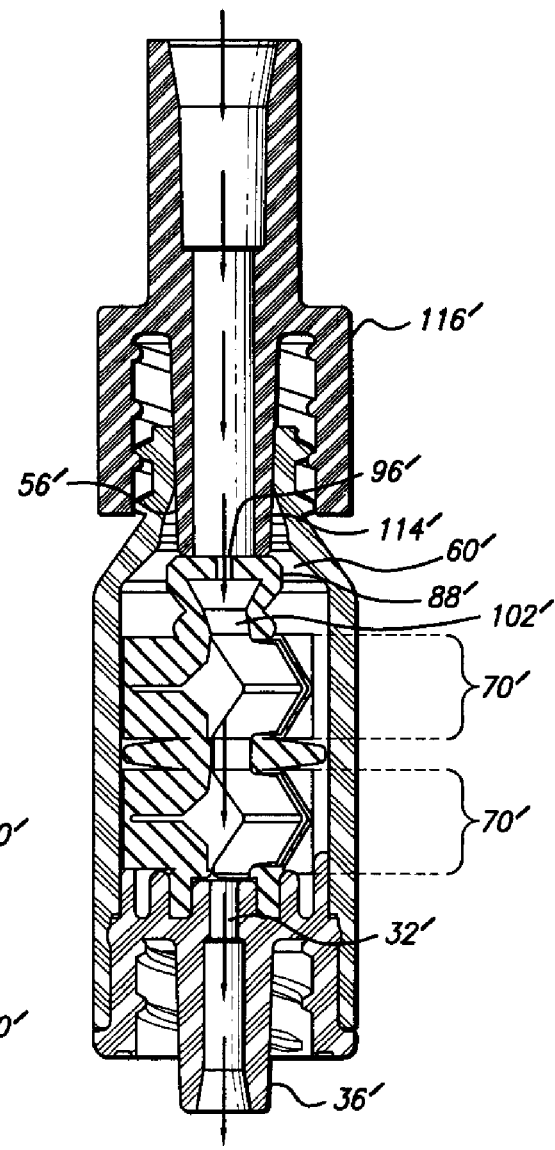
Figure 31:
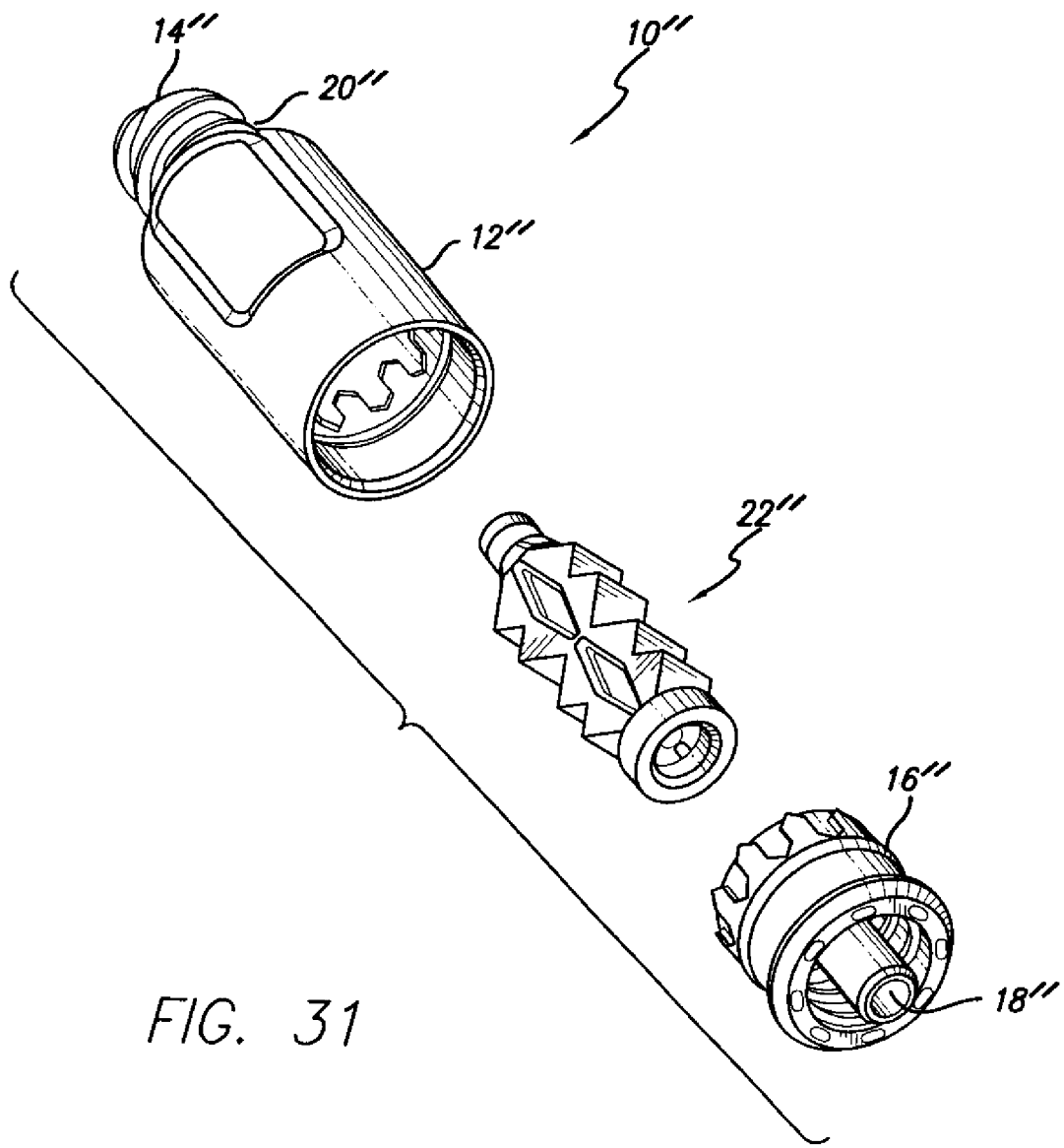
Figures 32, 33B:
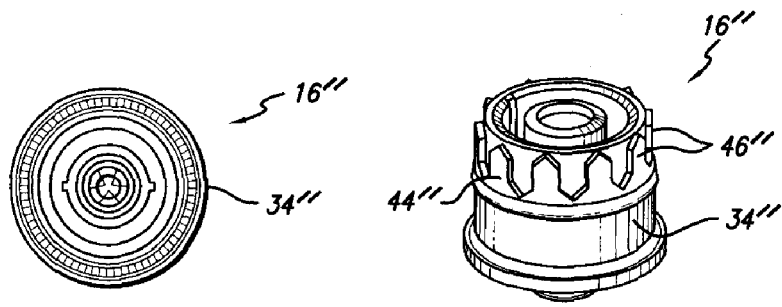
Figures 33A, 33C:
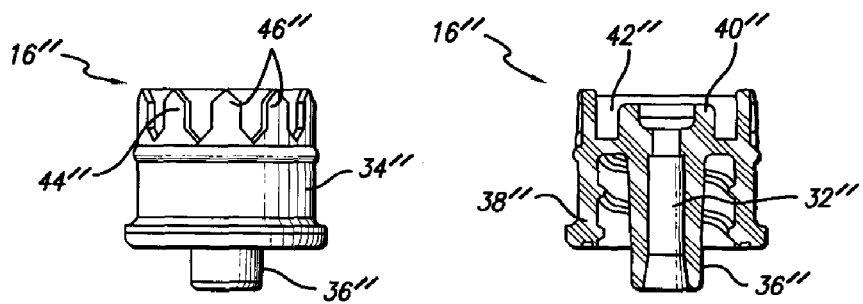
Figure 34:
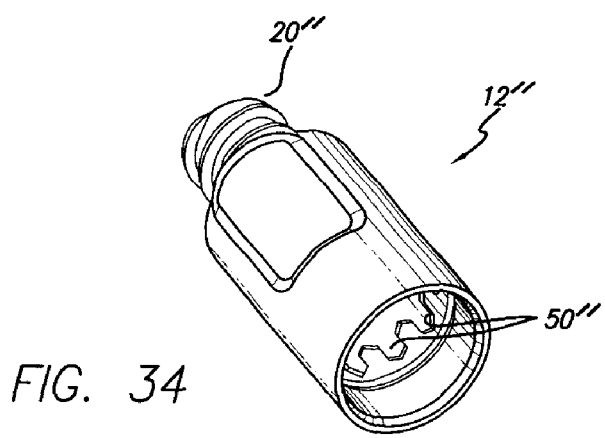
Figure 35B:
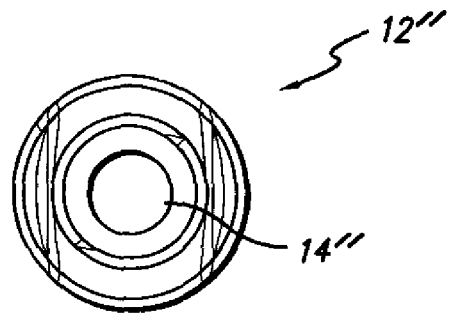
Figure 35A:
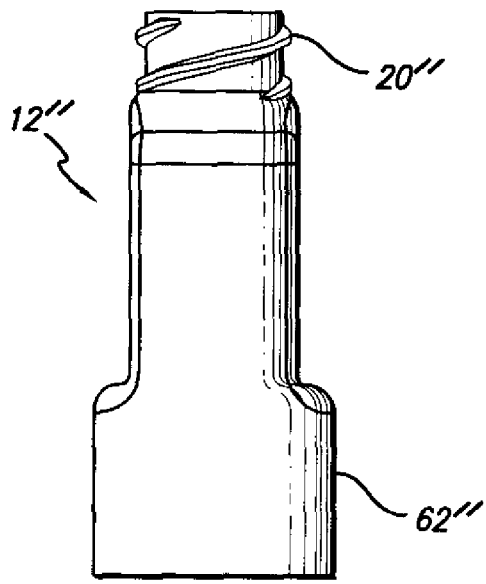
Figure 35C:
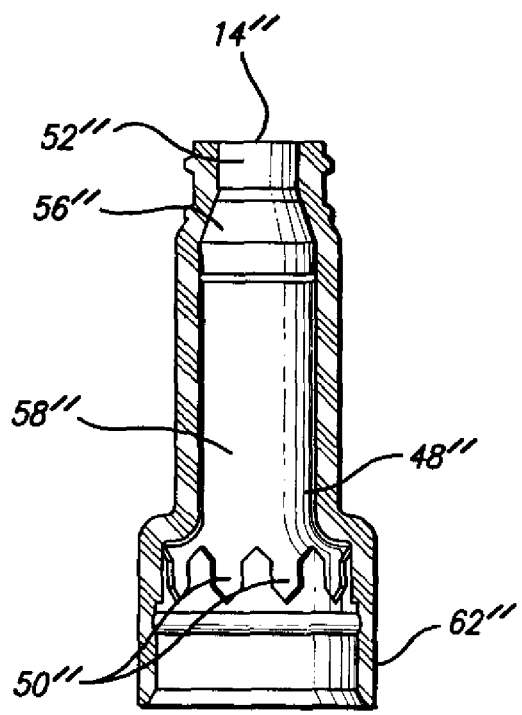
Figure 35D:
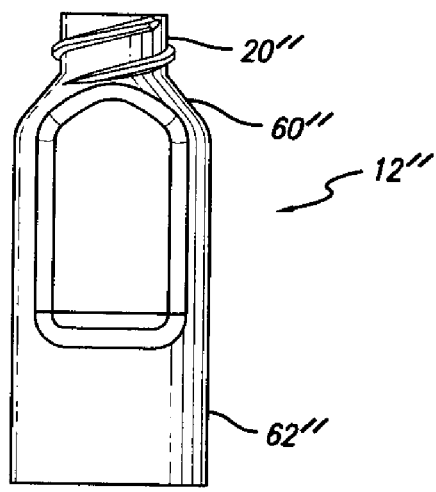
Figure 36:
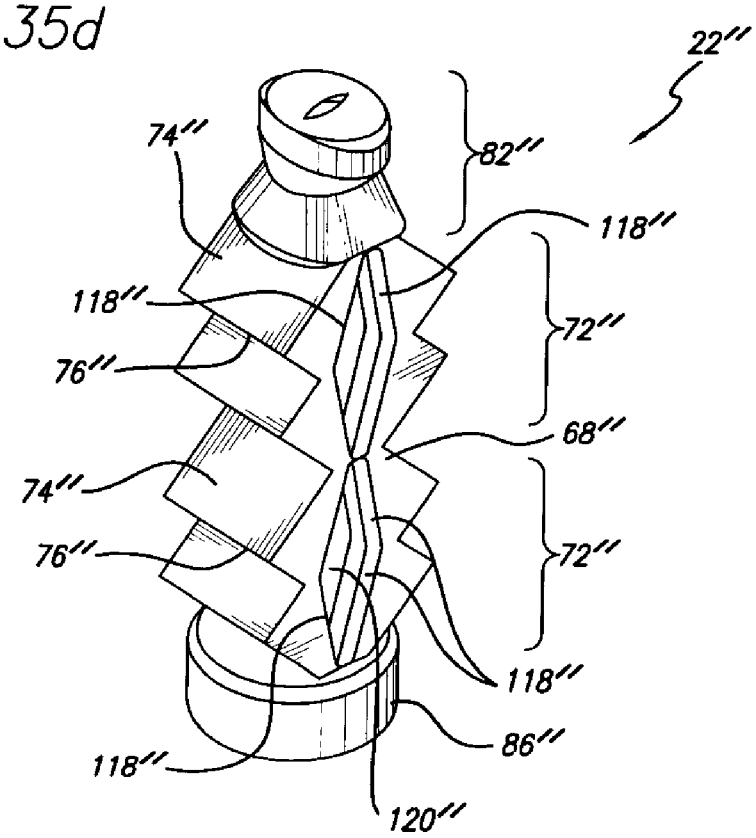

As shown in FIGS. 12–13b, the flex-tube piston 26 includes a piston head 82, an expandable section 84 and a piston base 86. The piston head 82 includes a top section 88 that is elliptical in cross-section and a bottom, thick taper-lock portion 90 that is circular in cross-section. The taper-lock portion 90 includes an annular groove 92 that is sized to receive and secure the annular inlet support (not shown) of the flex-tube insert 24. The base 86 of the flex-tube piston also includes an annular groove 94 that receives and secures the annular outlet support (not shown). A marquise-shaped bore 96 is formed in the piston head 82. The top portion 88 of the piston head 82 includes a lip seal 98 that comprises a pair of lips 100 that extend from opposed sides of the bore 96 to function as a seal. The bore 96, in conjunction with the hollow interior of the taper lock section 90 and the hollow interior of the expandable section 84, form a fluid path 102 through the flex-tube piston 26 The piston head 82 and bore 96 are configured closeup and function similarly to the piston head and bore described in U.S. Pat. No. 5,676,346, inventor Karl R. Leinsing, entitled NEEDLELESS CONNECTOR VALVE, and assigned to the same assignee of record of this application, the disclosure of which is hereby incorporated by reference.

Through proper selection of the dimensions of the hinge assemblies, the flex-tube insert 24 (FIG. 11a) is able to facilitate expansion of the fluid-flow path 102 (FIGS. 8a and 9a) of flex-tube piston 26 to either increase the volumetric capacity of the fluid flow path to provide a positive-bolus effect, or to maintain it at a substantially constant capacity to provide a no-bolus effect. If desired, the flex-tube assembly 22 may also be designed to provide a negative-bolus effect. The flex-tube piston 26, in turn, is designed to provide a restoring force to the flex-tube insert 24 (FIG. 11a) to return the fluid-flow path 102 to a nonexpanded condition and thus return the volumetric capacity of the fluid flow path to its original value. To facilitate operation of the flex-tube assembly 22, the flex-tube piston 26 is molded of a resilient flexible rubber material such as silicone, while the flex-tube insert 24 is formed of a more rigid material, such as material polyethylene.

As shown in FIGS. 8a and 8b, the flex-tube assembly 22 is movable between an uncompressed state (FIG. 8a) and a compressed state (FIG. 8b). In the uncompressed state the flex-tube insert 24 has a first maximum width 104, as shown in FIG. 8b, and the fluid path 102 defined by the flex-tube piston 26 has a first internal volume. In the compressed state the flex-tube insert 24 has a second maximum width 106 greater than the first maximum width 104, as shown in FIG. 9b, and the fluid path 102 defined by the flex-tube piston 26 has a second internal volume greater than or substantially equal to the first internal volume. As mentioned above, when the second internal volume is greater than the first internal volume a positive-bolus effect is provided. When the second internal volume is substantially equal to the first internal volume a no-bolus effect is provided.

The interplay between the flex-tube insert 24 and the flex-tube piston 26 facilitate the movement between the uncompressed and compressed states. The flex-tube insert 24 is instrumental in establishing the compressed state. Upon the application of downward force to the flex-tube assembly 22, opposed hinges 76 of the flex-tube insert 24 move away from each other and the respective plates 74 attached to these hinges collapse toward each other. The sloped inner surfaces of the plates 74 limit the movement of the hinges and prevent the plates from completely collapsing on each other. As the plates 74 collapse, the maximum cross section of the flex-tube insert 24 increases and the expandible section 84 (FIG. 13*a*) of the flex-tube piston 26 stretches. For a positive-bolus connector this increases the internal volume of the fluid path 102 toward a second internal volume greater than the first internal volume. When the application of downward force is removed, the resiliency of the expandable section 84 forces the opposed hinges 76 toward each other and the plates 74 apart. Thus the flex-tube assembly 22 returns to its original uncompressed state and, for a positive-bolus connector, the internal volume of the fluid path 102 decreases toward the first internal volume. For a no-bolus connector, the internal volume remains substantially constant as the flex-tube assembly 22 moves between compressed and uncompressed states.

Turning now to a more detailed description of the operation of the medical connector, with reference to FIGS. 14 and 15, the dimensions of the top portion 88 of the piston head 82 and the marquise-shaped bore 96 are selected such that when the top portion is constrained within the circular interior of the ANSI Luer taper section 52 the bore 96 is completely collapsed to tightly close off the orifice and cause the adjacent lips 100 to abut one another. The tapered shoulder 108 of the taper lock section 90 contacts the ramp/lock section 56 of the valve body 12 and prevents the top portion 88 of the piston head 82 from extending beyond the inlet port 14. The internal diameter of the center section 54 of the valve body 12 is selected such that the top portion 88 of the piston head 82 is free to assume its elliptical shape when positioned therein. This, in turn, allows the bore 96 to reassume its natural marquise-shape thereby opening the fluid path 102 through the flex-tube assembly 22.

In operation of a positive-bolus medical connector, the connector 10 is initially in its unaccessed state or closed position as shown in FIG. 14. The resiliency of the expandable section 84 of the flex-tube piston 26 causes the piston head 82 to be biased into the ANSI Luer taper section 52. The shoulder 108 of the flex-tube piston 26 contacts the tapered ramp/lock section 56 of the valve body 12 and prevents the top of the piston head 82 from extending beyond the edge of the inlet port 14 to form a smooth and flush surface. The bore 96 through the piston head 82 is tightly squeezed shut by virtue of the normally elliptically shaped top portion 88 of the piston head being constrained into the circular cross-section of the ANSI Luer taper section 52. The sharp pointed ends of the marquise-shaped bore 96 facilitate a tight seal upon compression of the bore along its minor axis 110 (FIG. 13*b*) and by compression of the top portion 88 of the piston head 82 along its major axis 112.

Just prior to accessing the connector, the top surface of the piston head 82 and the edge of the inlet port 14 are cleaned by, for example, passing a sterilizing swipe over the smooth surface. The absence of ridges, grooves, gaps, or protrusions ensure that proper cleanliness is achieved. The connector is then ready to be accessed by a standard male Luer with or without a Luer lock. With reference to FIG. 15, as the male Luer tip 114 of a male Luer connector 116 is brought into contact with the top surface of the piston head 82, a seal is formed to preclude the passage of liquid or air therebetween. The application of sufficient pressure causes the collapsible sections 70 of the flex-tube insert 24 to collapse about the support post 28 and the expandable section 84 of the flex-tube piston 26 to expand. The support post 28 serves to prevent the flex-tube insert 24 from buckling and closing off the fluid path. As the flex-tube assembly 22 compresses, the piston head 82 moves out of the ANSI Luer taper section 52 and into the center section 54. As the piston head 82 clears the tapered ramp/stop section 56 and is moved into the center section 54, the larger internal diameter of the center section 54 allows the top portion 88 of the piston head to assume its naturally elliptical open shape. This, in turn, allows the bore 96 to assume its natural marquise-shape thereby opening a fluid path through the piston head. Continued pressure by the male Luer tip 114 causes the bottom of the piston head 82 to communicate with the top of the support post 28. Fluid flows through the bore 96, into the hollow interior of the piston head 82, along the channels 30 formed on the outside of the support post 28 into the expanded areas 122 of the fluid flow path 102 and then into the tubular-housing fluid path 32.

As previously mentioned, as the flex-tube assembly 22 compresses it expands and the fluid capacity of the fluid path 102 increases, thus the volume of fluid within the connector is greater during activation of the valve. Because the internal volume increases during actuation, thereby producing a partial vacuum, fluid may be drawn toward the outlet port of the connector, for example blood from a patient may be drawn into an IV line. The drawing of fluid at this time is beneficial in that it provides a patency check of the IV line and ensures that infusion may proceed.

As the male Luer is withdrawn, the restoring force generated by the expandable section 84 of the flex-tube piston 26 causes the collapsed sections 70 of the flex-tube insert 24 to return to a noncollapsed state (FIG. 14) and the fluid capacity of the fluid path 102 decreases. Simultaneously, the elliptical top portion 88 of the piston head 82 is guided into the ANSI Luer taper section 52 by the tapered ramp/lock section 56 where it is once again forced into the constrained circular shape of the ANSI Luer taper section to close off the bore 96 and reestablish a positive seal. As the internal fluid capacity of the flex-tube assembly 22 decreases, the fluid contained therein is displaced. Because the bore 96 has established a positive seal at the inlet port 14, the fluid is displaced toward the outlet port 18. The positive displacement of fluid toward and out the outlet port 18 prevents a negative-bolus effect. Essentially the change from an increased fluid volume capacity during valve activation to a reduced fluid volume capacity during valve deactivation provides a positive-bolus effect in which a bolus of fluid is actually expelled from the connector 10 into the fluid line to the patient.

Figure 15A:
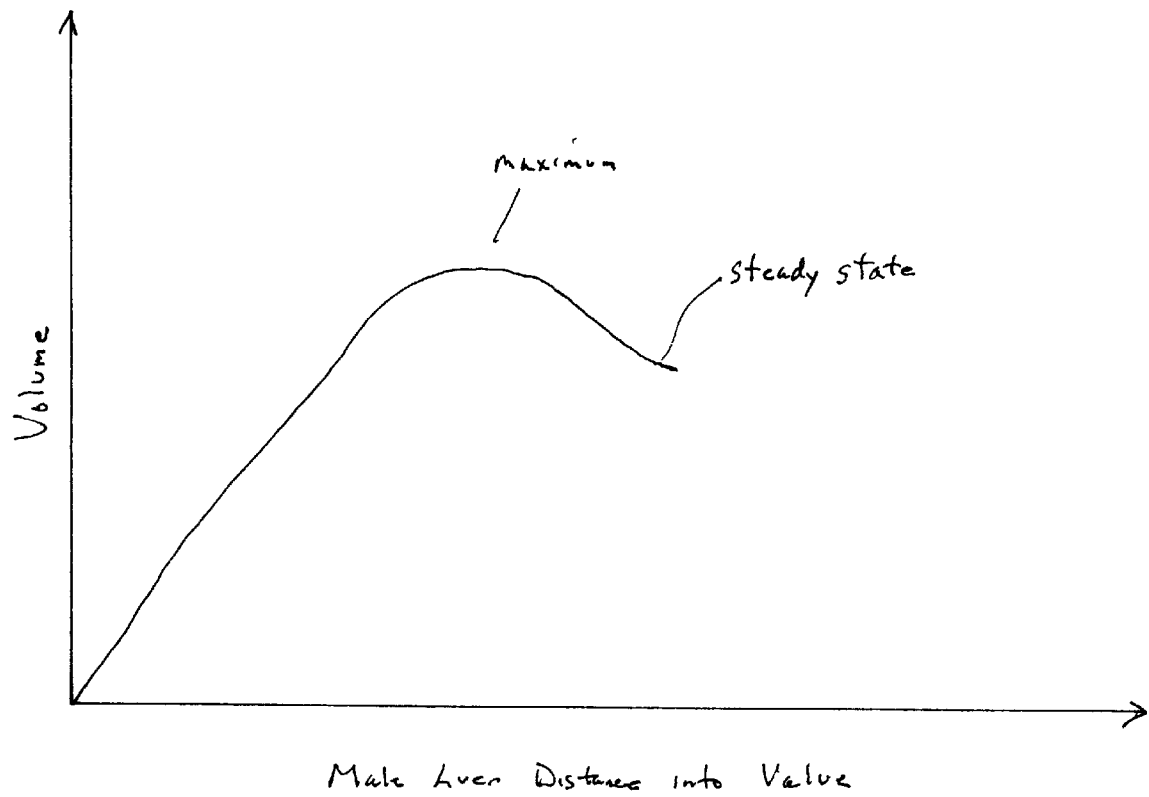
FIG. 15a is a graph depicting the volume of fluid within the flex-tube assembly as a function of the depth of insertion of a blunt or needle-free cannula into a medical connector providing a positive-bolus effect.

It is noted that the volumetric increase of the fluid path 102 during depression of the flex-tube assembly 22 is dependent on the depth to which the male Luer tip 114 is inserted into the inlet port 14. As shown in FIG. 15*a*, as the depth of the male Luer tip increases the volumetric capacity of the fluid path increases. At a certain depth of the male Luer tip the volumetric capacity of the fluid path reaches a maximum value, beyond which the capacity begins to decrease toward a steady state. This steady state point is reached when the male Luer tip is at its maximum depth. In one embodiment of the just-described configuration of the flex-tube assembly 22, the flex-tube assembly is dimensioned such that the volumetric capacity of the fluid path 102 during deactuation, i.e., the priming volume, is approximately 0.089 milliliters (ml.). The maximum volumetric capacity during actuation is approximately 0.099 ml.

Figure 18B:
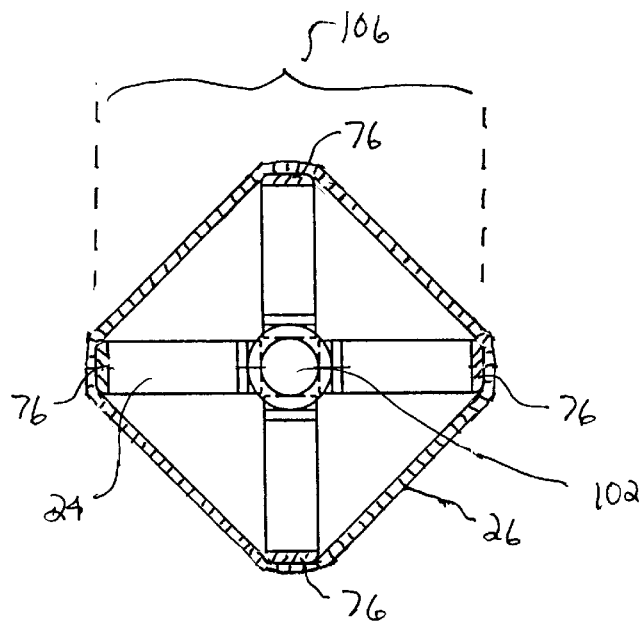
FIG. 18b is a top view of the flex-tube assembly shown in FIG. 18a taken along the line 18b—18b.
Figure 17A:
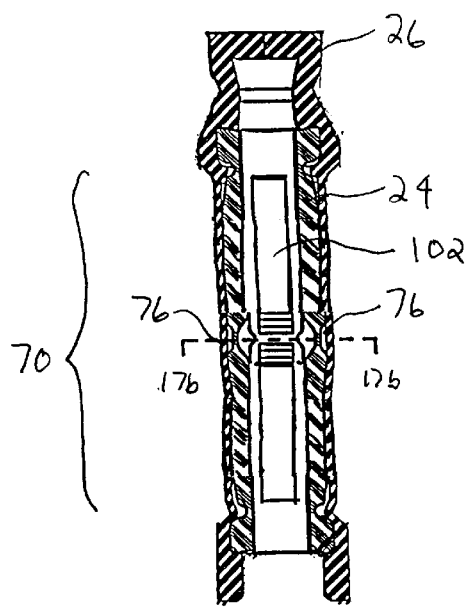
FIG. 17a is a full sectional view of a flex-tube assembly incorporated in the connector shown in FIG. 16 depicted in an uncompressed state and showing the flex-tube insert positioned within and surrounded by the flex-tube piston.
Figure 18A:
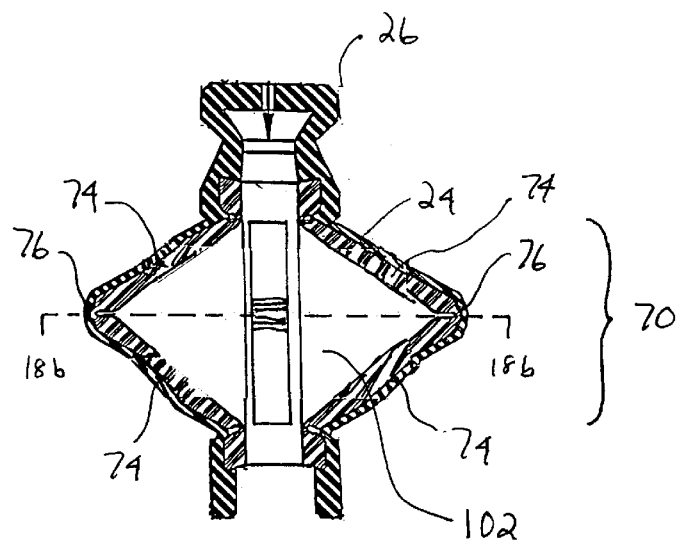
FIG. 18a is a full sectional view of the flex-tube assembly incorporated in the connector shown in FIG. 16 depicted in a compressed state and showing the flex-tube insert positioned within and surrounded by the flex-tube piston.

In the above-described flex-tube assembly 22, the flex-tube insert 24 includes two compressible sections 70. In alternate embodiments, the flex-tube insert 24 may comprise more or fewer compressible sections 70. For example, in the connector shown in FIGS. 16–20, the flex-tube insert 24 has only one compressible section 70. In this connector, the valve body 12 and male Luer-lock insert 16 are reconfigured to accommodate the increased second maximum cross section 106 of the flex-tube insert, as shown in FIG. 18b. Other then this difference, the remaining configurational and operational aspects of the connectors, including the operation of the connectors, are substantially identical.

With reference to FIG. 21 there is shown another configuration of a medical connector which incorporates aspects of the invention. Except for the flex-tube assembly, this configuration of the connector is generally similar to the connector of FIG. 1. Accordingly, the description of this connector primarily centers around the flex-tube assembly. For ease in correlating the two configurations, the numerals associated with elements of the second configuration are the same as those of the first configuration except they are primed. For numerals that are not primed there is no correlating element in the first configuration.

Figure 21A:
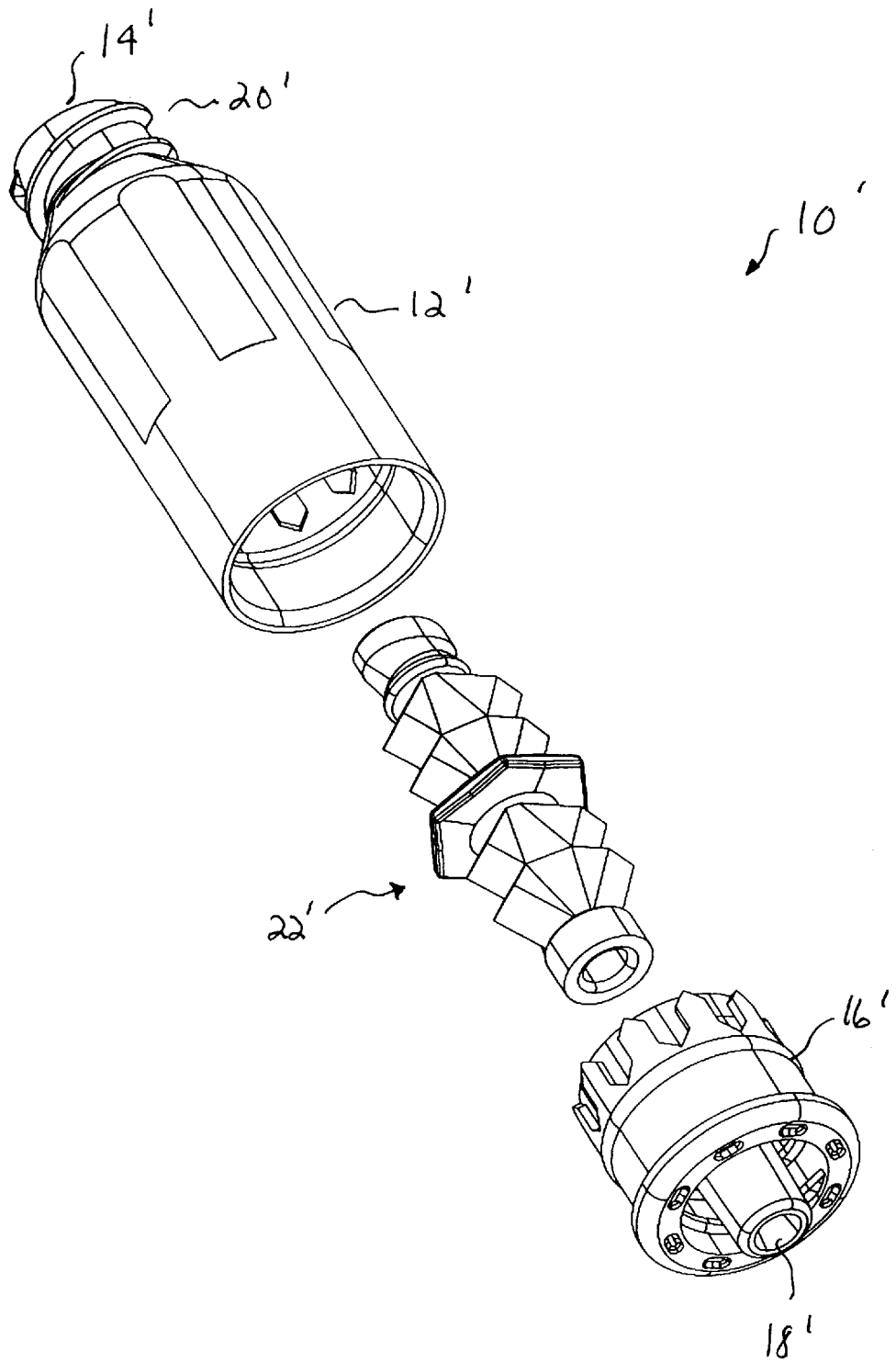
FIG. 21a is an exploded perspective view of the medical connector shown in FIG. 21 depicting a valve body, a male Luer lock insert, and a one-piece flex-tube assembly, i.e., valve assembly.
Figure 22B:
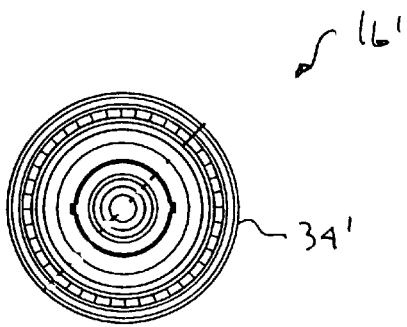
FIGS. 22a–22d depict various views of the male Luer-lock insert shown in FIG. 21 including a side elevation view, a top plan view, a bottom plan view and a full sectional view.
Figure 22A:
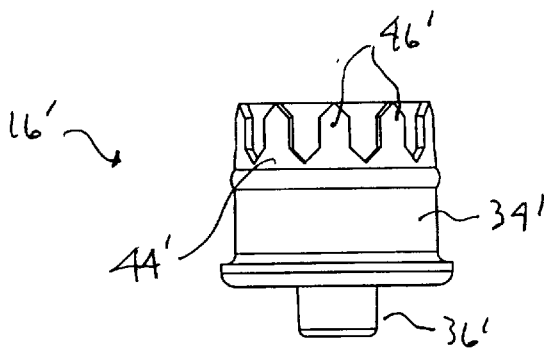
Figure 22D:
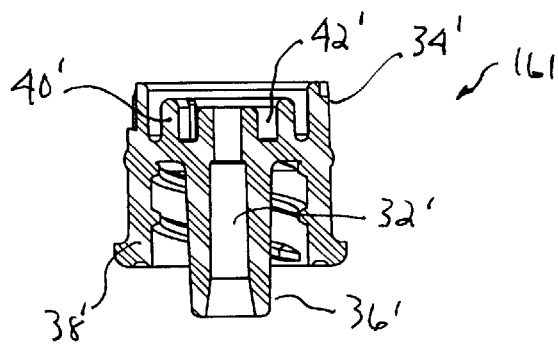
Figure 22C:
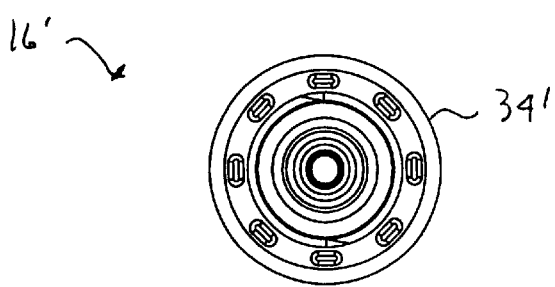
Figure 23:
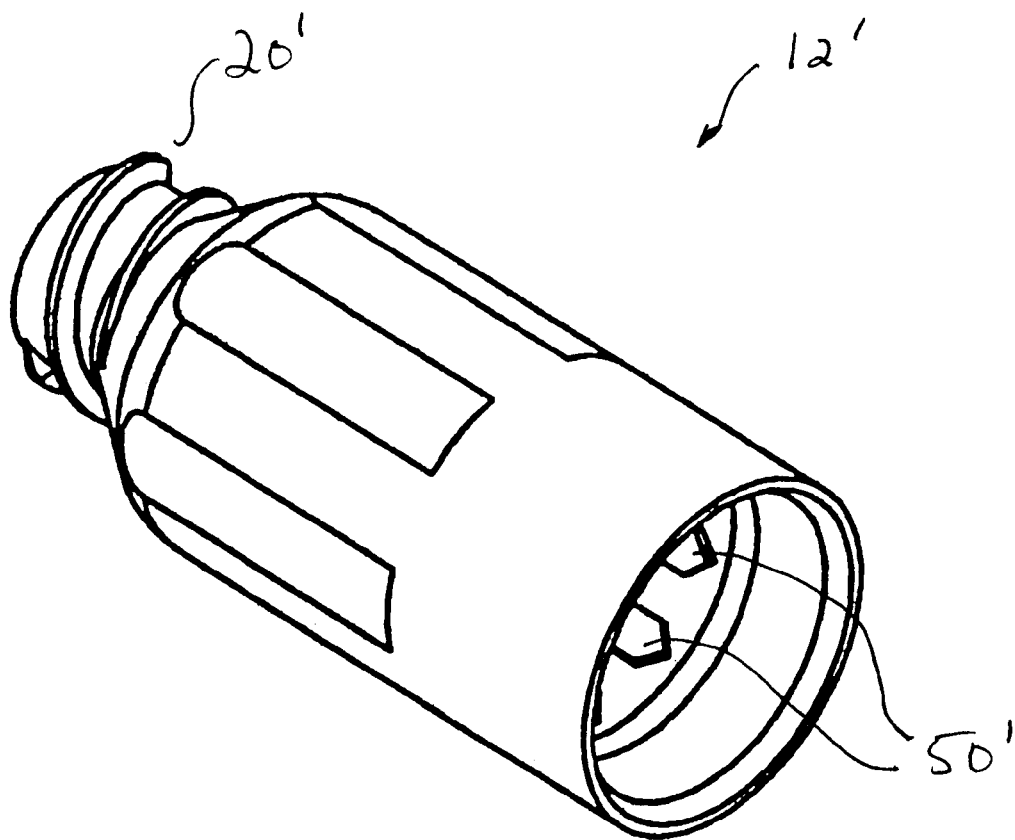
FIG. 23 is a perspective view of the valve body shown in FIG. 21.
Figure 24B:
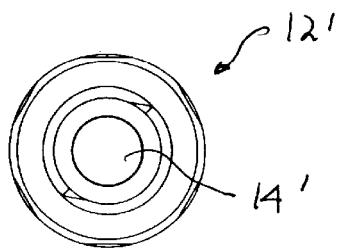
FIGS. 24a–24d depict various views of the valve body shown in FIG. 23 including a side elevation view, a top plan view, a bottom plan view and a full sectional view.
Figure 24A:
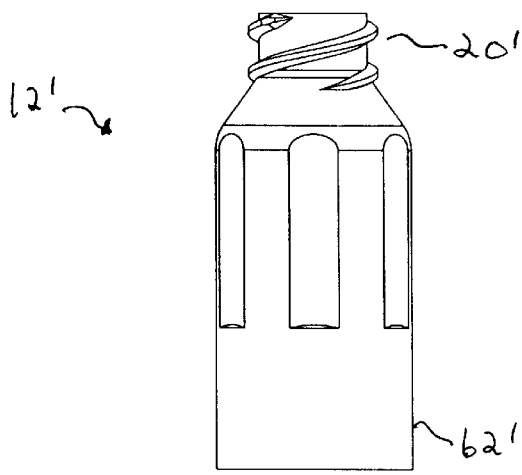
Figure 24D:
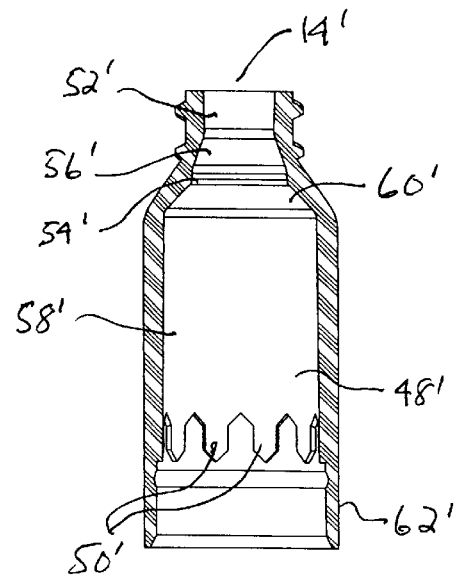
Figure 24C:
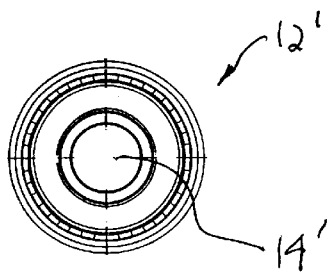
Figure 25A:
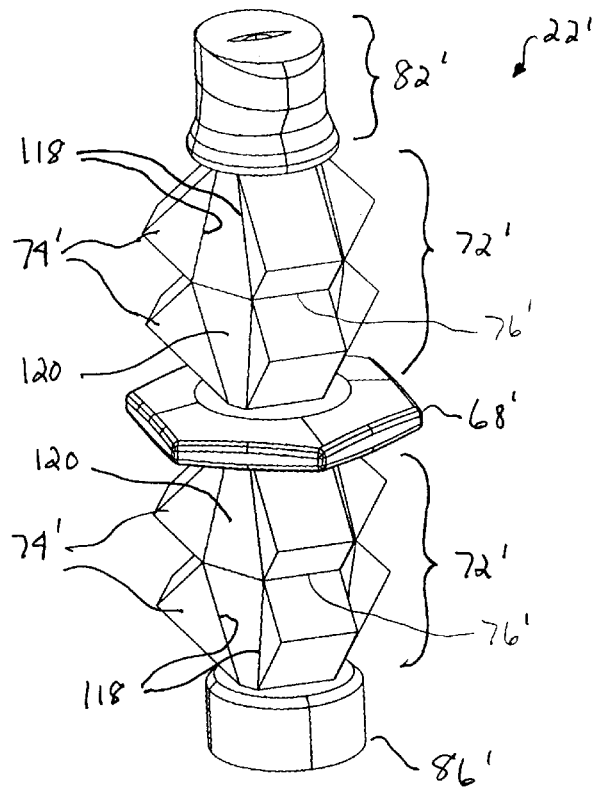
FIGS. 25a and 25b are perspective views of the flex-tube assembly housed within the medical connector shown in FIG. 21.
Figure 25B:
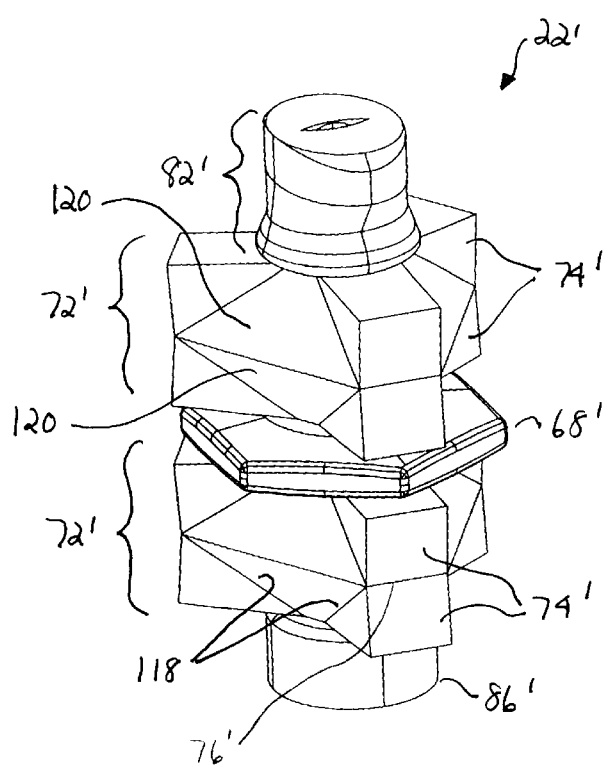

As shown in FIG. 21a, the connector 10' comprises a valve body 12', a male Luer-lock insert 16' and a flex-tube assembly 22'. As shown in FIGS. 22a–22d, the male Luer-lock insert 16' is substantially identical to the male Luer-lock insert 16 (FIG. 5a) of the first configuration, except there is no support post 28. As shown in FIG. 23, the valve body 12' is also substantially similar to the first configuration except that the tapered section 60', as shown in FIG. 24a–24d, is slightly different to accommodate for the different design of the flex-tube assembly 22'.

Figure 27B:
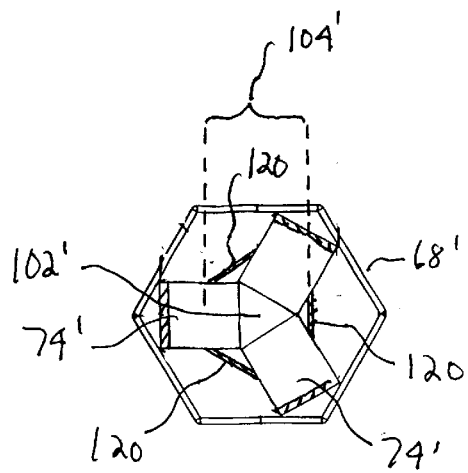
FIG. 27b is a top view of the flex-tube assembly shown in FIG. 27a taken along the line 27b—27b.
Figure 28B:
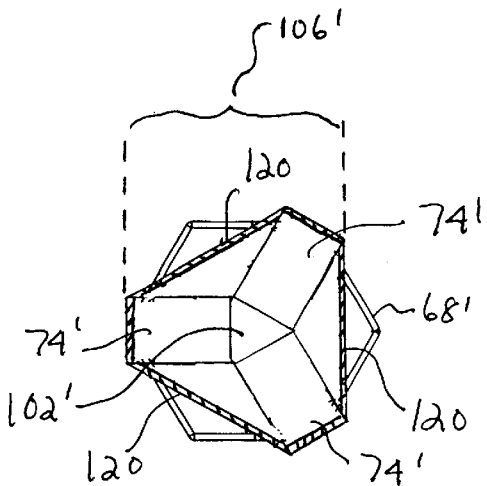
FIG. 28b is a top view of the flex-tube assembly of FIG. 28a taken along the line 28b—28b.

As shown in FIGS. 25a–28b, the flex-tube assembly 22' is formed as one piece. At the inlet end of the flex-tube assembly 22' is an elliptical piston head 82'. As is shown in FIG. 29 the base 86' is captured in the groove 42' between the proximal end of the male Luer taper 36' and the inner shroud 40' of the male Luer-lock insert 16' to form a tight seal about the top of the male Luer taper. The flex-tube assembly 22' is coated and lubricated in the same manner as previously described for the first configuration of the connector.

Figures 26A, 26B:
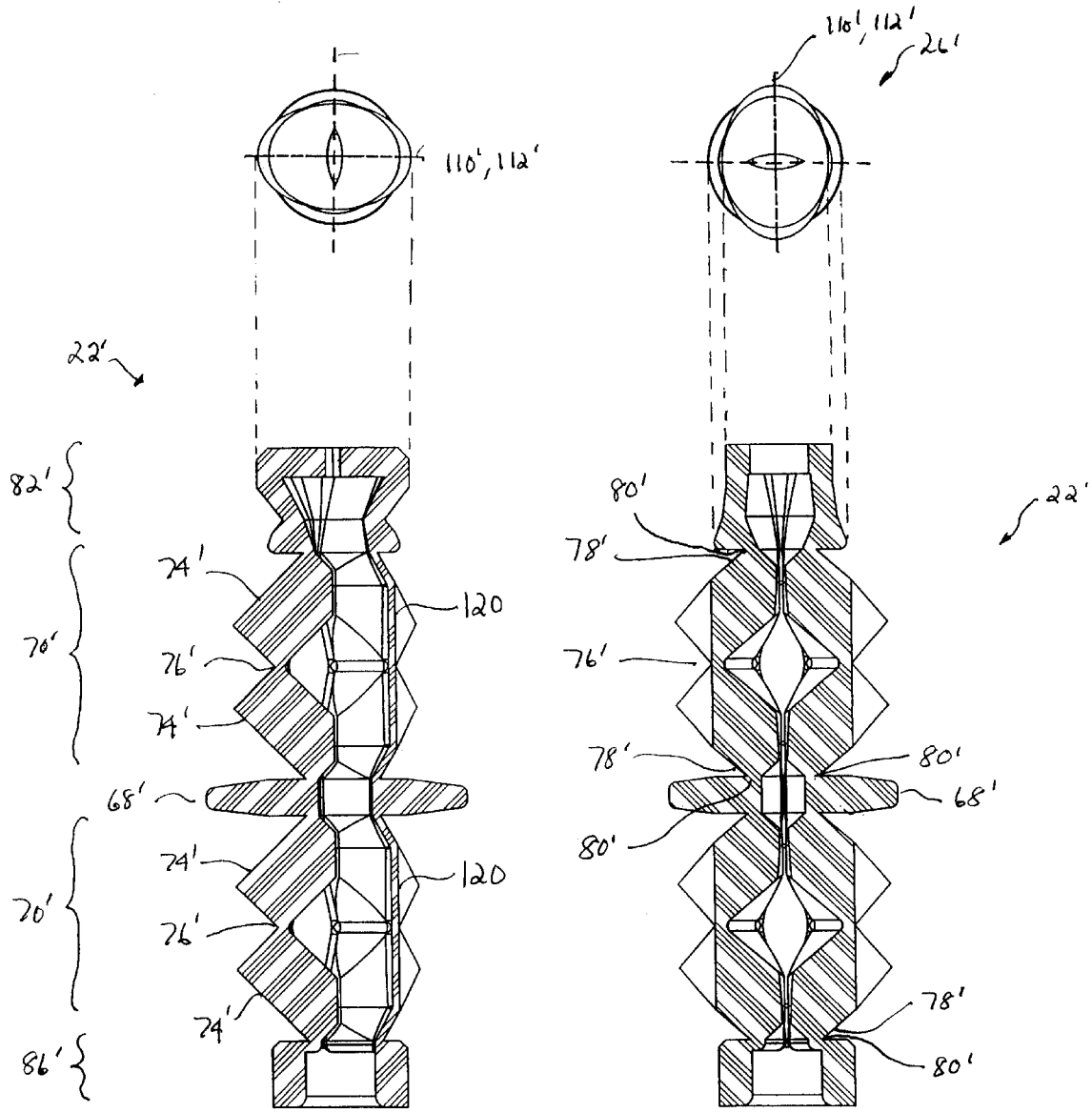
FIG. 26a and 26b are first and second full sectional views and top views of the flex-tube assembly shown in FIG. 25 with the views rotated 90 degrees from each other.
Figure 27A:
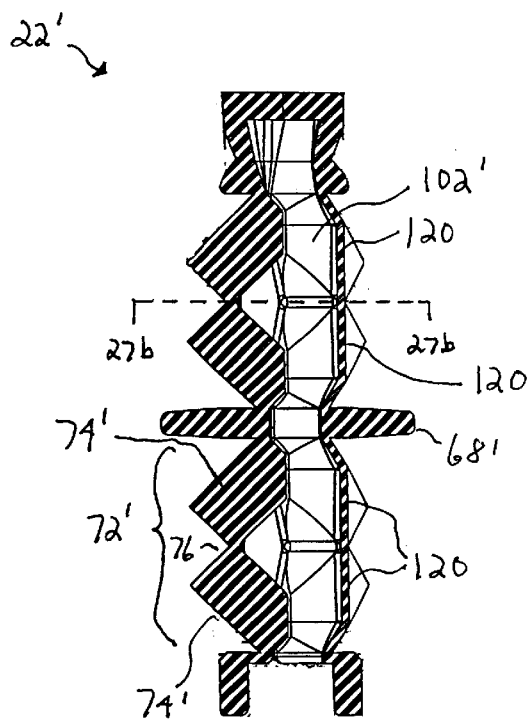
FIG. 27a is a full sectional view of the flex-tube assembly shown in FIG. 25 depicted in an uncompressed state.

The flex-tube assembly 22' is molded of a resilient flexible rubber material, such as silicone, having various thicknesses at different regions to provide functionality to the assembly. As shown in FIGS. 26a and 26b, the flex-tube assembly 22' includes an elliptical piston head 82' similar to that of the flex-tube piston of the other configuration. The flex-tube assembly 22' also includes a piston base 86' and a middle support 68'. Positioned between the piston head 82' and the middle support 68' is a collapsible/expandable section 70'. Similarly, positioned between the piston base 86' and the middle support 68' is another collapsible/expandable section 70'. Each collapsible/expandable section 70' includes three hinge assemblies 72' arranged in a triangle, as shown in FIG. 27a. Each hinge assembly 72' includes two triangular plates 74' and a hinge 76' about which the plates pivot. The edges 78' (FIG. 26b) of the plates parallel with the hinge 76' are attached to one of either the bottom of the piston head 82', the piston base 86' or the middle support 68'. The connection of the plate edges 78' to the piston head 82' and piston base 86' is facilitated by a head/base hinge 80'. As best shown in FIG. 25, the edges 118 of the hinge assemblies 72' perpendicular to the hinges 76' are joined to the edges of adjacent hinge assemblies by thin webs 120. The entire flex-tube assembly 22' is formed from the same mold, thus the webs 120 are made of the same material as the hinge assemblies 72' but are thinner than the hinge assemblies. For example, the thickest region of the hinge assembly plates 74' may be approximately 0.090 inches and the hinges 76' approximately 0.015 inches, while the thickness of the webs 120 may be approximately 0.010 inches. This difference allows for expansion of the collapsible/expandable section.

Figure 28A:
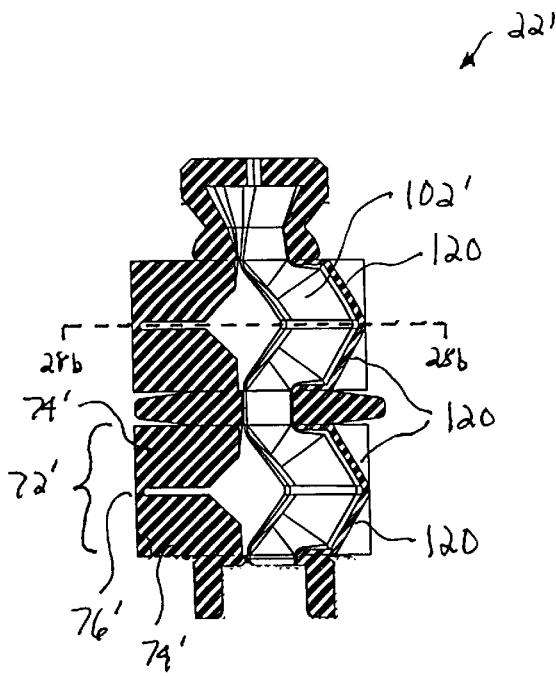
FIG. 28a is a full sectional view of the flex-tube assembly shown in FIG. 25 depicted in an compressed state.
Figures 29, 30:
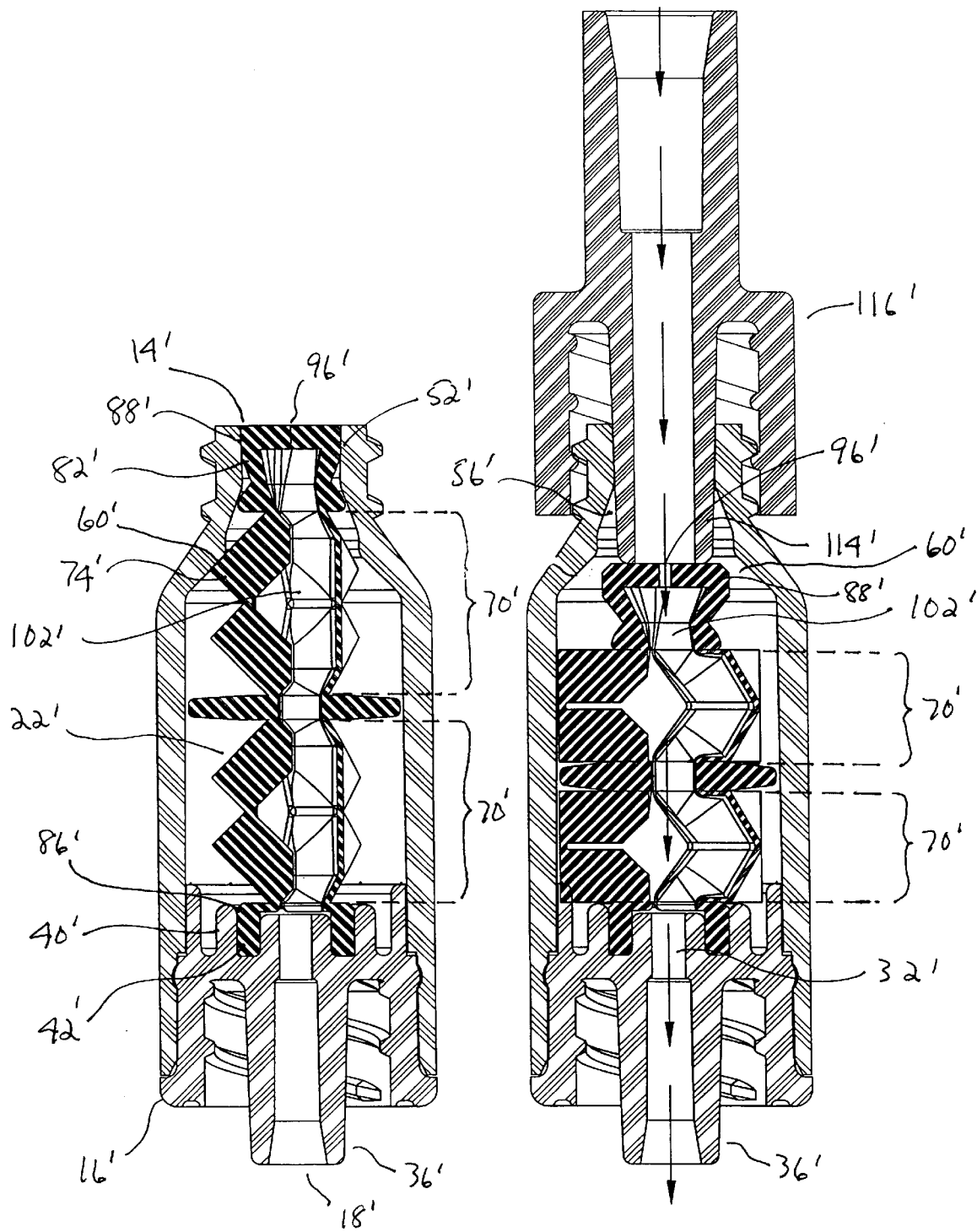
FIG. 29 is a full sectional view of a positive-bolus configuration of the medical connector of FIG. 21 depicting the flex-tube assembly in the uncompressed state.
FIG. 30 is a full sectional view of a positive-bolus configuration of the medical connector of FIG. 21 depicting the flex-tube assembly in the compressed state under pressure of an inserted blunt or needle-free cannula having a male Luer taper.

As shown in FIGS. 27a and 28a, the thickness and positioning of the hinge assemblies 72' of the flex-tube assembly 22' are designed to facilitate the expansion of the flex-tube assembly to either increase the volumetric fluid capacity of the fluid flow path 102' to provide a positive-bolus effect, or to maintain it at a substantially constant capacity to provide a no-bolus effect. If desired, the flex-tube assembly 22' may also be designed to provide a negative-bolus effect. The thickness and relative positioning of the hinge assemblies 72' and the webs 120 in turn are designed to provide a restoring force to the flex-tube assembly 22' to compress the flex-tube assembly and thus return the volumetric fluid capacity of the fluid flow path 102' to its original value.

The flex-tube assembly 22' is movable between an uncompressed state (FIG. 27a) and a compressed state (FIG. 28a). In the uncompressed state the flex-tube assembly 22' has a first maximum cross-sectional area 104', as shown in FIG. 27b, and the fluid path 102' defined by the flex-tube assembly 22' has a first internal volume. In the compressed state the flex-tube assembly 22' has a second maximum cross-sectional area 106' greater than the first maximum cross sectional area 104', as shown in FIG. 28b, and the fluid path 102' defined by the flex-tube assembly 22' has a second internal volume greater than or substantially equal to the first internal volume. The varying thicknesses of the flex-tube assembly 22' facilitates the movement between the uncompressed and compressed states. The thick hinge assemblies 72' of the flex-tube assembly 22' are instrumental in establishing the compressed state. Upon the application of downward force to the flex-tube assembly 22', the hinges 76' move outward and the respective plates 74' attached to these hinges collapse toward each other. As the plates 74' collapse the webs 120 stretch. For a positive-bolus connector this increases the internal volume of the fluid path 102' toward a second internal volume greater than the first internal volume. When the application of downward force is removed, the resiliency of the hinge assemblies 72' and the webs 120 force the hinges 76' inward and the plates 74' apart. Thus the flex-tube assembly 22' returns to its original uncompressed state and for a positive-bolus connector, the internal volume of the fluid path 102' decreases. For a no-bolus connector, the internal volume remains substantially constant as the flex-tube assembly 22' moves between compressed and uncompressed states.

Referring now to FIGS. 29 and 30, the connector 10' is initially in its inactive state or closed position as shown in FIG. 29. The flex-tube assembly 22' is pre-loaded and causes the piston head 82' to be biased into the ANSI Luer taper section 52'. The top hinge plates 74' of the flex-tube assembly 22' contacts the taper section 60' of the valve body 12' and prevents the top portion 88' of the piston head 82' from extending beyond the edge of the inlet port 14' to form a smooth and flush surface. The bore 96' through the piston head 82' is tightly squeezed shut by virtue of the normally elliptically shaped top portion 88' of the piston head being constrained into the circular cross-section of the ANSI Luer taper section 52'. The sharp pointed ends of the marquise-shaped bore 96' facilitate a tight seal upon compression of the bore along its minor axis 110' (FIG. 26b) and compression of the piston head 82' along its major axis 112'.

With reference to FIG. 30, as the male Luer tip 114' of the male Luer connector 116' is brought into contact with the top surface of the piston head 82', the collapsible sections 70' of the flex-tube assembly 22' collapse and expand. To prevent the flex-tube assembly 22' from buckling during compression, the maximum diameters of the middle support 68' and collapsible sections 70' are sized approximately equal to the diameter of the valve body 12'. As the flex-tube assembly 22' compresses, the top portion 88' of the piston head 82' moves out of the ANSI Luer taper section 52' and into the taper section 60'. The larger internal diameter of the taper section 60' allows the top portion 88' of the piston head to assume its naturally elliptical open shape. This, in turn, allows the bore 96' to assume its natural marquise-shape thereby opening a fluid path through the piston head 82'. In this condition the connector is in an active state or an open piston. Fluid flows through the bore 96', into the hollow interior of the piston head 82', through the interior of the flex-tube assembly 22' and into the tubular-housing. fluid path 32'.

In operation of a positive-bolus medical connector, as the flex-tube assembly 22' compresses it expands and the fluid capacity of the fluid path 102' increases, thus the volume of fluid within the connector increases during activation of the valve. As the male Luer tip 114' is withdrawn, the restoring force generated by the hinge assemblies 72' and webs 120 cause the flex-tube assembly 22' to return to a noncollapsed state (FIG. 29) and the internal volume of the flex-tube assembly to decrease. Simultaneously, the elliptical top portion 88' of the piston head 82' is guided into the ANSI Luer taper section 52' by the tapered ramp/lock section 56' where it is once again forced into the constrained circular shape of the ANSI Luer taper section to close off the bore 96' and reestablish a positive seal. As the internal fluid capacity of the flex-tube assembly 22' decreases the fluid contained therein is displaced. Because the bore 96' has established a positive seal at the inlet port 14', the fluid is displaced toward the outlet port 18'. The displacement of fluid toward the outlet port 18' prevents a negative-bolus effect.

As with the first-configuration connector, the volumetric increase of the fluid path 102' during depression of the flex-tube assembly 22' is dependent on the depth to which the male Luer tip 114' is inserted into the inlet port 14'. In one embodiment of the second-configuration connector, the flex-tube assembly is dimensioned such that the volumetric capacity of the fluid path 102' during deactuation, i.e., the priming volume, is 0.105 ml. The maximum volumetric capacity during actuation is greater than the priming volume.

Figure 31:
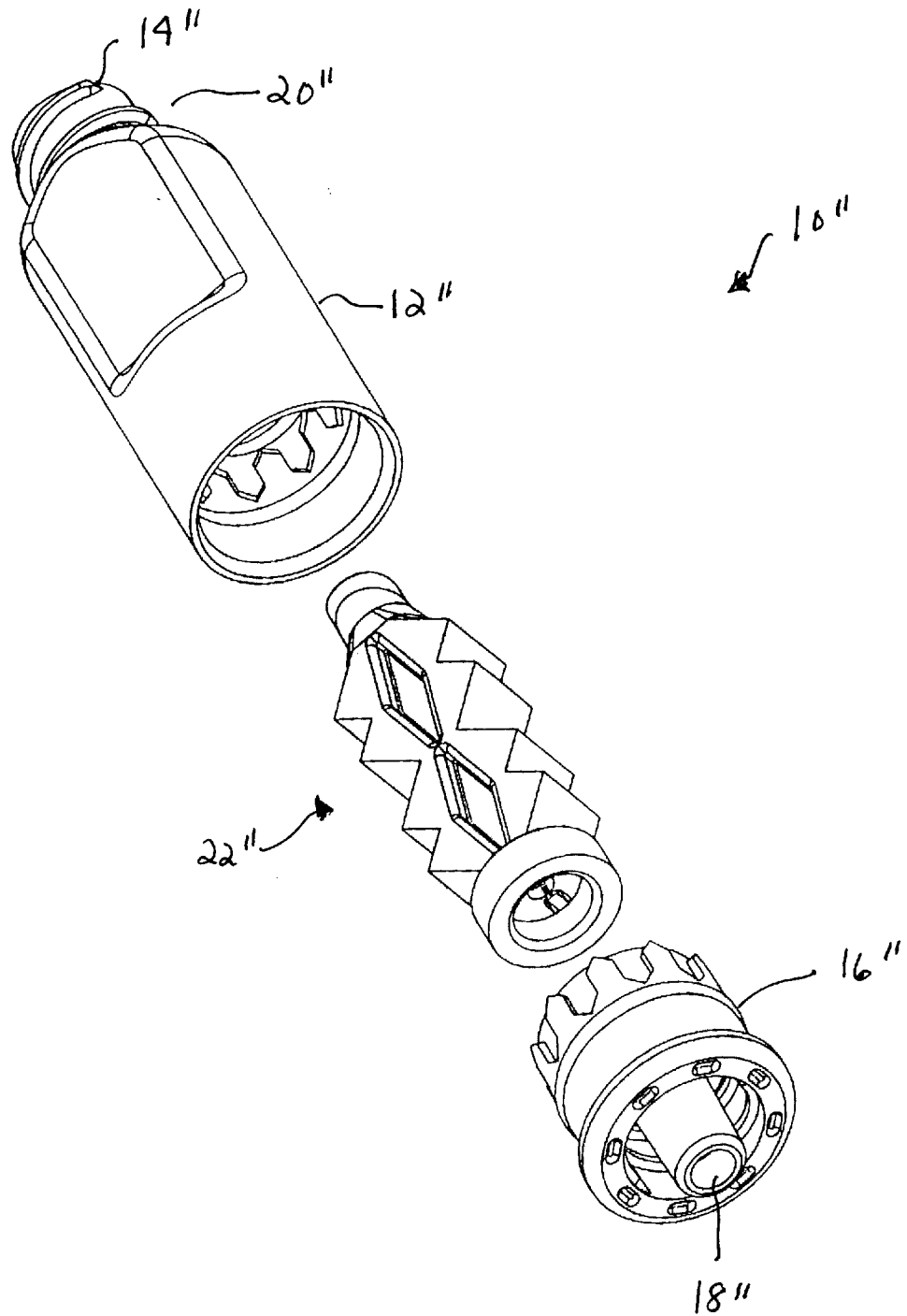
FIG. 31 is an exploded perspective view of a medical connector that incorporates aspects of the present invention, depicting a valve body, a male Luer-lock insert, and a one-piece flex-tube assembly, i.e., valve assembly.
Figure 33B:
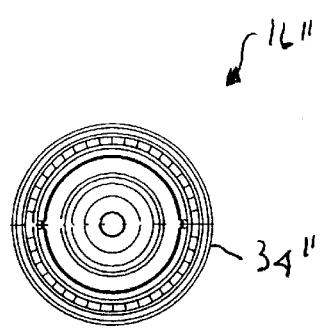
FIGS. 33a–33c depict various views of the male Luer-lock insert shown in FIG. 32, including a side elevation view, a top plan view, and a full sectional view.

With reference to FIG. 31, there is shown another configuration of a medical connector which incorporates aspects of the invention. Except for the flex-tube assembly and the valve body, this configuration of the connector is generally similar to the connector of FIG. 21. Accordingly, the description of this connector primarily centers around the flex-tube assembly and the valve body. For ease in correlating the two configurations, the numerals associated with elements of the third configuration are the same as those of the second configuration, except they are double primed.

Figure 32:
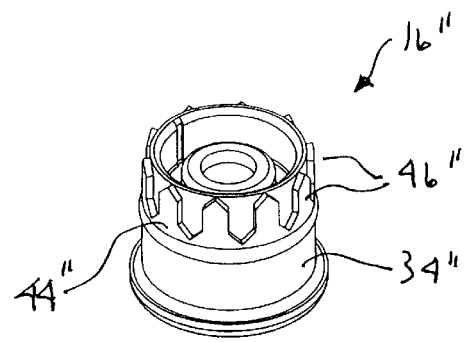
FIG. 32 is a perspective view of the male Luer-lock insert shown in FIG. 31.
Figure 33A:
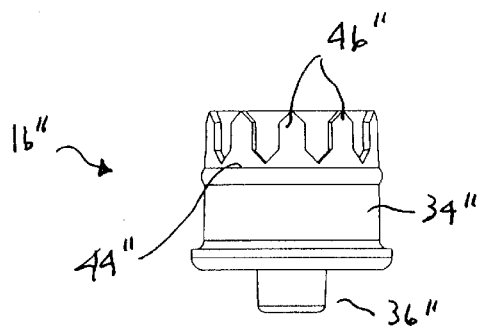
Figure 33C:
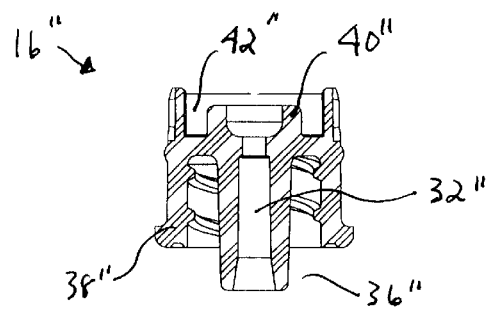
Figure 34:
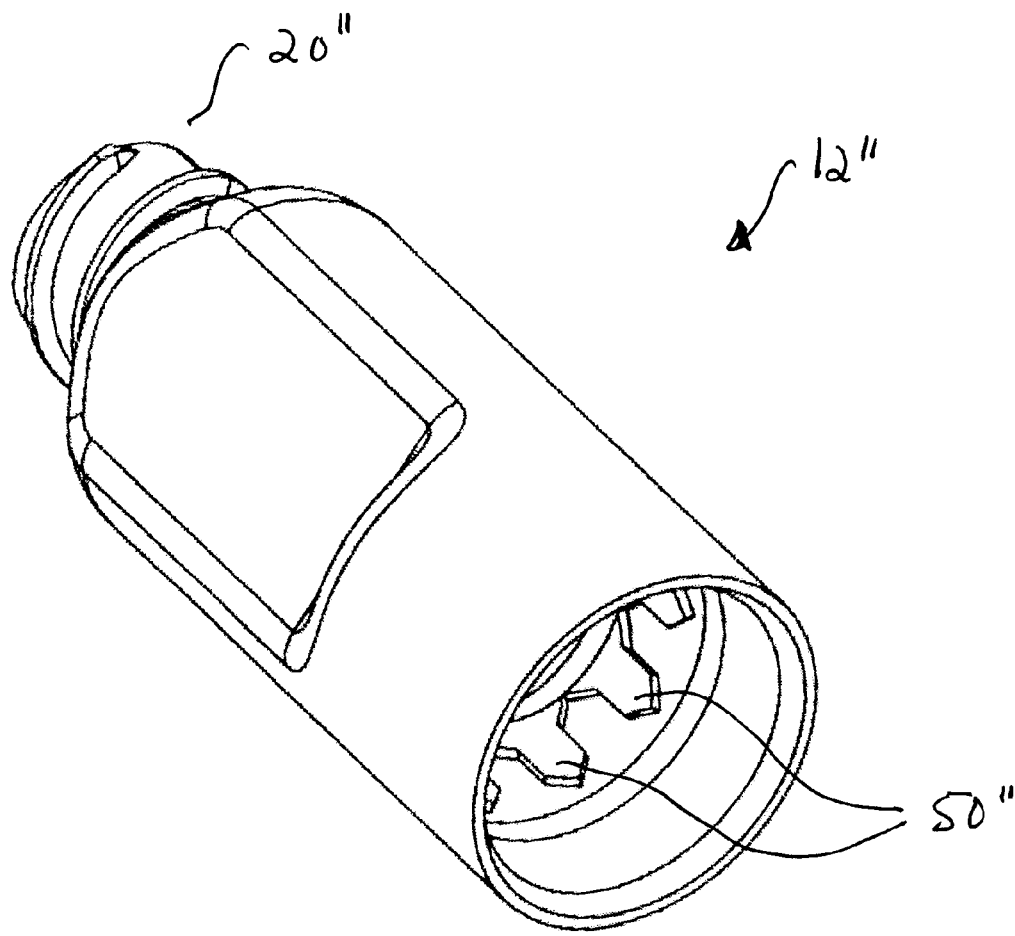
FIG. 34 is a perspective view of the valve body shown in FIG. 31.
Figure 35B:
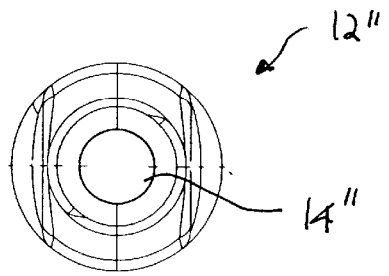
FIGS. 35a–35d depict various views of the valve body shown in FIG. 34, including a first side elevation view, a top plan view, a full sectional view and a second side elevation view rotated 90 degrees relative the first side elevation view.
Figure 35A:
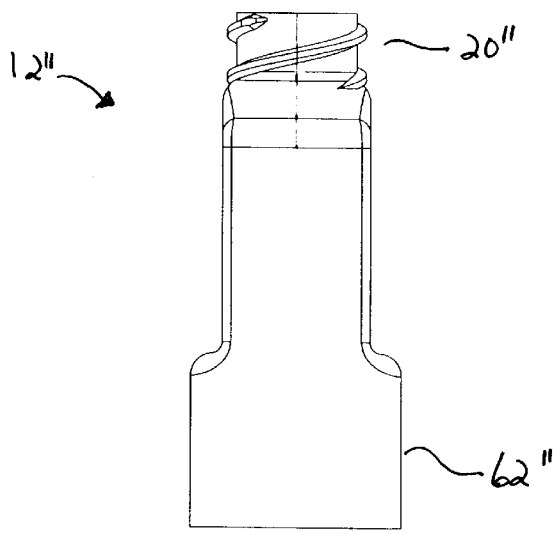
Figure 35C:
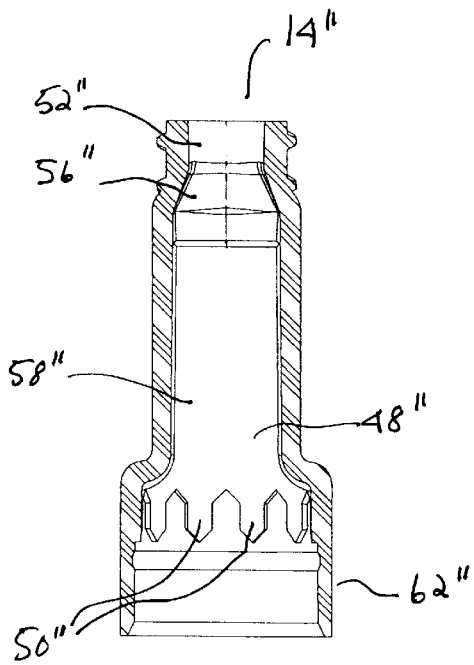
Figure 35D:
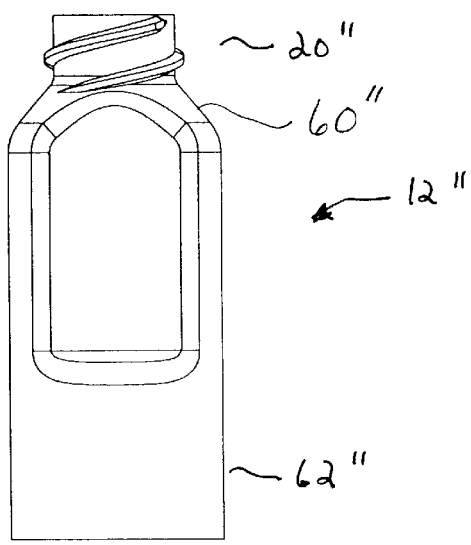
Figure 36:
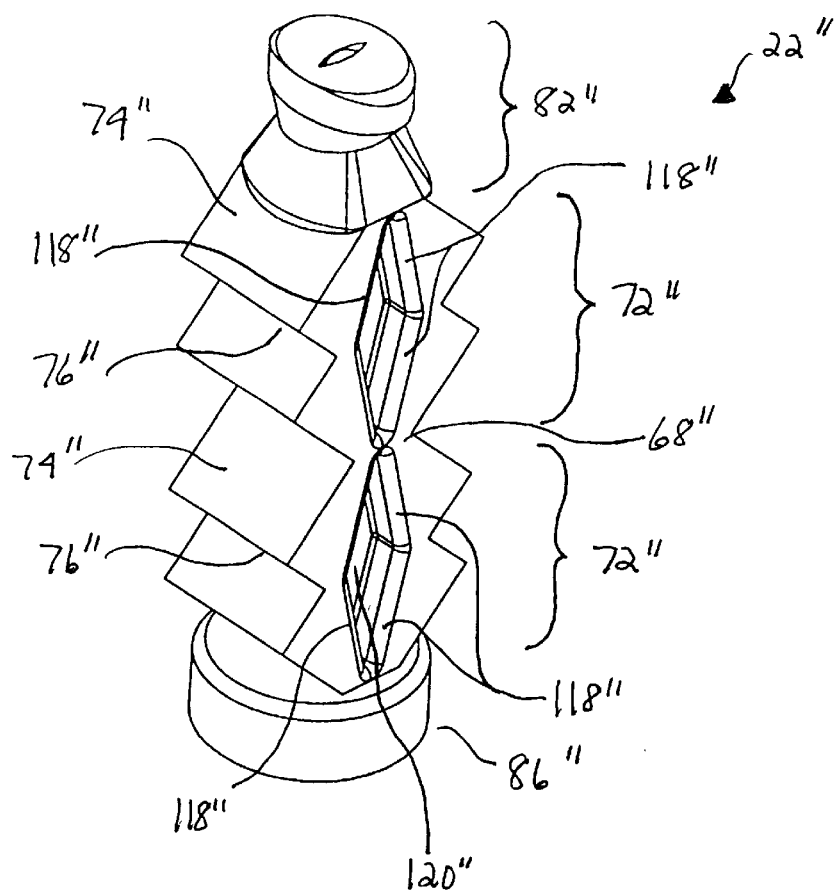
FIG. 36 is a perspective view of the flex-tube assembly in FIG. 31, depicting the flex-tube assembly in an uncompressed state.
Figures 37A, 37B:
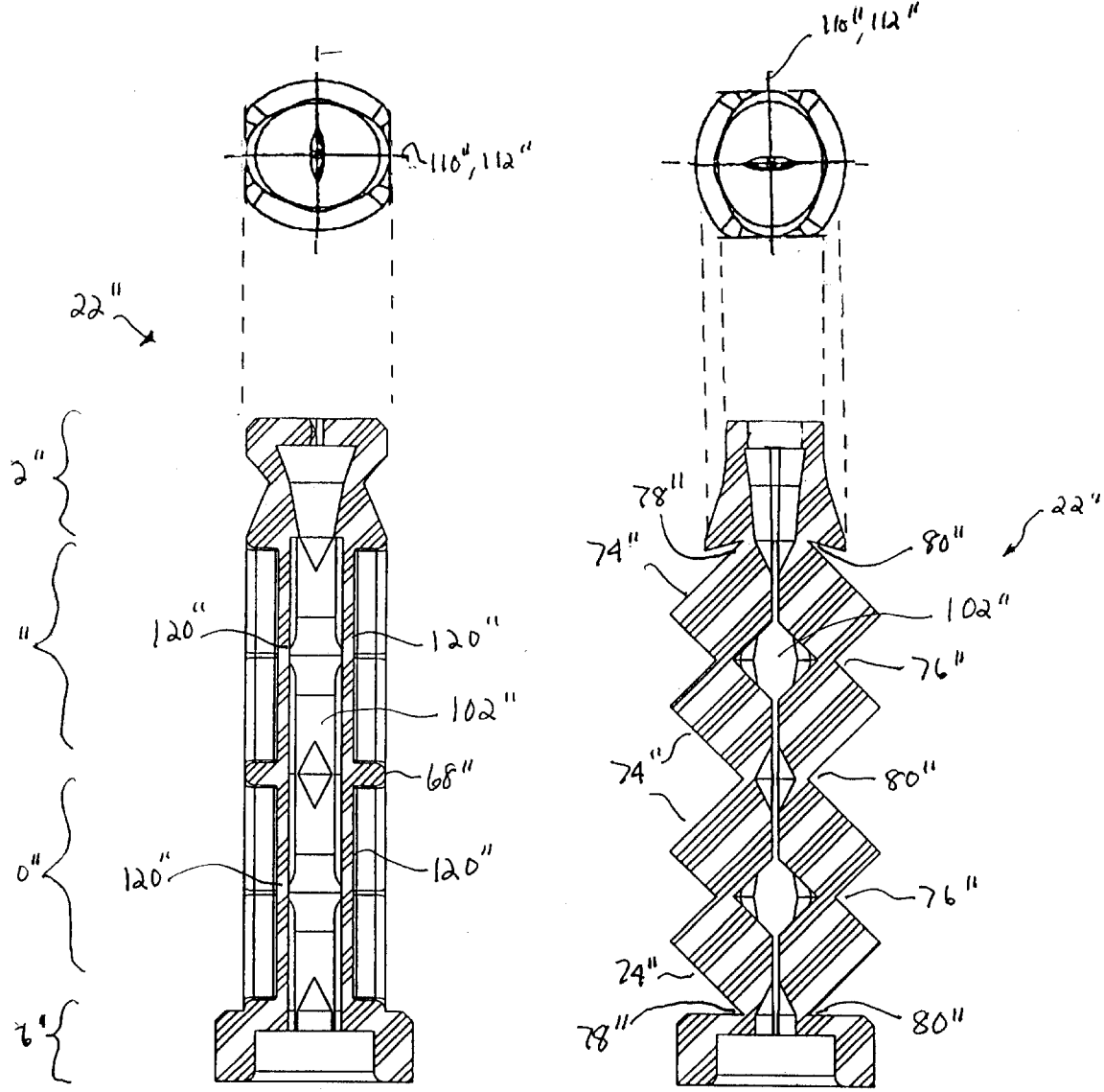
FIGS. 37a–37b are first and second full sectional views and top views of the flex-tube assembly shown in FIG. 36 with the views rotated 90 degrees from each other.
Figures 37A, 37B:
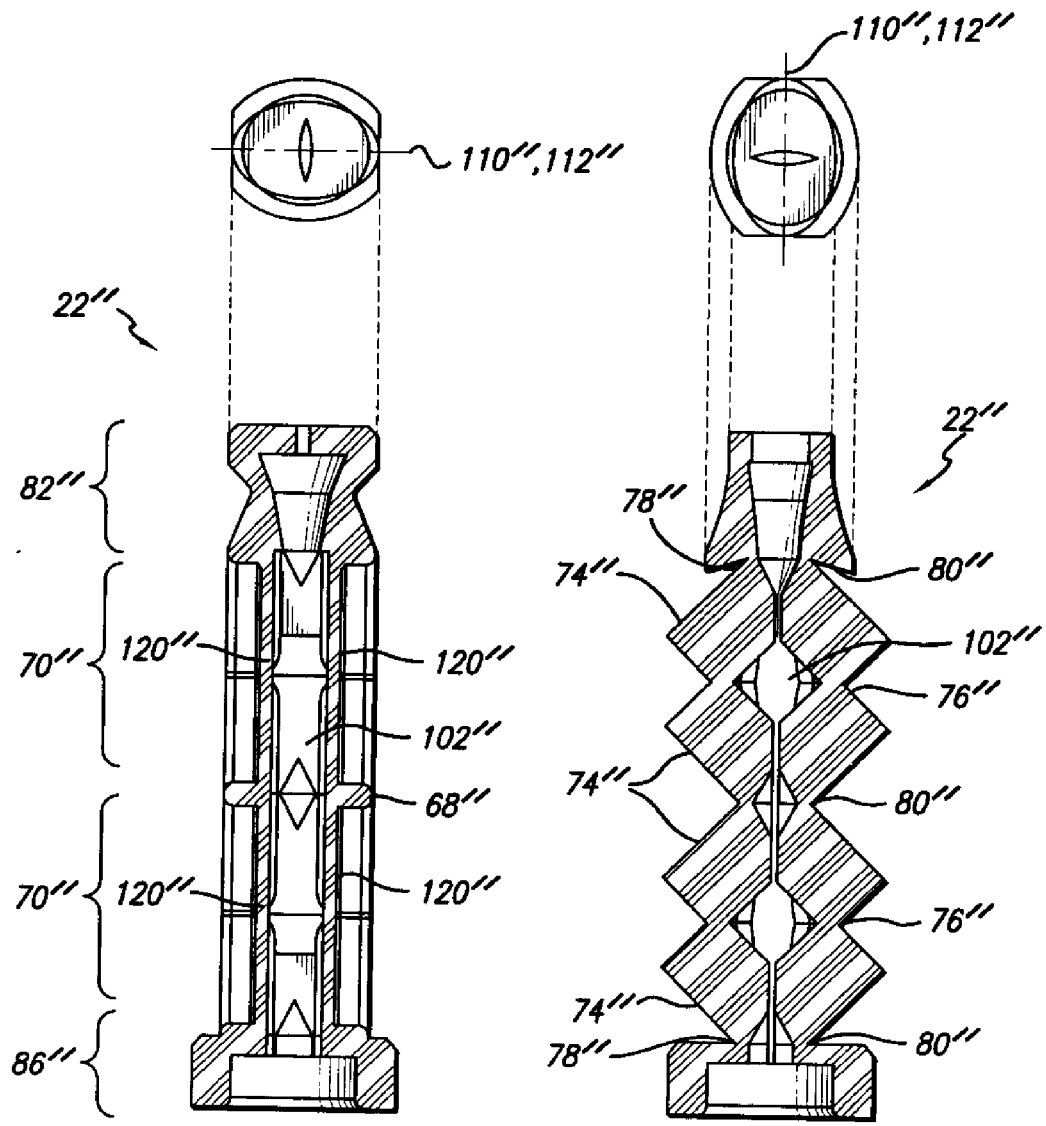
Figure 38B:
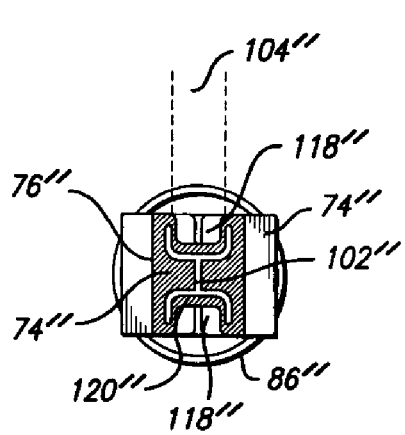
Figure 39B:
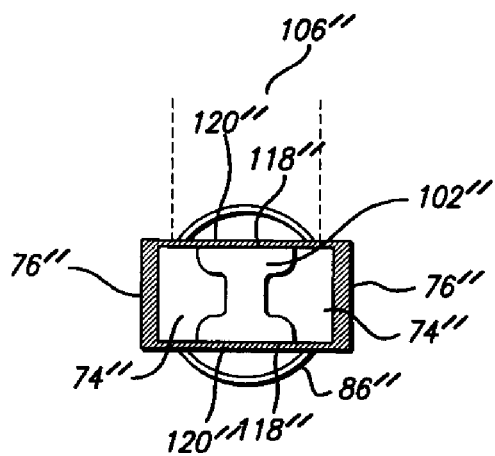
Figure 38A:
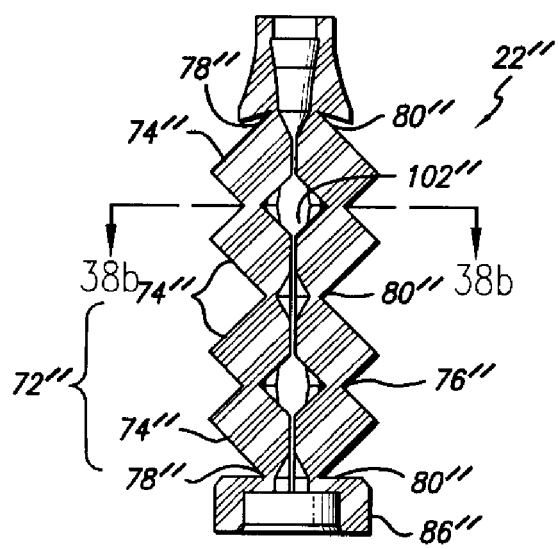
Figure 39A:
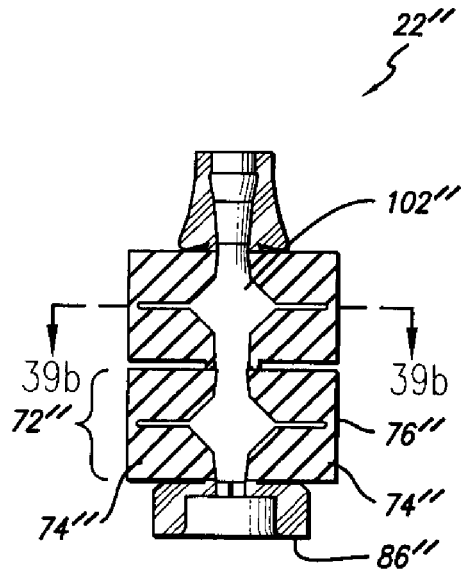

As shown in FIG. 31, the connector 10" comprises a valve body 12", a male Luer-lock insert 16", and flex-tube assembly 22". As shown in FIGS. 32–33c the male Luer-lock insert 16" is substantially identical to the male Luer-lock insert 16' (FIGS. 22a–22d) of the second configuration. As shown in FIGS. 34–35d, the valve body 12" is also substantially similar to the valve body 12' (FIGS. 23–24d) of the second configuration, except that a proportion of the tubular valve body is flattened to accommodate for the rectangular design of the flex-tube assembly 22". As shown in FIGS. 36–37b, the flex-tube assembly 22" is formed similarly to the flex-tube assembly 22' (FIGS. 25a–26b) of the second configuration. At the inlet end of the flex-tube assembly 22" is the elliptical piston head 82". The base 86" is captured in the groove 42" (FIG. 33c) to form a tight seal about the top of the male-Luer taper 36". The flex-tube assembly 22" is coated and lubricated as previously described for the second configuration. As shown in FIG. 37a, the flex-tube assembly 22" of the third configuration includes a pair of collapsible/expandable sections 70". Each collapsible/expandable section 70" includes a pair of opposed hinge assemblies 72". Each hinge assembly 72" includes two triangular plates 74" and a hinge 76" about which the plates pivot.

Figure 38B:
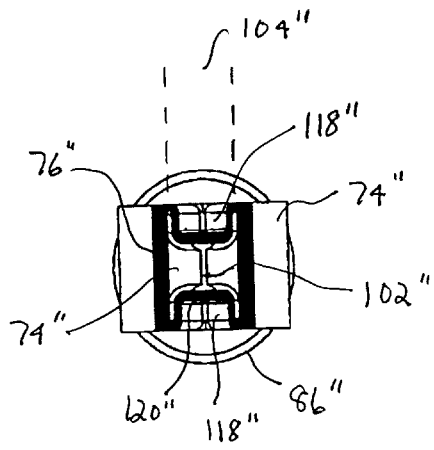
FIG. 38b is a top view of the flex-tube assembly shown in FIG. 38a taken along the line 38b—38b.
Figure 39B:
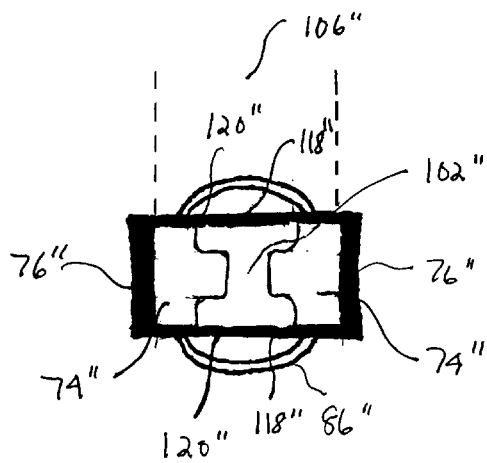
FIG. 39b is a top view of the flex-tube assembly of FIG. 39a taken along the line 39b—39b.
Figure 38A:
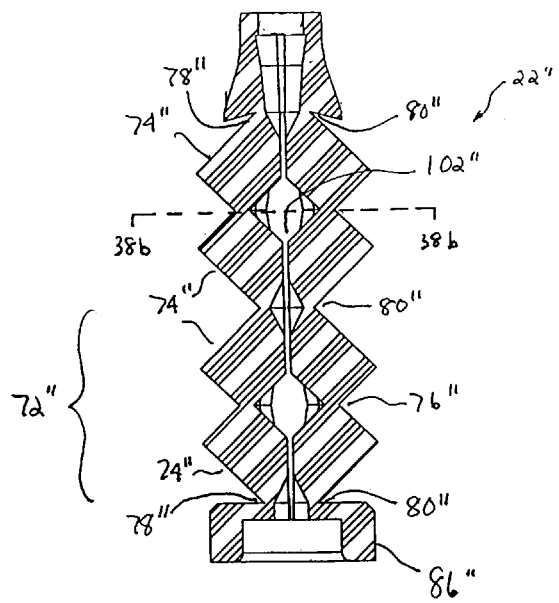
FIG. 38a is a full sectional view of the flex-tube assembly shown in FIG. 36 depicted in an uncompressed state.
Figure 39A:
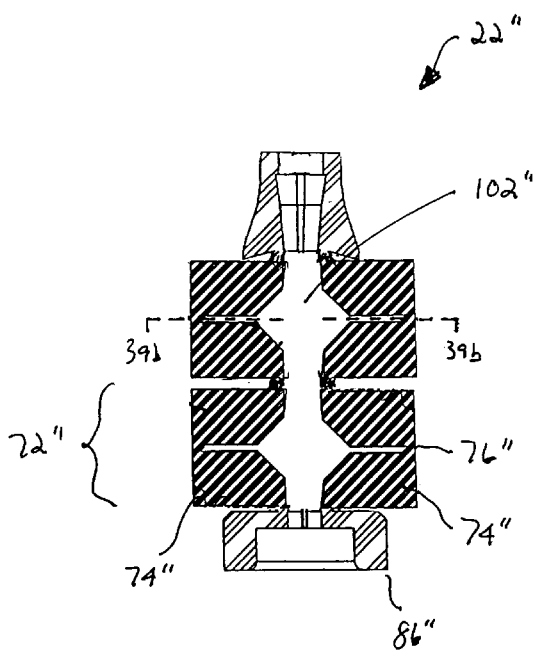
FIG. 39a is a full sectional view of the flex-tube assembly shown in FIG. 36 depicted in an compressed state.
Figure 3:
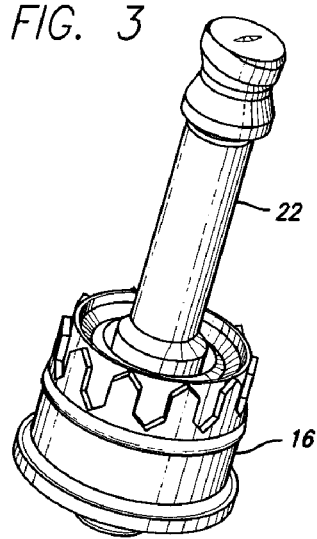
Figure 4:
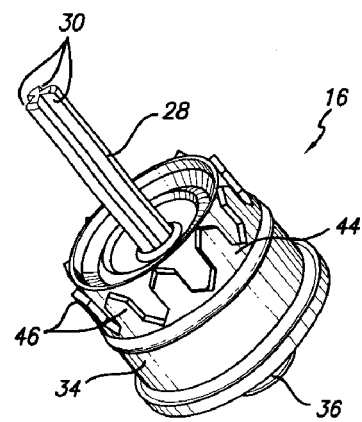
Figure 5B:
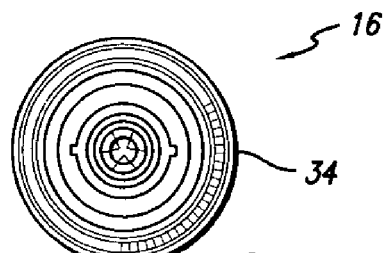
Figure 5A:
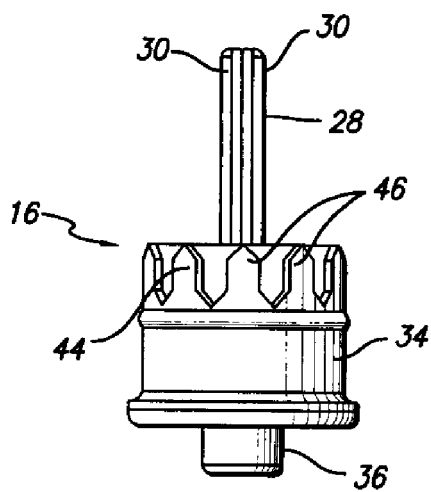
Figure 5D:
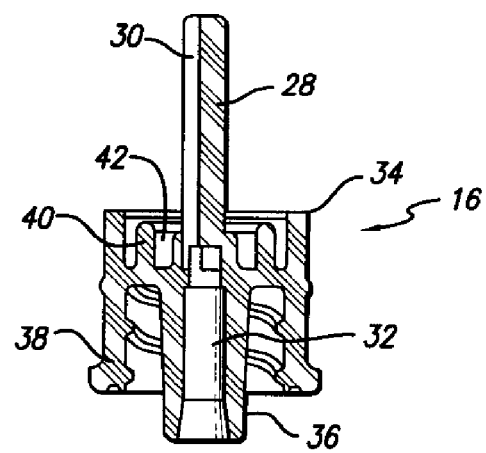
Figure 5C:
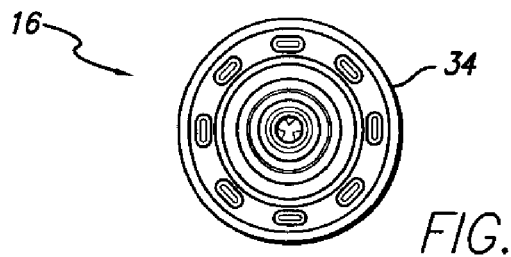
Figure 12:
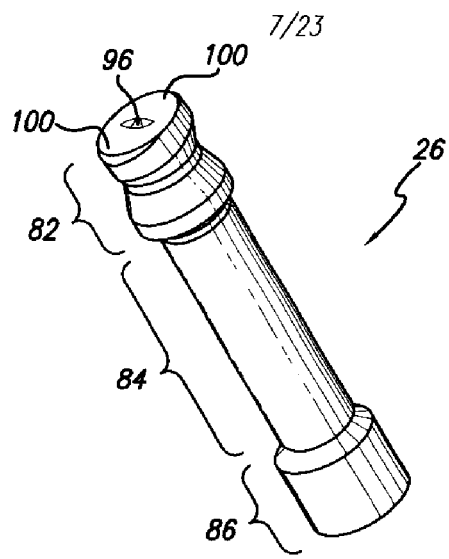

As best shown in FIG. 36, the hinge-assemblies 72" include beveled edges 118". The beveled edges 118" perpendicular to the hinges 76" are joined to the edges of the opposite hinge assembly by a thin web 120". The flex-tube assembly 22" is movable between an uncompressed state (FIG. 38a) and a compressed state (FIG. 39a). In the uncompressed state the flex-tube assembly 22" has a first maximum internal cross-sectional area 104", as shown in FIG. 38b, and the fluid path 102" defined by the flex-tube assembly 22" has a first internal volume. In the compressed state the flex-tube assembly 22" has a second maximum internal cross-sectional area 106" greater than the first maximum internal cross sectional area 104", as shown in FIG. 39b, and the fluid path 102" defined by the flex-tube assembly 22" has a second internal volume greater than or substantially equal to the first internal volume. Upon the application of downward force to the flex-tube assembly 22", the hinges 76" move outward and the respective plates 74" attached to these hinges collapse toward each other. As the plates 74" collapse, the bevels 118" flatten out and the webs 120" stretch, and for a positive-bolus connector, there is an increase in the internal volume of the fluid path 102". For a no-bolus connector, the internal volume remains substantially constant. When the application of downward force is removed, the resiliency of the hinge assemblies 72" and the webs 120" force the hinges 76" inward and the plates 74" apart. Thus the flex-tube assembly 22" returns to its original uncompressed state.

Other than the number of hinge assemblies 72", the flex tube assembly 22" of the third configuration is substantially identical to the flex-tube assembly 22' of the second configuration. In conjunction with their respective valve bodies 12', 12", the flex-tube assemblies 22', 22" function in substantially identical ways.

Accordingly, a description of the detailed operation of the third configuration may be had by reference to the preceding description of the detailed operation of the second configuration.

Thus there has been shown and described a new and useful valve for use in medical connectors that provides a positive-bolus effect or a no-bolus effect while the valve is being deactuated at the inlet end.

It will be apparent from the foregoing that while particular embodiments of the invention have been illustrated and described, various modifications can be made without departing from the spirit and scope of the invention. Accordingly, it is not intended that the invention be limited, except as by the appended claims.

What is claimed is:

1. A method of controlling the flow of fluid between an inlet port and an outlet port of a medical connector having a valve assembly defining an internal fluid path having a volume, the valve assembly having an inlet end disposed within the inlet port and an outlet end communicating with the outlet port, the inlet end carrying a bore that is closed when within the inlet port and that naturally opens when outside the inlet port, said method comprising the steps of:

increasing the volume of the fluid path while opening the bore; and subsequently decreasing the volume of the fluid path while closing the bore.

2. The method of claim 1 wherein the valve assembly is formed of a resiliently deformable material and the step of increasing the volume of the fluid path while opening the bore comprises the steps of:

displacing the inlet end from the inlet port; and expanding the valve assembly in a generally radial outward direction relative to the axis of the fluid flow path.

3. The method of claim 2 wherein step of displacing the inlet end from the inlet port comprises the step of inserting a male-Luer taper into the inlet port and applying pressure to the inlet end.

4. The method of claim 3 wherein the step of decreasing the volume of the fluid path while closing the bore comprises the steps of:

placing the inlet end in the inlet port; and collapsing the valve assembly in a generally radial inward direction relative to the axis of the fluid flow path.

5. The method of claim 4 wherein the step of placing the inlet end in the inlet port comprises the step of removing the male-Luer taper from the inlet port.

6. A method of controlling the flow of fluid between an inlet port and an outlet port of a medical connector, the medical connector having an internal fluid path having a volume, and having an axially compressible valve assembly defining an internal passageway forming part of the fluid path, the valve assembly having an inlet end disposed within the inlet port and an outlet end communicating with the outlet port, the inlet end carrying a bore that is closed when within the inlet port and that naturally opens when outside the inlet port, said method comprising the steps of:

maintaining the volume of the fluid path substantially constant while axially compressing the valve assembly and opening the bore; and subsequently maintaining the volume of the fluid path substantially constant while axially decompressing the valve assembly and closing the bore.

7. The method of claim 6 wherein the valve assembly is formed of a resiliently deformable material and the step of maintaining the volume of the fluid path substantially constant while axially compressing the valve assembly and opening the bore comprises the steps of:

displacing the inlet end from the inlet port; and expanding the valve assembly in a generally radial outward direction relative to the axis of the fluid flow path.

8. The method of claim 1 wherein the step of displacing the inlet end from the inlet port comprises the step of inserting a male-Luer taper into the inlet port and applying pressure to the inlet end.

9. The method of claim 8 wherein the step of maintaining the volume of the fluid path substantially constant while axially decompressing the valve assembly and closing the bore comprises the steps of:

placing the inlet end in the inlet port; and collapsing the valve assembly in a generally radial inward direction relative to the axis of the fluid flow path.

10. The method of claim 9 wherein the step of placing the inlet end in the inlet port comprises the step of removing the male-Luer taper from the inlet port.

11. A method of controlling the flow of fluid between an inlet port and an outlet port of a medical connector having a valve assembly defining an internal fluid path having a volume, the valve assembly having an inlet end disposed within the inlet port and an outlet end communicating with the outlet port, the inlet end carrying a bore that is closed when within the inlet port and opened when outside the inlet port, the valve assembly further comprising a first and a second plate, the first plate being connected to the second plate by a hinge about which the plates are adapted to pivot, said method comprising the steps of:

collapsing the first plate towards the second plate while opening the bore, thereby moving the hinge in a generally radial outward direction relative to the axis of the fluid flow path and increasing the volume of the fluid path; and subsequently retracting the first plate from the second plate while closing the bore, thereby moving the hinge in a generally radial inward direction relative to the axis of the fluid flow path and decreasing the volume of the fluid path.

12. The method of claim 11 wherein the step of collapsing the first plate towards the second plate while opening the bore comprises the steps of:

displacing the inlet end from the inlet port thereby expanding the valve assembly in a generally radial outward direction relative to the axis of the fluid flow path.

13. The method of claim 12 wherein the step of displacing the inlet end from the inlet port comprises the step of inserting a male-Luer taper into the inlet port and applying pressure to the inlet end.

14. The method of claim 13 wherein the step of retracting the first plate from the second plate while closing the bore comprises the steps of:

placing the inlet end in the inlet port thereby collapsing the valve assembly in a generally radial inward direction relative to the axis of the fluid flow path.

15. The method of claim 14 wherein the step of placing the inlet end in the inlet port comprises the step of removing the male-Luer taper from the inlet port.

16. A method of controlling the flow of fluid between an inlet port and an outlet port of a medical connector having an axially compressible valve assembly defining an internal fluid path having a volume, the valve assembly having an inlet end disposed within the inlet port and an outlet end communicating with the outlet port, the inlet end carrying a bore that is closed when within the inlet port and opened when outside the inlet port, the valve assembly further comprising a first and a second plate, the first plate being connected to the second plate by a hinge about which the plates are adapted to pivot, said method comprising the steps of:

collapsing the first plate towards the second plate while axially compressing the valve assembly and opening the bore, thereby moving the hinge in a generally radial outward direction relative to the axis of the fluid flow path and maintaining the volume of the fluid path substantially constant; and subsequently retracting the first plate from the second plate while axially decompressing the valve assembly and closing the bore, thereby moving the hinge in a generally radial inward direction relative to the axis of the fluid flow path and maintaining the volume of the fluid path substantially constant.

17. The method of claim 16 wherein the step of collapsing the first plate towards the second plate while axially compressing the valve assembly and opening the bore comprises the steps of:

displacing the inlet end from the inlet port thereby expanding the valve assembly in a generally radial outward direction relative to the axis of the fluid flow path.

18. The method of claim 17 wherein the step of displacing the inlet end from the inlet port comprises the step of inserting a male-Luer taper into the inlet port and applying pressure to the inlet end.

19. The method of claim 18 wherein the step of retracting the first plate from the second plate while axially decompressing the valve assembly and closing the bore comprises the steps of:

placing the inlet end in the inlet port thereby collapsing the valve assembly in a generally radial inward direction relative to the axis of the fluid flow path.

20. The method of claim 19 wherein the step of placing the inlet end in the inlet port comprises the step of removing the male-Luer taper from the inlet port.

* * * * *

UNITED STATES PATENT AND TRADEMARK OFFICE
CERTIFICATE OF CORRECTION

PATENT NO.     : 6,706,022 B1
DATED          : March 16, 2004
INVENTOR(S)    : Karl R. Leinsing et al.

It is certified that error appears in the above-identified patent and that said Letters Patent is hereby corrected as shown below:

Title page should be deleted to appear as per attached title page.

The sheets of drawings consisting of figures 1-39 should be deleted as per attached figures 1-39.

Column 5,
Line 60, delete "carryies," and insert -- carries --.

Column 8
Line 37, delete "invention," and insert -- invention. -- (replace comma with a period).

Column 10,
Line 2, delete "between-the" and insert -- between the --.
Line 22, after "piston 26" insert -- . -- (a period).

Column 11,
Line 59, start a new paragraph at "With reference to FIG. 15".

Column 13,
Line 6, delete "then" and insert -- than --.
Line 59, at "As best shown" start a new paragraph.

Column 15,
Line 16, after "tubular-housing" delete "." (a period).

UNITED STATES PATENT AND TRADEMARK OFFICE
CERTIFICATE OF CORRECTION

PATENT NO. : 6,706,022 B1
DATED : March 16, 2004
INVENTOR(S) : Karl R. Leinsing et al.

It is certified that error appears in the above-identified patent and that said Letters Patent is hereby corrected as shown below:

Column 16,
Line 47, is not a new paragraph.

Column 17,
Line 53, delete "claim 1" and insert -- claim 7 --.

Signed and Sealed this

Nineteenth Day of April, 2005

JON W. DUDAS
*Director of the United States Patent and Trademark Office*

(12) United States Patent
Leinsing et al.

(10) Patent No.: US 6,706,022 B1
(45) Date of Patent: Mar. 16, 2004

(54) NEEDLELESS MEDICAL CONNECTOR WITH EXPANDABLE VALVE MECHANISM

(75) Inventors: Karl R. Leinsing, Raleigh, NC (US); Theodore J. Mosler, Raleigh, NC (US)

(73) Assignee: ALARIS Medical Systems, Inc., San Diego, CA (US)

( * ) Notice: Subject to any disclaimer, the term of this patent is extended or adjusted under 35 U.S.C. 154(b) by 0 days.

(21) Appl. No.: 09/361,543

(22) Filed: Jul. 27, 1999

(51) Int. Cl.[7] .................................................. A61M 5/00
(52) U.S. Cl. ........................................ 604/247; 604/256
(58) Field of Search ........................... 604/34, 256, 36, 604/905, 284, 99.02, 99.03, 99.04, 167.03, 236, 247, 249, 288.03, 323, 335

(56) References Cited

U.S. PATENT DOCUMENTS

| | | | |
|---|---|---|---|
| 4,479,795 A | 10/1984 | Mustachich et al. | 604/53 |
| 4,810,241 A | 3/1989 | Rogers | 604/28 |
| 4,919,658 A | 4/1990 | Badia | 604/265 |
| 5,195,994 A | 3/1993 | Dieringer | 604/283 |
| 5,215,538 A | 6/1993 | Larkin | 604/249 |
| 5,242,432 A * | 9/1993 | DeFrank | 604/284 |
| 5,360,413 A | 11/1994 | Leason et al. | 604/249 |
| 5,509,433 A * | 4/1996 | Paradis | 604/249 |
| 5,676,346 A | 10/1997 | Leinsing | 251/149.1 |
| RE35,841 E | 7/1998 | Frank et al. | 604/256 |
| 5,820,601 A | 10/1998 | Mayer | 604/167 |
| 5,839,715 A * | 11/1998 | Leinsing | 604/905 |
| 6,029,946 A * | 2/2000 | Doyle | 604/256 |
| 6,039,302 A * | 3/2000 | Cote, Sr. et al. | 604/256 |
| 6,117,114 A * | 9/2000 | Paradis | 604/246 |
| 6,290,206 B1 | 9/2001 | Doyle | 251/149.1 |

FOREIGN PATENT DOCUMENTS

| | | | |
|---|---|---|---|
| WO | WO 94/22522 | 10/1994 | A61M/39/00 |
| WO | WO 98/26835 | 6/1998 | A61M/39/26 |
| WO | WO 99/24090 | 5/1999 | A61M/5/00 |

* cited by examiner

*Primary Examiner*—Manuel Mendez
(74) *Attorney, Agent, or Firm*—Fulwider Patton Lee & Utecht, LLP

(57) ABSTRACT

A needleless connector for medical use, adapted to facilitate the flow of fluid therethrough, includes a housing having an inlet port and an outlet port. The connector also includes a flex-tube assembly defining a fluid path between the inlet port and the outlet port. The flex-tube assembly is movable between uncompressed and compressed states. The flex-tube assembly has a first internal volume when in the uncompressed state and a second internal volume, greater than or substantially equal to the first internal volume, when in the compressed state.

20 Claims, 31 Drawing Sheets

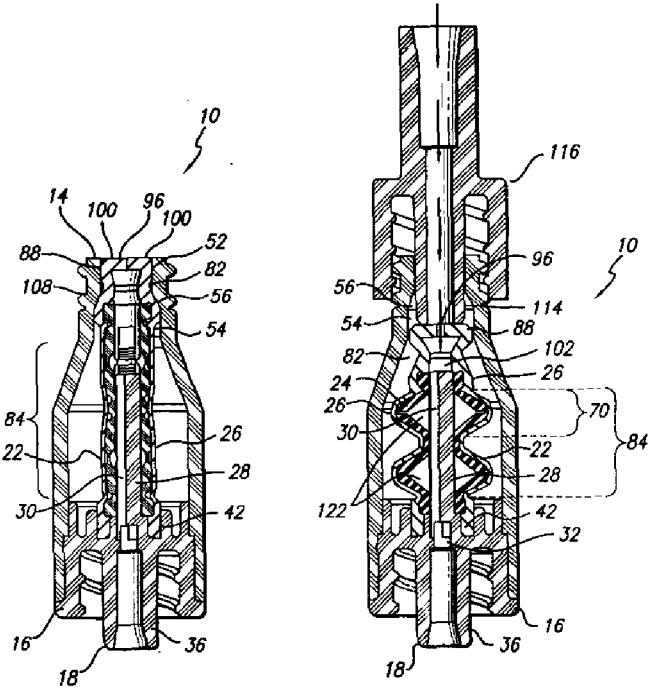

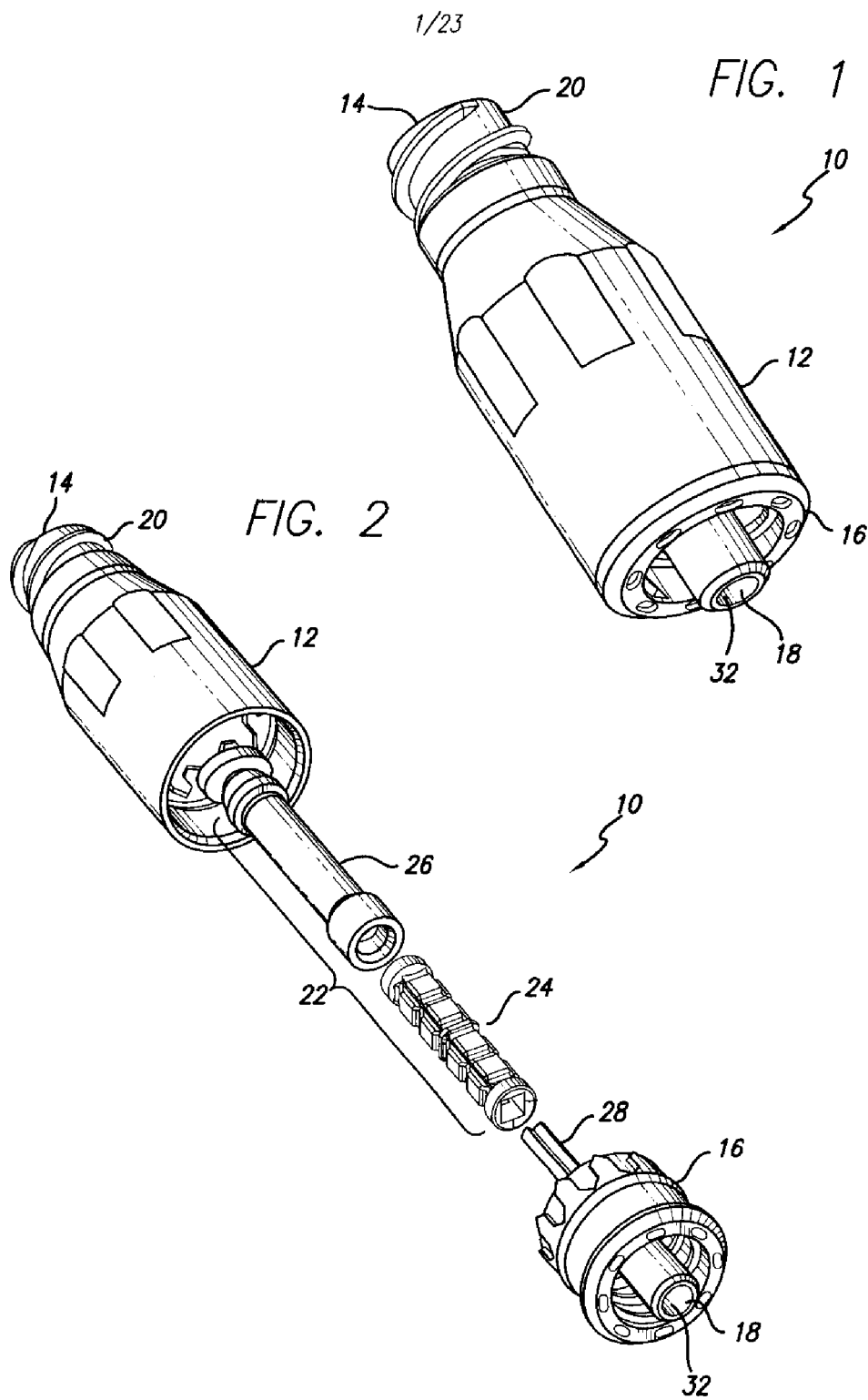

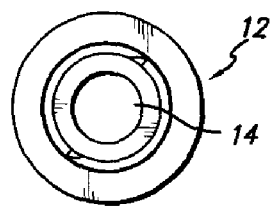
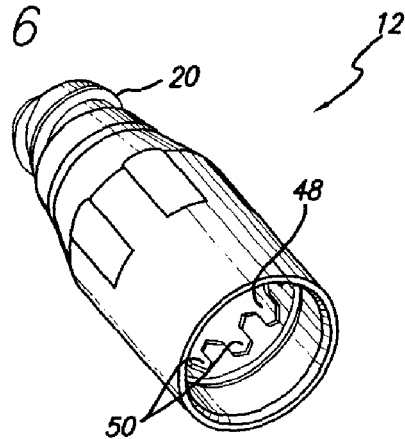
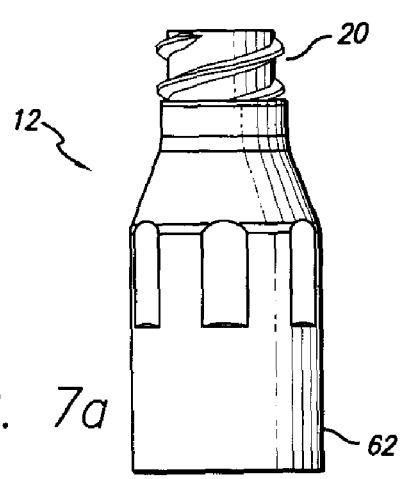
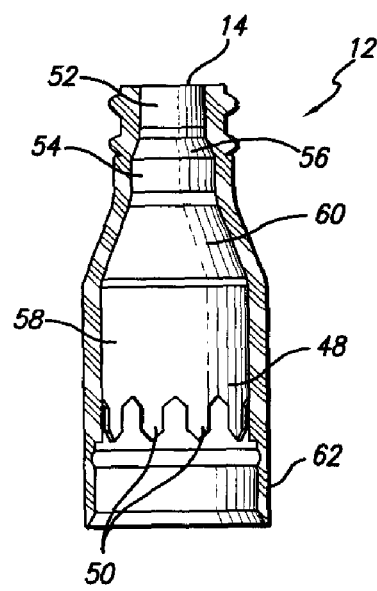
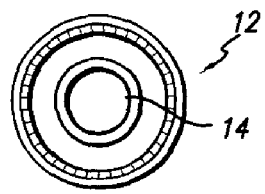

FIG. 8b
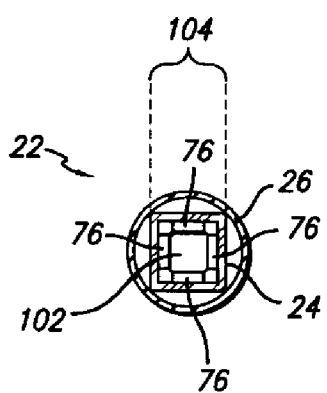
FIG. 9b
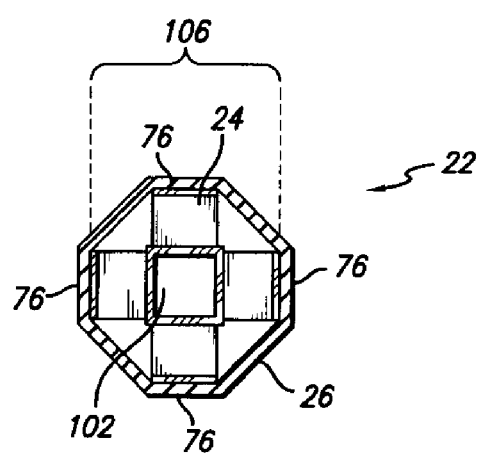
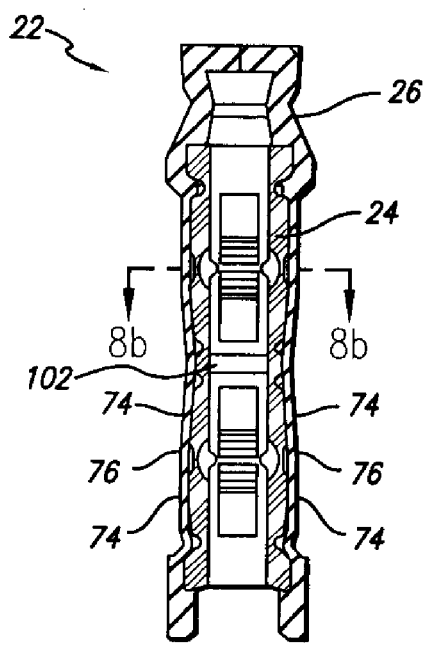
FIG. 8a
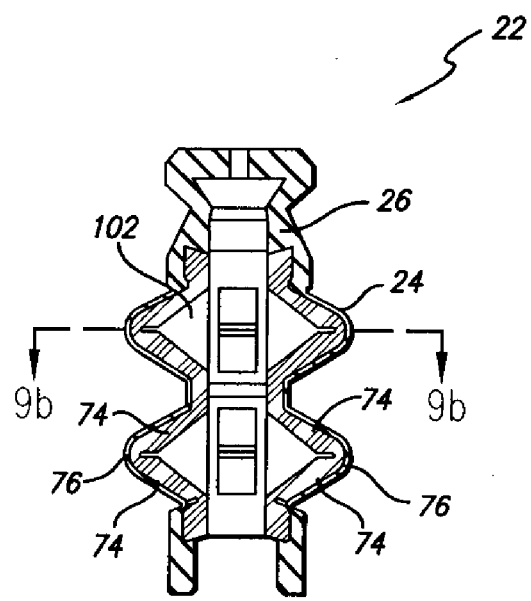
FIG. 9a

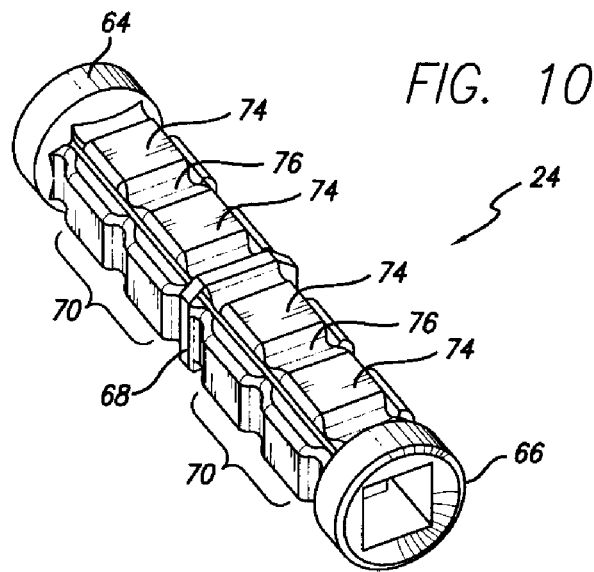
FIG. 10
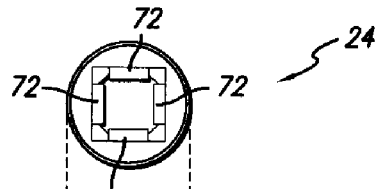
FIG. 11a
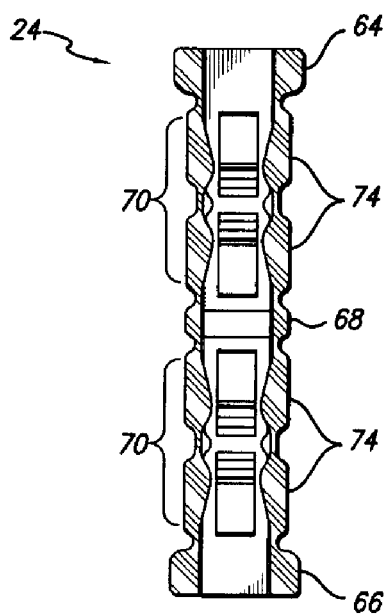
FIG. 11b
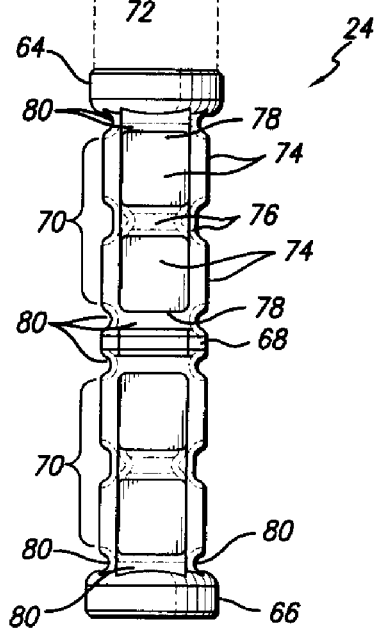

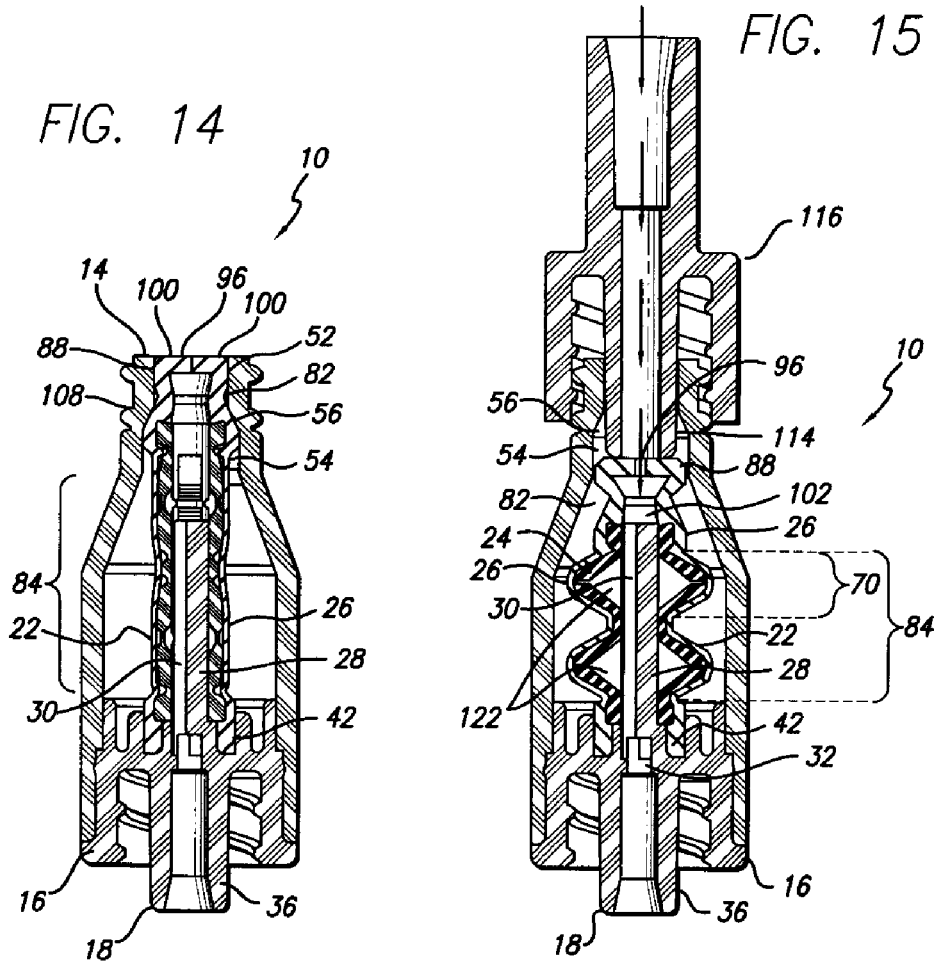
FIG. 14
FIG. 15
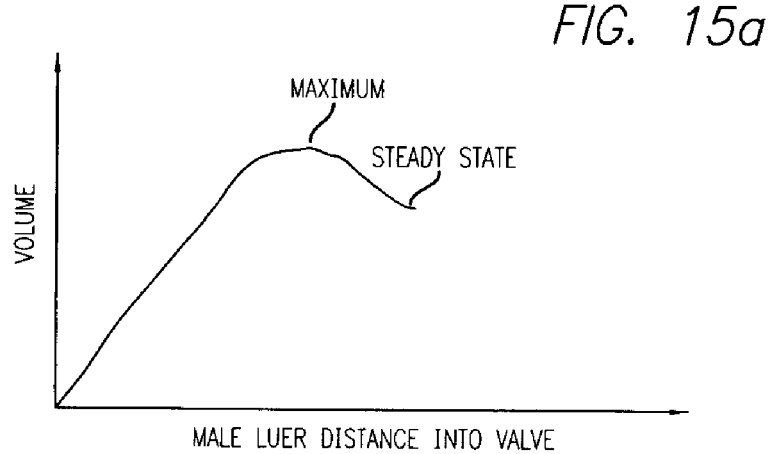
FIG. 15a

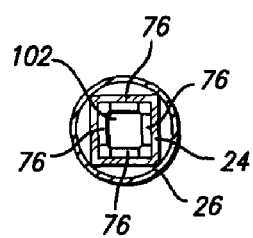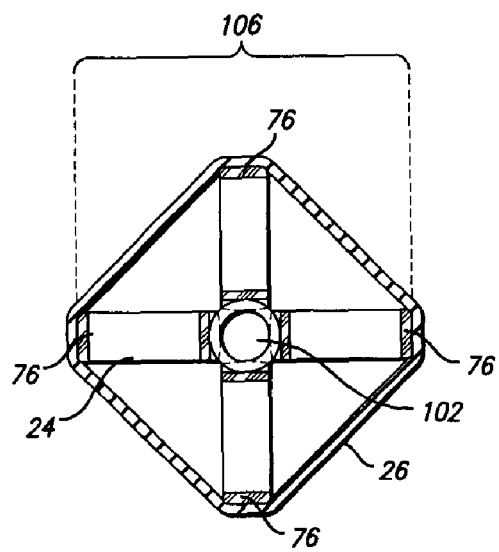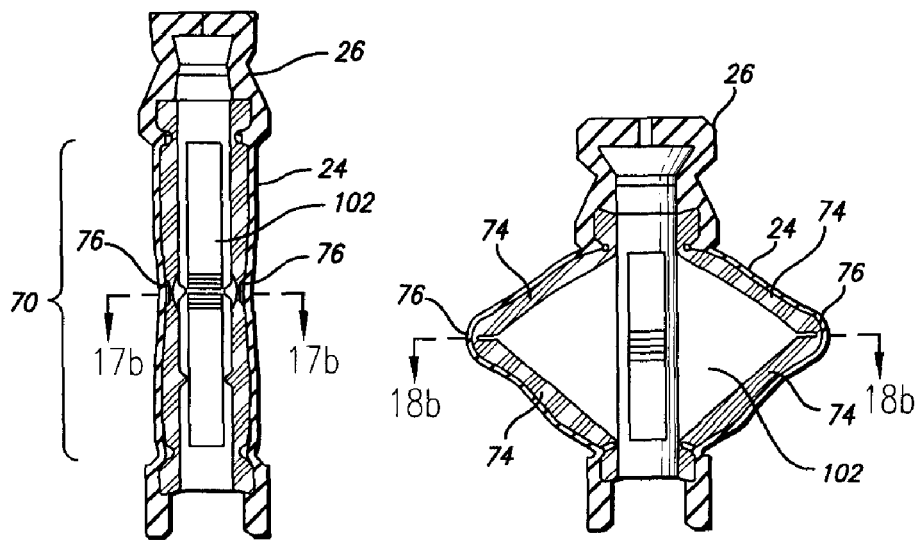
FIG. 17b
FIG. 18b
FIG. 17a
FIG. 18a